US011649248B2

(12) United States Patent
Virgili-Bernado et al.

(10) Patent No.: US 11,649,248 B2
(45) Date of Patent: May 16, 2023

(54) OXADIAZASPIRO COMPOUNDS FOR THE TREATMENT OF DRUG ABUSE AND ADDICTION

(71) Applicant: ESTEVE PHARMACEUTICALS, S.A., Barcelona (ES)

(72) Inventors: Marina Virgili-Bernado, Barcelona (ES); Carmen Almansa-Rosales, Barcelona (ES); Carlos Alegret-Molina, Barcelona (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 17/128,738

(22) Filed: Dec. 21, 2020

(65) Prior Publication Data

US 2021/0115062 A1  Apr. 22, 2021

Related U.S. Application Data

(63) Continuation of application No. 15/774,407, filed as application No. PCT/EP2016/001907 on Nov. 15, 2016, now Pat. No. 10,927,128.

(30) Foreign Application Priority Data

Nov. 16, 2015 (EP) .................................... 15382566

(51) Int. Cl.
  *C07D 498/10* (2006.01)
  *A61P 25/30* (2006.01)

(52) U.S. Cl.
  CPC ............ *C07D 498/10* (2013.01); *A61P 25/30* (2018.01)

(58) Field of Classification Search
  None
  See application file for complete search history.

(56) References Cited

U.S. PATENT DOCUMENTS

| | | | |
|---|---|---|---|
| 4,353,901 A | 9/1982 | Clark | |
| 4,353,900 A | 10/1982 | Clark | |
| 6,114,541 A | 9/2000 | Abrecht | |
| 8,168,783 B2 | 5/2012 | Kokubo et al. | |
| 2007/0105861 A1 | 5/2007 | Lee et al. | |
| 2008/0009495 A1 | 1/2008 | Kokubo | |
| 2009/0105290 A1 | 4/2009 | Sundermann et al. | |
| 2010/0120841 A1 | 5/2010 | Nakano et al. | |
| 2012/0264749 A1 | 10/2012 | Hadida-Ruah et al. | |
| 2017/0197984 A1 | 7/2017 | Virgili-Bernado et al. | |
| 2018/0009807 A1* | 1/2018 | deJesus ............... A61K 31/4178 | |

FOREIGN PATENT DOCUMENTS

| | | |
|---|---|---|
| CN | 101228127 | 7/2008 |
| DE | 102005030051 | 12/2006 |
| EP | 0061333 | 9/1982 |
| EP | 1634873 | 3/2006 |
| EP | 1847542 | 10/2007 |
| EP | 1982714 | 10/2008 |
| WO | WO 2005/084678 | 9/2005 |
| WO | WO2007098961 | 9/2007 |
| WO | WO 2008/105497 | 9/2008 |
| WO | WO 2008/155132 | 12/2008 |
| WO | WO 2009/032667 | 3/2009 |
| WO | WO2009071657 | 6/2009 |
| WO | WO 2009/098448 | 8/2009 |
| WO | WO 2012/156693 | 11/2012 |
| WO | WO2013052716 | 4/2013 |
| WO | WO2013115294 | 8/2013 |
| WO | WO 2015/017305 | 2/2015 |
| WO | WO 2015/185207 | 12/2015 |
| WO | WO 2015/185209 | 12/2015 |
| WO | WO 2016/122994 | 8/2016 |
| WO | WO 2017/084752 | 5/2017 |

OTHER PUBLICATIONS

Birajdar et al. "Synthesis and biological evaluation of amino alcohol derivatives of 2-methylbenzimidazole as antitubercular and antibacterial agents" Journal of Chemical and Pharmaceutical Research, 2013, vol. 5(11), p. 583-589.*
STN Registration No. 1445760-29-1, entered Jul. 19, 2013.
Zhang, et al., "Research progress of Sigma receptor antagonists in the drug abuse-mediated neurotoxicity," Journal of China Pharmaceutical University, 2014, 45, 253-258.
Alonso et al., Neuroscience. 2000;97(1):155-70.
Birajdar, Satish, S., et al., "Synthesis and biological evaluation of amino alcohol derivatives of 2-methylbenzimidazole as antitubercular and antibacterial agents", Journal of Chemical and Pharmaceutical Research, 2013, 5(11): 583-589.
Biasio et al., Behav Brain Res 2015; 287:315-22.
Bornot et al., J. Med. Chem., 2013, 56, 1197-1210.
Chen et al., Drug Alcohol Depend 2011; 117: 164-9.
Chien, et al., Neuroscience Letters, 1995, 190, 137-139.
Clark, Robin, D., et al.. "Antihypertensive 9-substituted 1-oxa-4,9-diazaspiro[5.5]undecan-3-ones", Journal of Medicinal Chemistry, American Chemical Society, vol. 26, No. 6, Jan. 1983, pp. 855-861.
Collina, Simona, et al., "Sigma receptor modulators:a patent review", Expert Opinioin on Therapeutic Patents, Informa Healthcare, vol. 23, No. 5, May 2013, pp. 597-613.
Database Registry, XP002730855, Chemical Abstracts Servier, May 12, 2010, Datbase Accession No. 1222524-76-6.
Dickenson, et al., Eur J Pain 9, 113-116 (2005).
Ela et al., J Pharmacol Exp Ther 1994; 269: 1300-9.
Friedman, et al., Angew. Chem. Int. Ed. 2013, 52, 9755-9758.
Goldberg, et al., BMC Public Health, 11, 770 (2011).
Hanner, M. et al. Proc. Natl. Acad. Sci., 1996, 93:8072-8077.
Horan et al., Eur J Pharmacol 2001; 426: R1-2.
International Search Report for PCT/EP2015/001115 dated Jun. 23, 2015.
International Search Report for PCT/EP2016/001907 dated Dec. 15, 2016.

(Continued)

*Primary Examiner* — Joseph R Kosack
(74) *Attorney, Agent, or Firm* — Hueschen and Sage

(57) ABSTRACT

The present invention relates to compounds having pharmacological activity towards the sigma (σ) receptor, and more particularly to oxadiazaspiro compounds having this pharmacological activity, to processes of preparation of such compounds, to pharmaceutical compositions comprising them, and to their use in therapy, in particular against drug abuse and addiction.

18 Claims, No Drawings

(56) References Cited

OTHER PUBLICATIONS

Kato, et al., Bioorganic & Medicinal Chemistry Letters, 2014, 24, 565-570.
Mao, et al., J. Pain, 12, 157-166 (2011).
Martin-Fardon et al., Neuropsychopharmacology. Sep. 2007;32(9):1967-73.
Martin-Fardon et al., Neuroreport. Oct. 3, 2012;23(14):809-13.
Matsumoto et al., Neuropharmacology 2001; 41: 878-886.
Matsumoto, Expert Rev Clin Pharmacol. Jul. 2009;2(4):361-8.
Maurice et al., Pharmacol Biochem Behav 2003; 74: 869-76.
McCracken et al., Eur J Pharmacol 1999; 370(3):225-32.
Morris et al., Curr Opin Pharmacol 2005: 5: 101-6.
Nguyen et al., Neuropharmacology 2005; 49: 638-45.
Okuyama et al., Life Sci. 1993;53(18):PL285-90.
Quirion, R. et al. Trends Pharmacol. Sci., 1992, 13:85-86.
Robson et al., Curr Pharm Des. 2012;18(7):902-19.
Roman et al., Gastroenterology 1989; 97:76-82.
Romieu et al., Neuroreport 2000; 11: 2885-8.
Samovilova and Vinogradov, Eur J Pharmacol 1992; 225: 69-74.
Snyder, S.H., Largent, B.L. J. Neuropsychiatry 1989, 1, 7-15.
Stocks, et al., Bioorganic & Medicinal Chemistry Letters, 2010, 20, 7458-7461.
Turk, et al., Lancet, 377, 2226-2235 (2011).
Walker, J.M. et al, Pharmacological Reviews, 1990, vol. 42, No. 4, 355-402.
Zamanilio, et al., Eur. J. Pharmacol, 716, 78-93 (2013).

\* cited by examiner

OXADIAZASPIRO COMPOUNDS FOR THE TREATMENT OF DRUG ABUSE AND ADDICTION

FIELD OF THE INVENTION

The present invention relates to new oxadiazaspiro compounds having affinity for sigma receptors, especially sigma-1 ($\sigma_1$) receptors, as well as to the process for the preparation thereof, to compositions comprising them, and to their use as medicaments against drug abuse and addiction.

BACKGROUND OF THE INVENTION

The search for new therapeutic agents has been greatly aided in recent years by better understanding of the structure of proteins and other biomolecules associated with target diseases. An important class of these proteins are the sigma ($\sigma$) receptors, cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M., et al, Pharmacological Reviews, 1990, 42, 355). It has been reported that the known sigma receptor ligand rimcazole clinically shows effects in the treatment of psychosis (Snyder, S. H., Largent B. L. J. Neuropsychiatry 1989, 1, 7).

The sigma receptor has at least two subtypes, the sigma-1 ($\sigma_1$) site, and the sigma 2, ($\sigma_2$) site.

The $\sigma_1$ receptor is a non-opiaceous type receptor expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for (+)SKF-10047, (+)-pentazocine, haloperidol and rimcazole, among others, known ligands with analgesic, anxiolytic, antidepressive, antiamnesic, antipsychotic and neuroprotective activity.

The $\sigma_2$ receptor is also expressed in numerous adult mammal tissues (e g nervous system, immune system, endocrine system, liver, kidney). $\sigma_2$ receptors can be components in a new apoptosis route that may play an important role in regulating cell proliferation or in cell development. This route seems to consist of $\sigma_2$ receptors joined to intracellular membranes, located in organelles storing calcium, such as the endoplasmic reticulum and mitochondria, which also have the ability to release calcium from these organelles. The calcium signals can be used in the signaling route for normal cells and/or in induction of apoptosis.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

For instance, the international patent application WO2007/098961 describes 4,5,6,7 tetrahydrobenzo[b]thiophene derivatives having pharmacological activity towards the sigma receptor.

Spiro[benzopyran] or spiro[benzofuran] derivatives were also disclosed in EP1847542 as well as pyrazole derivatives (EP1634873) with pharmacological activity on sigma receptors.

WO2009/071657 discloses some tricyclic triazolic compounds although structurally different to the ones of the current invention with activity towards sigma receptors.

Furthermore, the $\sigma_1$ receptor has become a promising target for developing new therapies aimed at treating the effects of a variety of abused drugs (Robson et al., Curr Pharm Des 2012; 18(7):902-19). It is known that the $\sigma_1$ receptor is expressed in brain regions involved in addictive processes, for example, hippocampus, striatal nucleus, nucleus accumbens and amygdala (Alonso et al., Neuroscience, 2000; 97(1): 155-70). It is also expressed in organs like the heart (Ela et al., J Pharmacol Exp Ther 1994; 269: 1300-9), liver (Samovilova and Vinogradov, Eur J Pharmacol 1992; 225: 69-74) or gastrointestinal system (Roman et al., Gastroenterology 1989; 97:76-82), organs involved in some of the side effects and many toxicities of abuse substances. Drugs such as cocaine (Matsumoto et al., Neuropharmacology 2001; 41: 878-86, 2007), methamphetamine (Nguyen et al., Neuropharmacology 2005; 49: 638-45) or phencyclidine (Morris et al., Curr Opin Pharmacol 2005; 5: 101-6) interact directly with the $\sigma_1$ receptor, which is involved in some of the effects of these substances. However, the $\sigma_1$ receptor can also modulate the effects of other drugs, even if they do not have affinity for the $\sigma_1$ receptor. This is the case of opiates such as morphine (Chen et al., Drug Alcohol Depend 2011; 117: 164-9), ethanol (Blasio et al., Behav Brain Res 2015; 287:315-22) or nicotine (Horan et al., Eur J Pharmacol 2001; 426: R1-2).

It is known that modulation of the $\sigma_1$ receptor is effective in blocking the reinforcing effects of cocaine (Romieu et al., Neuroreport 2000; 11: 2885-8), ethanol (Maurice et al., Pharmacol Biochem Behav 2003; 74: 869-76) or nicotine (Horan et al., Eur J Pharmacol 2001; 426: R1-2) in rodents, evaluated in the place conditioning test, and can also attenuate the reinstatement of cocaine (Martin-Fardon et al., Neuropsychopharmacology, 2007 September; 32(9):1967-73) or ethanol (Martin-Fardon et al., Neuroreport, 2012 Oct. 3; 23(14):809-13) self-administration response. It also inhibits the stimulating effects on locomotor activity induced by cocaine (McCracken et al., Eur J Pharmacol 1999; 370(3): 225-32) or methamphetamine (Okuyama et al., Life Sci. 1993; 53(18):PL285-90).

The precise mechanisms by which the $\sigma_1$ receptor ligands exert the observed effects are not fully elucidated. It is well known that the $\sigma_1$ receptor modulates neurotransmitter systems, such as dopaminergic, serotoninergic and glutamatergic, as well as the activity of ion channels, signalling pathways and expression of certain genes, all of them processes involved in the actions of drugs of abuse (Matsumoto, Expert Rev Clin Pharmacol. 2009 July; 2(4):351-8).

Drug addiction is one of the most serious health problems worldwide that impacts society on multiple levels. Drug abuse is responsible for significant medical, economic and social health costs. The ineffectiveness in some cases of current pharmacological treatments or, even, the lack of treatments, further aggravates the problem. All together support the need for deeper understanding of the neurobiological effects of drugs of abuse and addiction mechanisms, in order to discover new therapeutic targets for developing alternative treatments.

Additionally, there is still a need to find compounds having pharmacological activity towards the sigma receptor, being both effective, selective, and/or having good "drugability" properties, i.e. good pharmaceutical properties related to administration, distribution, metabolism and excretion.

Surprisingly, it has been observed that the new oxadiazaspiro compounds with general Formula (I) show an affinity for $\sigma_1$ receptor ranging from good to excellent. These compounds are therefore particularly suitable as pharmacologically active agents in medicaments for the prophylaxis and/or treatment of disorders or diseases related to sigma receptors, in particular against drug abuse and addiction.

SUMMARY OF THE INVENTION

The present invention discloses novel compounds with great affinity to sigma receptors and having high solubility in a physiological media which might be used for the treatment of sigma related disorders or diseases, in particular against drug abuse and addiction.

As this invention is aimed at providing a compound or a chemically related series of compounds which act as ligands of the $\sigma_1$ receptor, it is a very preferred embodiment if the compound has a binding expressed as $K_i$ which is preferably <1000 nM, more preferably <500 nM, even more preferably <100 nM.

The invention is directed in a main aspect to a compound of general Formula (I).

wherein $R_1$, $R_2$, $R_3$, $R_{3'}$, $R_4$, $R_{4'}$, $R_5$, $R_{5'}$, $R_6$, $R_{6'}$, X, Y, m, n and p are as defined below in the detailed description.

A further object of the invention refers to the processes for preparation of compounds of general formula (I).

A still further object of the invention refers to the use of intermediate compounds for the preparation of a compound of general formula (I).

It is also an object of the invention a pharmaceutical composition comprising a compound of formula (I).

Finally, it is an object of the invention the use of compound as a medicament and more particularly for the treatment of pain and pain related conditions.

DETAILED DESCRIPTION OF THE INVENTION

The present invention discloses novel compounds with affinity to sigma receptors and having high solubility in a physiological media which might be used for the treatment of sigma related disorders or diseases.

As this invention is aimed at providing a compound or a chemically related series of compounds which act as ligands of the $\sigma_1$ receptor it is a very preferred embodiment if the compound has a binding expressed as $K_i$ which is preferably <1000 nM, more preferably <500 nM, even more preferably <100 nM.

Advantageously, the compounds according to the present invention would in addition show one or more the following functionalities: $\sigma_1$ receptor antagonism. It has to be noted, though, that the functionalities "antagonism" and "agonism" are also sub-divided in their effect into subfunctionalities like partial agonism or inverse agonism. Accordingly, the functionalities of the compound should be considered within a relatively broad bandwidth.

An antagonist blocks or dampens agonist-mediated responses. Known subfunctionalities are neutral antagonists or inverse agonists.

An agonist increases the activity of the receptor above its basal level. Known subfunctionalities are full agonists, or partial agonists.

The invention is directed in a main aspect to a compound of general Formula (I).

In a particular aspect, the present invention is directed to compounds of general Formula (I):

wherein
p is 0 or 1 or 2; preferably p is 0 or 1;
m is 1, 2 or 3;
n is 0, 1 or 2;
Y is —CH$_2$— or —C(O)—;
X is a bond, —C(R$_x$R$_{x'}$)—, —C(O)— or —O—;
wherein R$_x$ is selected from halogen, substituted or unsubstituted C$_{1-6}$ alkyl, substituted or unsubstituted C$_{2-6}$ alkenyl substituted or unsubstituted C$_{2-6}$ alkalkynyl, and —OR$_8$;
R$_{x'}$ is selected from hydrogen, halogen or substituted or unsubstituted C$_{1-6}$ alkyl, substituted or unsubstituted C$_{2-6}$ alkenyl and substituted or unsubstituted C$_{2-6}$ alkynyl;
R$_8$ is selected from hydrogen, substituted or unsubstituted C$_{1-6}$ alkyl, substituted or unsubstituted C$_{2-6}$ alkenyl and substituted or unsubstituted C$_{2-6}$ alkynyl;
R$_1$ is selected from substituted or unsubstituted C$_{1-6}$ alkyl, substituted or unsubstituted C$_{2-6}$ alkenyl, substituted or unsubstituted C$_{2-6}$ alkynyl and substituted or unsubstituted cycloalkyl;

wherein said cycloalkyl in $R_1$ if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11'''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11'''}$ and $C(CH_3)_2OR_{11}$;

additionally, cycloalkyl in $R_1$, if substituted, may also be substituted with  or =O;

wherein the alkyl, alkenyl or alkynyl in $R_1$, if substituted, is substituted with one or more substituent/s selected from —$OR_{11}$, halogen, —CN, haloalkyl, haloalkoxy and —$NR_{11}R_{11'''}$;

wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, wherein said cycloalkyl, aryl or heterocyclyl in $R_2$, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12'''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;

additionally, cycloalkyl or non-aromatic heterocyclyl in $R_2$, if substituted, may also be substituted with  or =O;

wherein the alkyl, alkenyl or alkynyl in $R_2$, if substituted, is substituted with one or more substituent/s selected from —$OR_{12}$, halogen, —CN, haloalkyl, haloalkoxy and —$NR_{12}R_{12'''}$;

wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

$R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively, $R_3$ and $R_{3'}$, taken together with the connecting C-atom may form a substituted or unsubstituted cycloalkyl;

$R_4$ and $R_{4'}$ are independently selected from hydrogen, substituted or unsubstituted $C_{1-9}$ alkyl, substituted or unsubstituted $C_{2-9}$ alkenyl, substituted or unsubstituted $C_{2-9}$ alkynyl, —$CHOR_9$ and —$C(O)OR_9$;

wherein $R_9$ is selected from hydrogen, substituted or unsubstituted $C_{1-9}$ alkyl, substituted or unsubstituted $C_{2-9}$ alkenyl and substituted or unsubstituted $C_{2-9}$ alkynyl;

$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$CHOR_7$ and —$C(O)OR_7$;

wherein $R_7$ is selected from hydrogen, substituted or unsubstituted $C_{1-6}$ alkyl, substituted or unsubstituted $C_{2-6}$ alkenyl and substituted or unsubstituted alkynyl;

alternatively, $R_5$ and $R_{5'}$ taken together with the connecting C-atom may form a substituted or unsubstituted cycloalkyl or a substituted or unsubstituted non-aromatic heterocyclyl;

$R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$OR_{10}$, —$CHOR_{10}$ and —$C(O)OR_{10}$;

wherein $R_{10}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof;

In a particular aspect, the present invention is directed to compounds of general Formula (I):

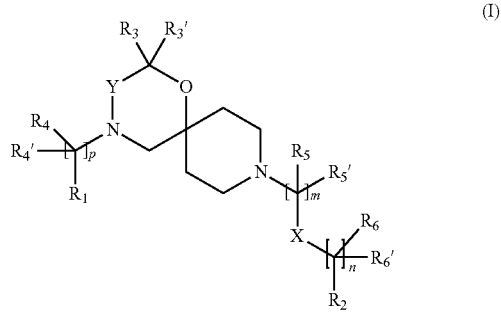

(I)

wherein
p is 0 or 1;
m is 1, 2 or 3;
n is 0, 1 or 2;
Y is —$CH_2$— or —C(O)—;
X is a bond, —$C(R_xR_{x'})$—, —C(O)— or —O—;
wherein $R_x$ is selected from halogen, substituted or unsubstituted $C_{1-6}$ alkyl, substituted or unsubstituted $C_{2-6}$ alkenyl substituted or unsubstituted $C_{2-6}$ alkynyl, and —$OR_8$;
$R_{x'}$ is selected from hydrogen, halogen or substituted or unsubstituted $C_{1-6}$ alkyl, substituted or unsubstituted $C_{2-6}$ alkenyl and substituted or unsubstituted $C_{2-6}$ alkynyl;
$R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_1$ is selected from substituted or unsubstituted $C_{1-6}$ alkyl, substituted or unsubstituted $C_{2-6}$ alkenyl, substituted or unsubstituted $C_{2-6}$ alkynyl and substituted or unsubstituted cycloalkyl;
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

R₃ and R₃' are independently selected from hydrogen, substituted or unsubstituted C₁₋₆ alkyl, substituted or unsubstituted C₂₋₆ alkenyl and substituted or unsubstituted C₂₋₆ alkynyl;

alternatively, R₃ and R₃', taken together with the connecting C-atom may form a substituted or unsubstituted cycloalkyl;

R₄ and R₄' are independently selected from hydrogen, substituted or unsubstituted C₁₋₉ alkyl, substituted or unsubstituted C₂₋₉ alkenyl, substituted or unsubstituted C₂₋₉ alkynyl, —CHOR₉ and —C(O)OR₉;

wherein R₉ is selected from hydrogen, substituted or unsubstituted C₁₋₉ alkyl, substituted or unsubstituted C₂₋₉ alkenyl and substituted or unsubstituted C₂₋₉ alkynyl;

R₅ and R₅' are independently selected from hydrogen, substituted or unsubstituted C₁₋₆ alkyl, substituted or unsubstituted C₂₋₆ alkenyl, substituted or unsubstituted C₂₋₆ alkynyl, —CHOR₇ and —C(O)OR₇;

wherein R₇ is selected from hydrogen, substituted or unsubstituted C₁₋₆ alkyl, substituted or unsubstituted C₂₋₆ alkenyl and substituted or unsubstituted C₂₋₆ alkynyl;

alternatively, R₅ and R₅' taken together with the connecting C-atom may form a substituted or unsubstituted cycloalkyl or a substituted or unsubstituted non-aromatic heterocyclyl;

R₆ and R₆' are independently selected from hydrogen, substituted or unsubstituted C₁₋₆ alkyl, substituted or unsubstituted C₂₋₆ alkenyl, substituted or unsubstituted C₂₋₆ alkynyl, —OR₁₀, —CHOR₁₀ and —C(O)OR₁₀;

wherein R₁₀ is selected from hydrogen, substituted or unsubstituted C₁₋₆ alkyl, substituted or unsubstituted C₂₋₆ alkenyl and substituted or unsubstituted C₂₋₆ alkynyl;

These compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment, these compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In a further embodiment the following proviso applies:
when Y is —C(O)— and R₂ is substituted or unsubstituted aryl or substituted or unsubstituted heterocyclyl, then m is 1, X is a bond, in is 0 and R₃ is not hydrogen.

In a further embodiment the following proviso applies:
when Y is —C(O)— and R₂ is substituted or unsubstituted monocyclic aryl or substituted or unsubstituted monocyclic heterocyclyl, then m is 1, X is a bond, n is 0 and R₃ is not hydrogen.

In a further embodiment the following proviso applies:
when Y is —C(O)— and R₂ is substituted or unsubstituted aryl or substituted or unsubstituted heterocyclyl, then m is 1, X is a bond and n is 0.

In a further embodiment the following proviso applies:
when Y is —C(O)— and R₂ is substituted or unsubstituted monocyclic aryl or substituted or unsubstituted monocyclic heterocyclyl, then m is 1, X is a bond and n is 0.

In a further embodiment the following proviso applies:
when Y is —C(O)— and R₂ is substituted or unsubstituted aryl or substituted or unsubstituted heterocyclyl, then —[CR₅R₅']ₘ—X—[CR₆R₆']ₙ— is neither —CH₂CH₂— nor —CH₂CH(OH)—, and R₃ is not hydrogen.

For the sake of clarity regarding —CH₂CH(OH)—, this would mean that when Y is —C(O)— and R₂ is substituted or unsubstituted aryl or substituted or unsubstituted heterocyclyl, then —[CR₅R₅']ₘ—X—[CR₆R₆']ₙ— could not be —CH₂CH(OH)— read in the direction from the "N" of the spiro-part of the core towards R₂.

In a further embodiment the following compound is further excluded:

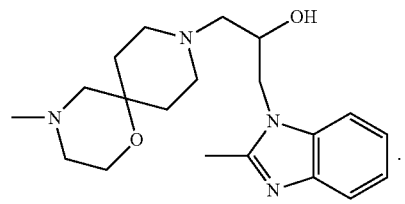 [SMILES: Cc1nc2ccccc2n1CC(O)CN1CCC2(CC1)CN(C)CCO2]

In a further embodiment the following compound is excluded:

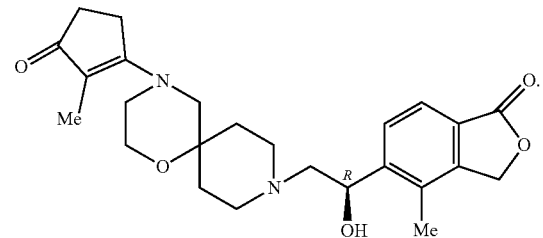

In a further embodiment both following compounds are further excluded:

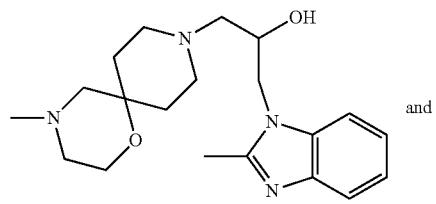

and

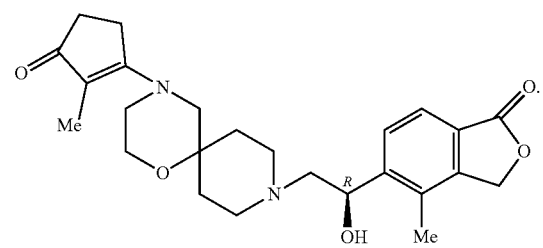

In a further embodiment the compound according to the invention of general Formula (I) is a compound of general Formula (I')

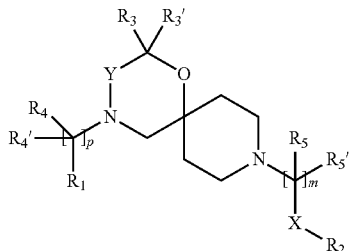
(I')

wherein, $R_1$, $R_2$, $R_3$, $R_{3'}$, $R_4$, $R_{4'}$, $R_5$, $R_{5'}$, X, Y, m and p are as defined in the description.

In a further embodiment the compound according to the invention of general Formula (I) is a compound of general Formula ($I^{a'}$)

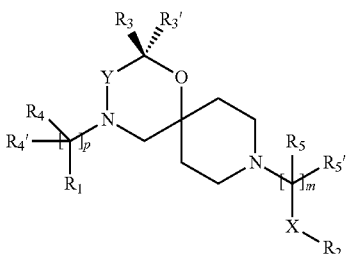
($I^{a'}$)

wherein, $R_1$, $R_2$, $R_3$, $R_{3'}$, $R_4$, $R_{4'}$, $R_5$, $R_{5'}$, X, Y, m and p are as defined in the description.

In a further embodiment the compound according to the invention of general Formula

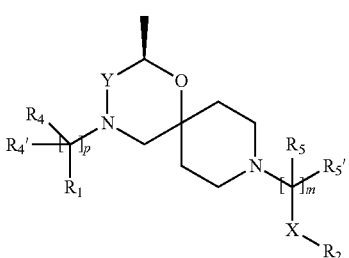
($I^{b'}$)

wherein, $R_1$, $R_2$, $R_4$, $R_{4'}$, $R_5$, $R_{5'}$, X, Y, m and p are as defined in the description.

In a further embodiment the compound according to the invention of general Formula (I) is a compound of general Formula ($I^{c'}$).

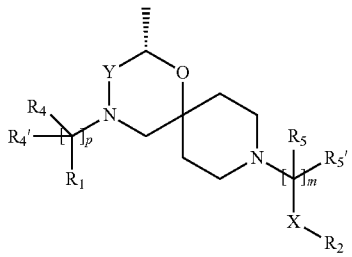
($I^{c'}$)

wherein, $R_1$, $R_2$, $R_4$, $R_{4'}$, $R_5$, $R_{5'}$, X, Y, m and p are as defined in the description.

In a further embodiment the compound according to the invention of general Formula (I) is a compound of general Formula ($I^{2'}$)

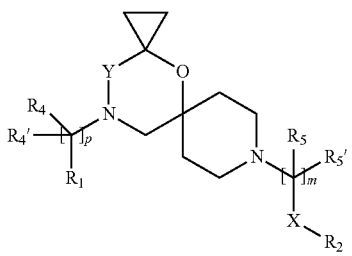
($I^{2'}$)

wherein $R_1$, $R_2$, $R_4$, $R_{4'}$, $R_5$, $R_{5'}$, X, Y, m and p are as defined in the description.

In a further embodiment, for compounds of general Formula (I) are compounds of general Formula ($I^{3'}$)

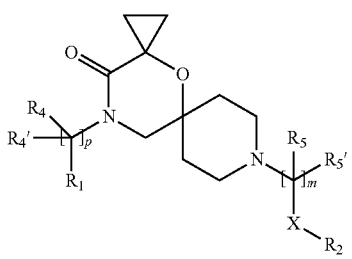
($I^{3'}$)

wherein $R_1$, $R_2$, $R_4$, $R_{4'}$, $R_5$, $R_{5'}$, X, m and p are as defined in the description.

In a further embodiment, for compounds of general Formula (I) are compounds of general Formula ($I^{4'}$)

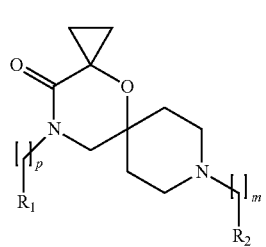
($I^{4'}$)

wherein $R_1$, $R_2$, m and p are as defined in the description.

In a further embodiment, for compounds of general Formula (I) are compounds of general Formula (I$^{5'}$)

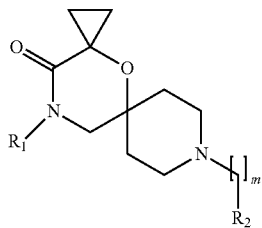

wherein $R_1$, $R_2$, and m are as defined in the description.

In a further embodiment the compound according to the invention of general Formula (I) is a compound of general Formula (I$^{6'}$)

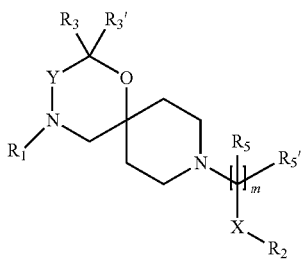

wherein, $R_1$, $R_2$, $R_3$, $R_{3'}$, $R_5$, $R_{5'}$, X, Y, and m are as defined in the description.

For clarity purposes, reference is also made to the following statements below in the definitions of substitutions on alkyl etc. or aryl etc. that "wherein when different radicals $R_1$ to $R_{14'''}$ and $R_x$, $R_{x'}$ are present simultaneously in Formula I they may be identical or different". This statement is reflected in the below general Formula (I$^{7'}$) being derived from and falling into general Formula (I).

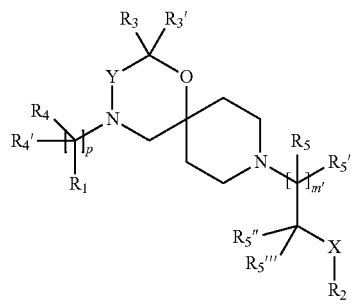

wherein $R_1$, $R_2$, $R_3$, $R_{3'}$, $R_4$, $R_{4'}$, $R_5$, $R_{5'}$, X, Y and p are as defined in the description. In addition, m' (being 0 or 1), $R_{5''}$ and $R_{5'''}$ are added. As said above, this statement is thus reflected in that $R_{5''}$ and $R_{5'''}$ are or could be different from $R_5$ and $R_{5'}$, or not and—accordingly—m' being 0 or 1 is naturally resulting from m (in general Formulas (I) to (I$^{6'}$) being 1 or 2).

The same would be applicable mutatis mutandis for general Formulas like general Formula (I) as well as the other general Formulas (I') to (I$^6$) above, as well as to all the intermediates of synthesis.

For clarity purposes, all groups and definitions described in the description and referring to compounds of general Formula (I), also apply to compounds of general Formula (I'), (I$^{a'}$), (I$^{b'}$), (I$^{c'}$), (I$^{2'}$), (I$^{3'}$), (I$^{4'}$), (I$^{5'}$), or (I$^{6'}$) or (I$^{7'}$), as well as to all the intermediates of synthesis, when those groups are present in the mentioned general Markush formulae, since compounds of general Formula (I'), (I$^{a'}$), (I$^{b'}$), (I$^{c'}$), (I$^{2'}$), (I$^{3'}$), (I$^{4'}$), (I$^{5'}$), (I$^{6'}$) or (I$^{7'}$) are included in the general Formula (I).

For clarity purposes, the general Markush Formula (I)

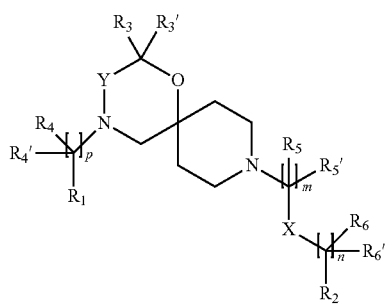

is equivalent to

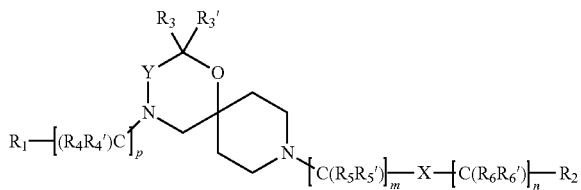

wherein only —C($R_4R_{4'}$)—, —C($R_5R_{5'}$)— and —C($R_6R_{6'}$)— are included into the brackets and p, m and n mean the number of times that —C($R_4R_{4'}$)—, —C($R_5R_{5'}$)— and —C($R_6R_{6'}$)— are repeated, respectively. The same would apply to general Markush Formulae (I'), (I$^{a'}$), (I$^{b'}$), (I$^{c'}$), (I$^{2'}$), (I$^{3'}$), (I$^{4'}$), (I$^{5'}$) or (I$^{6'}$) as well as to all the intermediates of synthesis.

Thus, general Formula (I') could also be expressed as general Formula (IZ') etc.:

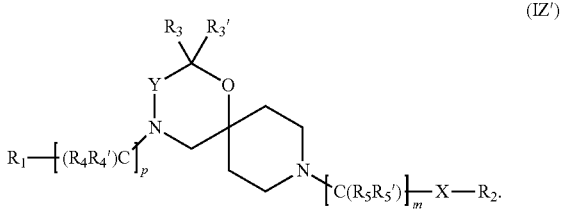

In addition, and for clarity purposes, it should further be understood that naturally if p, m or n are 0, then $R_1$, X or $R_2$ are still present in general Markush Formulae (I'), (I$^{a'}$), (I$^{b'}$), (I$^{c'}$), (I$^{2'}$), (I$^{3'}$), (I$^{4'}$), (I$^{5'}$) or (I$^{6'}$) as well as in all the intermediates of synthesis.

In the context of this invention, alkyl is understood as meaning saturated, linear or branched hydrocarbons, which may be unsubstituted or substituted once or several times. It encompasses e.g. —CH$_3$ and —CH$_2$—CH$_3$. In these radicals, C$_{1-2}$-alkyl represents C1- or C2-alkyl, C$_{1-3}$-alkyl represents C1-, C2- or C3-alkyl, C$_{1-4}$-alkyl represents C1-, C2-, C3- or C4-alkyl, C$_{1-5}$-alkyl represents C1-, C2-, C3-, C4-, or C5-alkyl, C$_{1-6}$-alkyl represents C1-, C2-, C3-, C4-, C5- or C6-alkyl, C$_{1-7}$-alkyl represents C1-, C2-, C3-, C4-, C5-, C6- or C7-alkyl, C$_{1-8}$-alkyl represents C1-, C2-, C3-, C4-, C5-, C6-, C7- or C8-alkyl, C$_{1-10}$-alkyl represents C1-, C2-, C3-, C4-, C5-, C6-, C7-, C8-, C9- or C10-alkyl and C$_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also CHF$_2$, CF$_3$ or CH$_2$OH etc. Preferably alkyl is understood in the context of this invention as C$_{1-8}$alkyl like methyl, ethyl, propyl, butyl, pentyl, hexyl, heptyl, or octyl; preferably is C$_{1-6}$alkyl like methyl, ethyl, propyl, butyl, pentyl, or hexyl; more preferably is C$_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH═CH—CH$_3$. The alkenyl radicals are preferably vinyl (ethenyl), allyl (2-propenyl). Preferably in the context of this invention alkenyl is C$_{2-10}$-alkenyl or C$_{2-8}$-alkenyl like ethylene, propylene, butylene, pentylene, hexylene, heptylene or octylene; or is C$_{2-6}$-alkenyl like ethylene, propylene, butylene, pentylene, or hexylene; or is C$_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—CH$_3$ (1-propinyl). Preferably alkynyl in the context of this invention is C$_{2-10}$-alkynyl or C$_{2-8}$-alkynyl like ethyne, propyne, butyene, pentyne, hexyne, heptyne, or octyne; or is C$_{2-6}$-alkynyl like ethyne, propyne, butyene, pentyne, or hexyne; or is C$_{2-4}$-alkynyl like ethyne, propyne, butyene, pentyne, or hexyne.

In connection with alkyl (also in alkylaryl, alkylheterocyclyl or alkylcycloalkyl), alkenyl, alkynyl and O-alkyl—unless defined otherwise—the term substituted in the context of this invention is understood as meaning replacement of at least one hydrogen radical on a carbon atom by halogen (F, Cl, Br, I), —NR$_c$R$_{c'''}$, —SR$_c$, —S(O)R$_c$, —S(O)$_2$R$_c$, —OR$_c$, —C(O)OR$_c$, —CN, —C(O)NR$_c$R$_c$, haloalkyl, haloalkoxy or —OC$_{1-6}$alkyl, being R$_c$ represented by R$_{11}$, R$_{12}$, R$_{13}$, (being R$_{c'}$ represented by R$_{11'}$, R$_{12'}$, R$_{13'}$, being R$_{c''}$ represented by R$_{11''}$, R$_{12''}$, R$_{13''}$; being R$_{c'''}$ represented by R$_{11'''}$, R$_{12'''}$, R$_{13'''}$, being R$_{c''''}$ represented by R$_{11''''}$, R$_{12''''}$, R$_{13''''}$) wherein R$_1$ to R$_{14''''}$ and R$_x$, R$_{x'}$ and R$_n$ are as defined in the description, and wherein when different radicals R$_1$ to R$_{14''''}$ and R$_x$, R$_{x'}$ and R$_n$ are present simultaneously in Formula I they may be identical or different.

Most preferably in connection with alkyl (also in alkylaryl, alkylheterocyclyl or alkylcycloalkyl), alkenyl, alkynyl or O-alkyl, substituted is understood in the context of this invention that any alkyl (also in alkylaryl, alkylheterocyclyl or alkylcycloalkyl), alkenyl, alkynyl or O-alkyl which is substituted is substituted with one or more of halogen (F, Cl, Br, I), —OR$_c$, —CN, —NR$_c$R$_{c'''}$, haloalkyl, haloalkoxy or —OC$_{1-6}$alkyl, being R$_c$ represented by R$_{11}$, R$_{12}$, R$_{13}$, (being R$_{c'}$ represented by R$_{11'}$, R$_{12'}$, R$_{13'}$; being R$_{c''}$ represented by R$_{11''}$, R$_{12''}$, R$_{13''}$; being R$_{c'''}$ represented R$_{11'''}$, R$_{12'''}$, R$_{13'''}$; being R$_{c''''}$ represented by R$_{11''''}$, R$_{12''''}$, R$_{13''''}$), wherein R$_1$ to R$_{14''''}$ and R$_x$, R$_{x'}$ and R$_n$ are as defined in the description, and wherein when different radicals R$_1$ to R$_{14''''}$ and R$_x$, R$_{x'}$ and R$_n$ are present simultaneously in Formula I, they may be identical or different.

More than one replacement on the same molecule and also on the same carbon atom is possible with the same or different substituents. This includes for example 3 hydrogens being replaced on the same C atom, as in the case of CF$_3$, or at different places of the same molecule, as in the case of e.g. —CH(OH)—CH═CH—CHCl$_2$.

In the context of this invention haloalkyl is understood as meaning an alkyl being substituted once or several times by a halogen (selected from F, Cl, Br, I). It encompasses e.g. —CH$_2$Cl, —CH$_2$F, —CHCl$_2$, —CHF$_2$, —CCl$_3$, —CF$_3$ and —CH$_2$—CHCl$_2$. Preferably haloalkyl is understood in the context of this invention as halogen-substituted C$_{1-4}$-alkyl representing halogen substituted C1-, C2-, C3- or C4-alkyl. The halogen-substituted alkyl radicals are thus preferably methyl, ethyl, propyl, and butyl. Preferred examples include —CH$_2$Cl, —CH$_2$F, —CHCl$_2$, —CHF$_2$, and —CF$_3$.

In the context of this invention haloalkoxy is understood as meaning an —O-alkyl being substituted once or several times by a halogen (selected from F, Cl, Br, I). It encompasses e.g. —OCH$_2$Cl, —OCH$_2$F, —OCHCl$_2$, —OCHF$_2$, —OCCl$_3$, —OCF$_3$ and —OCH$_2$—CHCl$_2$. Preferably haloalkyl is understood in the context of this invention as halogen-substituted —OC$_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —OCH$_2$Cl, —OCH$_2$F, —OCHCl$_2$, —OCHF$_2$, and —OCF$_3$.

In the context of this invention cycloalkyl is understood as meaning saturated and unsaturated (but not aromatic) cyclic hydrocarbons (without a heteroatom in the ring), which can be unsubstituted or once or several times substituted. Furthermore. C$_{3-4}$-cycloalkyl represents C3- or C4-cycloalkyl, C$_{3-5}$-cycloalkyl represents C3-, C4- or C5-cycloalkyl, C$_{3-6}$-cycloalkyl represents C3-, C4-, C5- or C6-cycloalkyl. C$_{3-7}$-cycloalkyl represents C3-, C4-, C5-, C6- or C7-cycloalkyl, C$_{3-8}$-cycloalkyl represents C3-, C4-, C5-, C6-, C7- or C8-cycloalkyl. C$_{4-5}$-cycloalkyl represents C4- or C5-cycloalkyl, C$_{4-6}$-cycloalkyl represents C4-, C5- or C6-cycloalkyl, C$_{4-7}$-cycloalkyl represents C4-, C5-, C6- or C7-cycloalkyl, C$_{5-6}$-cycloalkyl represents C5- or C6-cycloalkyl and C$_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is C$_{3-8}$cycloalkyl like cyclopropyl, cyclobutyl, cyclopentyl, cyclohexyl, cycloheptyl, or cyclooctyl; or is C$_{3-7}$cycloalkyl like cyclopropyl, cyclobutyl, cyclopentyl, cyclohexyl, or cycloheptyl; or is C$_{3-6}$cycloalkyl like cyclopropyl, cyclobutyl, cyclopentyl or cyclohexyl, especially cyclopentyl or cyclohexyl.

Aryl is understood as meaning 5 to 18 membered mono or polycyclic ring systems with at least one aromatic ring but without heteroatoms even in only one of the rings. Examples are phenyl, naphthyl, fluoranthenyl, fluorenyl, tetralinyl or indanyl, 9H-fluorenyl or anthracenyl radicals, which can be unsubstituted or once or several times substituted. Most preferably aryl is understood in the context of this invention as phenyl, naphtyl or anthracenyl, preferably is phenyl.

A heterocyclyl radical or group (also called heterocyclyl hereinafter) is understood as meaning 5 to 18 membered mono or polycyclic heterocyclic ring systems, with at least one saturated or unsaturated ring which contains one or more heteroatoms from the group consisting of nitrogen, oxygen and/or sulfur in the ring. A heterocyclic group can also be substituted once or several times.

Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.
- the heteroaryl (being equivalent to heteroaromatic radicals or aromatic heterocyclyls) is an aromatic 5 to 18 membered mono or polycyclic heterocyclic ring system of one or more rings of which at least one aromatic ring contains one or more heteroatoms from the group consisting of nitrogen, oxygen and/or sulfur in the ring, preferably is an aromatic 5 to 18 membered mono or polycyclic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;
- the non-aromatic heterocyclyl is a 5 to 18 membered mono or polycyclic heterocyclic ring system of one or more rings of which at least one ring—with this (or these) ring(s) then not being aromatic—contains one or more heteroatoms from the group consisting of nitrogen, oxygen and/or sulfur in the ring; preferably is a 5 to 18 membered mono or polycyclic heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, oxetane, especially is benzodioxane, morpholine, tetrahydropyran, piperidine, oxopyrrolidine, oxetane and pyrrolidine.

Preferably, in the context of this invention heterocyclyl is defined as a 5 to 18 membered mono or polycyclic heterocyclic ring system of one or more saturated or unsaturated rings of which at least one ring contains one or more heteroatoms from the group consisting of nitrogen, oxygen and/or sulfur in the ring. Preferably it is a 5 to 18 membered mono or polycyclic heterocyclic ring system of one or two saturated or unsaturated rings of which at least one ring contains one or more heteroatoms from the group consisting of nitrogen, oxygen and/or sulfur in the ring.

Preferred examples of heterocyclyls include oxetane, oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b]pyridine, benzoxazole, oxopyrrolidine, pyrimidine, oxazepane, oxetane and pyrrolidine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heteracyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

In the context of this invention alkylaryl is understood as meaning an aryl group (see above) being connected to another atom through a $C_{1-6}$-alkyl (see above) which may be branched or linear and is unsubstituted or substituted once or several times. Preferably alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylheterocyclyl is understood as meaning an heterocyclyl group being connected to another atom through a $C_{1-6}$-alkyl (see above) which may be branched or linear and is unsubstituted or substituted once or several times. Preferably alkylheterocyclyl is understood as meaning an heterocyclyl group (see above) being connected to another atom through 1 to 4 (—$CH_2$—) groups. Most preferably alkylheterocyclyl is —$CH_2$-pyridine.

In the context of this invention alkylcycloalkyl is understood as meaning an cycloalkyl group being connected to another atom through a $C_{1-6}$-alkyl (see above) which may be branched or linear and is unsubstituted or substituted once or several times. Preferably alkylcycloalkyl is understood as meaning an cycloalkyl group (see above) being connected to another atom through 1 to 4 (—$CH_2$—) groups. Most preferably alkylcycloalkyl is —$CH_2$-cyclopropyl.

Preferably, the aryl is a monocyclic aryl. More preferably the aryl is a 5, 6 or 7 membered monocyclic aryl. Even more preferably the aryl is a 5 or 6 membered monocyclic aryl.

Preferably, the heteroaryl is a monocyclic heteroaryl. More preferably the heteroaryl is a 5, 6 or 7 membered monocyclic heteroaryl. Even more preferably the heteroaryl is a 5 or 6 membered monocyclic heteroaryl.

Preferably, the non-aromatic heterocyclyl is a monocyclic non-aromatic heterocyclyl. More preferably the non-aromatic heterocyclyl is a 4, 5, 6 or 7 membered monocyclic non-aromatic heterocyclyl. Even more preferably the non-aromatic heterocyclyl is a 5 or 6 membered monocyclic non-aromatic heterocyclyl.

Preferably, the cycloalkyl is a monocyclic cycloalkyl. More preferably the cycloalkyl is a 3, 4, 5, 6, 7 or 8 membered monocyclic cycloalkyl. Even more preferably the cycloalkyl is a 3, 4, 5 or 6 membered monocyclic cycloalkyl.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl, heterocyclyl or alkyl-heterocyclyl with one or more of halogen (F, Cl, Br, I), —$R_c$, —$OR_c$, —CN, —$NO_2$, —$NR_c$ $R_{c'''}$, —C(O)$OR_c$, $NR_cC(O)R_{c'}$, —C(O)$NR_cR_{c'}$, —$NR_cS(O)_2R_{c'}$, =O, —OCH$_2$CH$_2$OH, —$NR_cC(O)NR_{c'}R_{c''}$, —S(O)$_2NR_cR_{c'}$, —$NR_cS(O)_2NR_{c'}R_{c''}$, haloalkyl, haloalkoxy, —$SR_c$, —S(O)$R_c$, —S(O)$_2R_c$ or C(CH$_3$)$OR_c$; $NR_cR_{c'''}$, with $R_c$, $R_{c'}$, $R_{c''}$ and $R_{c'''}$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_c$ one of $R_{11}$, $R_{12}$ or $R_{14}$, (being $R_{c'}$ one of $R_{11'}$, $R_{12'}$ or $R_{14'}$; being $R_{c''}$ one of $R_{11''}$, $R_{12''}$ or $R_{14''}$, being $R_{c'''}$ one of $R_{11'''}$, $R_{12'''}$ or $R_{14'''}$; being $R_{c''''}$ one of $R_{11''''}$, $R_{12''''}$ or $R_{14''''}$), wherein $R_1$ to $R_{14''''}$ and $R_x$, $R_{x'}$ and $R_n$ are as defined in the description, and wherein when different radicals $R_1$ to $R_{14''''}$ and $R_x$, $R_{x'}$ and $R_n$ are present simultaneously in Formula I they may be identical or different.

Most preferably in connection with aryl (including a alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted is substituted (also in an alkylaryl, alkylcycloalkyl or alkylheterocyclyl) with one or more of halogen (F, Cl, Br, I), —$R_c$, —$OR_c$, —CN, —NO$_2$, —$NR_cR_{c'''}$, —$NR_cC(O)R_{c'}$, —$NR_cS(O)_2R_{c'}$, =O, haloalkyl, haloalkoxy, or C(CH$_3$)$OR_{c'}$, —$OC_{1-4}$-alkyl being unsubstituted or substituted with one or more of $OR_c$ or halogen (F, Cl, I, Br), —CN, or —$C_{1-4}$alkyl being unsubstituted or substituted with one or more of $OR_c$ or halogen (F, Cl, I, Br), being $R_c$ and one of $R_{11}$, $R_{12}$ or $R_{14}$, (being $R_{c'}$ one of $R_{11'}$, $R_{12'}$ or $R_{14'}$, being $R_{c''}$ one of $R_{11''}$, $R_{12''}$ or $R_{14''}$; being $R_{c'''}$ one of $R_{11'''}$, $R_{12'''}$ or $R_{14'''}$; being $R_{c''''}$ one of $R_{11''''}$, $R_{12''''}$ or $R_{14''''}$), wherein $R_1$ to $R_{14''''}$ and $R_x$, $R_{x'}$ and $R_n$ are as defined in the description, and wherein when different radicals $R_1$ to $R_{14''''}$ and $R_x$, $R_{x'}$ and $R_n$ are present simultaneously in Formula I they may be identical or different.

Additionally to the above-mentioned substitutions, in connection with cycloalkyl (including alkyl-cycloalkyl), or heterocycly (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with  or =O.

In connection with cycloalkyl (including alkyl-cycloalkyl), or heterocycly (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with

 (leading to a spiro structure) or with =O.

A ring system is a system consisting of at least one ring of connected atoms but including also systems in which two or more rings of connected atoms are joined with "joined" meaning that the respective rings are sharing one (like a spiro structure), two or more atoms being a member or members of both joined rings.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic—especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with NH$_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Any compound that is a N-oxide of a compound according to the invention like a compound according to general formula I defined above is understood to be also covered by the scope of the invention.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon or of a nitrogen by $^{15}$N-enriched nitrogen are within the scope of this invention. This would especially also apply to the provisos described above so that any mentioning of hydrogen or any "H" in a formula would also cover deuterium or tritium.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general Formula (I)

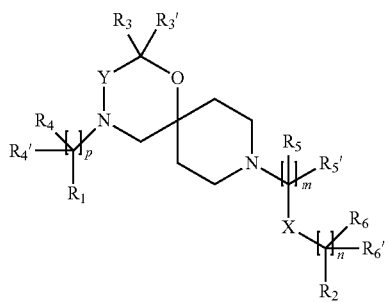

(I)

is a compound wherein
p is 0 or 1;
m is 1, 2 or 3;
n is 0, 1 or 2;
Y is —CH$_2$— or —C(O)—;
X is a bond, —C(R$_x$R$_{x'}$)—, —C(O)— or —O—;
wherein R$_x$ is selected from halogen, substituted or unsubstituted C$_{1-6}$ alkyl, substituted or unsubstituted C$_{2-6}$ alkenyl substituted or unsubstituted C$_{2-6}$ alkynyl, and —OR$_8$;

R$_{x'}$ is selected from hydrogen, halogen of substituted or substituted C$_{1-6}$ alkyl, substituted or unsubstituted C$_{2-6}$ alkenyl and substituted or unsubstituted C$_{2-6}$ alkynyl;

R$_8$ is selected from hydrogen, substituted or unsubstituted C$_{1-6}$ alkyl, substituted or unsubstituted C$_{2-6}$ alkenyl and substituted or unsubstituted C$_{2-6}$ alkynyl;

R$_1$ is selected from substituted or unsubstituted C$_{1-6}$ alkyl, substituted or unsubstituted C$_{2-6}$ alkenyl, substituted or unsubstituted C$_{2-6}$ alkynyl and substituted or unsubstituted cycloalkyl;
  wherein said cycloalkyl in R$_1$ if substituted, is substituted with one or more substituent/s selected from halogen —R$_{11}$, —OR$_{11}$, —NO$_2$, —NR$_{11}$R$_{11'''}$, NR$_{11}$C(O)R$_{11'}$, —NR$_{11}$S(O)R$_{11'}$, —S(O)$_2$NR$_{11}$R$_{11'}$, —NR$_{11}$C(O)NR$_{11'}$R$_{11''}$, —SR$_{11}$, —S(O)R$_{11}$, S(O)$_2$R$_{11}$, —CN, haloalkyl, haloalkoxy, —C(O)OR$_{11}$, —C(O)NR$_{11}$R$_{11'}$, —OCH$_2$CH$_2$OH, —NR$_{11}$S(O)$_2$NR$_{11'}$R$_{11''}$ and C(CH$_3$)$_2$OR$_{11}$;
  additionally, cycloalkyl in R$_1$ if substituted, may also be substituted with 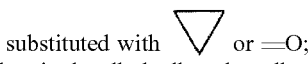 or =O;
  wherein the alkyl, alkenyl or alkynyl in R$_1$, if substituted, is substituted with one or more substituent/s selected from —OR$_{11}$, halogen, —CN, haloalkyl, haloalkoxy and —NR$_{11}$R$_{11'''}$;
  wherein R$_{11}$, R$_{11'}$ ad R$_{11''}$ are independently selected from hydrogen, unsubstituted C$_{1-6}$ alkyl, unsubstituted C$_{2-6}$ alkenyl and unsubstituted C$_{2-6}$ alkynyl;
  and wherein R$_{11'''}$ is selected from hydrogen, unsubstituted C$_{1-6}$ alkyl, unsubstituted C$_{2-6}$ alkenyl, unsubstituted C$_{2-6}$ alkynyl and -Boc;

R$_2$ is selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl,
  wherein said cycloalkyl, aryl or heterocyclyl in R$_2$, if substituted, is substituted with one or more substituent/s selected from halogen, —R$_{12}$, —OR$_{12}$, —NO$_2$, —NR$_{12}$R$_{12'''}$, NR$_{12}$C(O)R$_{12'}$, —NR$_{12}$S(O)$_2$R$_{12'}$, —S(O)$_2$NR$_{12}$R$_{12'}$, —NR$_{12}$C(O)NR$_{12'}$N$_{12''}$, —SR$_{12}$, —S(O)R$_{12}$, S(O)$_2$R$_{12}$, —CN, haloalkyl, haloalkoxy, —C(O)OR$_{12}$, —C(O)NR$_{12}$R$_{12'}$, —OCH$_2$CH$_2$OH, —NR$_{12}$S(O)$_2$NR$_{12'}$R$_{12''}$ and C(CH$_3$)$_2$OR$_{12}$;
  additionally, cycloalkyl or non-aromatic heterocyclyl in R$_2$, if substituted, may also be substituted with 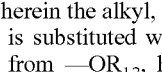 or =O;
  wherein the alkyl, alkenyl or alkynyl in R$_2$, if substituted, is substituted with one or more substituent/s selected from —OR$_{12}$, halogen, —CN, haloalkyl, haloalkoxy and —NR$_{12}$R$_{12'''}$;
  wherein R$_{12}$, R$_{12'}$ and R$_{12''}$ are independently selected from hydrogen, unsubstituted C$_{1-6}$ alkyl, unsubstituted C$_{2-6}$ alkenyl and unsubstituted C$_{2-6}$ alkynyl;
  and wherein R$_{12'''}$ is selected from hydrogen, unsubstituted C$_{1-6}$ alkyl, unsubstituted C$_{2-6}$ alkenyl, unsubstituted C$_{2-6}$ alkynyl and -Boc;

R$_3$ and R$_{3'}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl;
alternatively, R$_3$ and R$_{3'}$, taken together with the connecting C-atom may form a substituted or unsubstituted cycloalkyl;

$R_4$ and $R_{4'}$ are independently selected from hydrogen, substituted or unsubstituted $C_{1-9}$ alkyl, substituted or unsubstituted $C_{2-9}$ alkenyl and substituted or unsubstituted $C_{2-9}$ alkynyl, —CHOR$_9$ and —C(O)OR$_9$;
  wherein $R_9$ is selected from hydrogen, substituted or unsubstituted $C_{1-9}$ alkyl, substituted or unsubstituted $C_{2-9}$ alkenyl and substituted or unsubstituted $C_{2-9}$ alkynyl;
$R_5$ and $R_{5'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl, —CHOR$_7$ and —C(O)OR$_7$;
  wherein $R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
  alternatively, $R_5$ and $R_{5'}$ taken together with the connecting C-atom may form a substituted or unsubstituted cycloalkyl or a substituted or unsubstituted non-aromatic heterocyclyl;
$R_6$ and $R_{6'}$ are independently selected from hydrogen, substituted or unsubstituted $C_{1-6}$ alkyl, substituted or unsubstituted $C_{2-6}$ alkenyl, and substituted or unsubstituted $C_{2-6}$ alkynyl, —OR$_{10}$, —CHOR$_{10}$ and —C(O)OR$_{10}$;
  wherein $R_{10}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
the alkyl, alkenyl or alkynyl, other than those defined in $R_1$ or $R_2$, if substituted, is substituted with one or more substituent/s selected from —OR$_{13}$, halogen, —CN, haloalkyl, haloalkoxy and —NR$_{13}$R$_{13'''}$;
  wherein $R_{13}$ is selected from hydrogen, unsubstituted $C_{1-6}$ alkyl, unsubstituted $C_{2-6}$ alkenyl and unsubstituted $C_{2-6}$ alkynyl;
  $R_{13'''}$ is selected from hydrogen, unsubstituted $C_{1-6}$ alkyl, unsubstituted $C_{2-6}$ alkenyl, and unsubstituted $C_{2-6}$ alkynyl and -Boc;
the aryl, heterocyclyl or cycloalkyl other than those defined in $R_1$ or $R_2$, if substituted, is substituted with one or more substituent/s selected from halogen, —R$_{14}$, —OR$_{14}$, —NO$_2$, —NR$_{14}$R$_{14'''}$, NR$_{14}$C(O)R$_{14'}$, —NR$_{14}$S(O)$_2$R$_{14'}$, —S(O)$_2$NR$_{14}$R$_{14'}$, —NR$_{14}$C(O)NR$_{14'}$R$_{14'''}$, —SR$_{14}$, —S(O)R$_{14}$, S(O)$_2$R$_{14}$, —CN, haloalkyl, haloalkoxy, —C(O)OR$_{14}$, —C(O)NR$_{14}$R$_{14'}$, —OCH$_2$CH$_2$OH, —NR$_{14}$S(O)$_2$NR$_{14'}$R$_{14'''}$ and C(CH$_3$)$_2$OR$_{14}$;
  additionally, wherein cycloalkyl or non-aromatic heterocyclyl, other than those defined in $R_1$ or $R_2$, if substituted, may also be substituted with  or =O;
    wherein $R_{14}$, $R_{14'}$ and $R_{14'''}$ are independently selected from hydrogen, unsubstituted $C_{1-6}$ alkyl, unsubstituted $C_{2-6}$ alkenyl, and unsubstituted $C_{2-6}$ alkynyl, unsubstituted aryl, unsubstituted cycloalkyl and unsubstituted heterocyclyl;
    and wherein $R_{14'''}$ is selected from hydrogen, unsubstituted $C_{1-6}$ alkyl, unsubstituted $C_{2-6}$ alkenyl, and unsubstituted $C_{2-6}$ alkynyl and -Boc;
These preferred compounds according to the invention are optionally in form of one of the stereoisomers, preferably enantiomers or diastereomers, a racemate or in form a mixture of at least two of the stereoisomers, preferably enantiomer and/or diastereomers, in any mixing ratio, or a corresponding salt thereof, or a corresponding solvate thereof.

In a further embodiment the compound according to the invention of general Formula (I) is a compound wherein
  m is 1, 2 or 3;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
  n is 0, 1 or 2;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein
  p is 0 or 1;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
  X is a bond, —C(R$_x$R$_{x'}$), —C(O)— or —O—;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
  X is a bond;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
  X is —C(R$_x$R$_{x'}$)—;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
  X is —O—;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is —C(O)—:

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein Y is —$CH_2$— or —C(O)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein Y is —$CH_2$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein Y is —C(O)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention general Formula (I) is a compound wherein $R_1$ is selected from substituted or unsubstituted $C_{1-6}$ alkyl, substituted or unsubstituted $C_{2-6}$ alkenyl, substituted or unsubstituted $C_{2-6}$ alkynyl and substituted or unsubstituted cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from substituted or unsubstituted $C_{1-6}$ alkyl and substituted or unsubstituted cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl and substituted or unsubstituted heterocyclyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from hydrogen, substituted or unsubstituted $C_{1-6}$ alkyl, substituted or unsubstituted aryl and substituted or unsubstituted heterocyclyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from hydrogen, substituted or unsubstituted $C_{1-6}$ alkyl, substituted or unsubstituted cycloalkyl, substituted or unsubstituted aryl and substituted or unsubstituted heterocyclyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_3$ and $R_{3'}$ are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_3$ and $R_{3'}$, taken together with the connecting C-atom form a substituted or unsubstituted cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ and $R_{4'}$ are independently selected from hydrogen, substituted or unsubstituted $C_{1-9}$ alkyl, substituted or unsubstituted $C_{2-9}$ alkenyl and substituted or unsubstituted $C_{2-9}$ alkynyl, —$CHOR_9$ and —$C(O)OR_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ and $R_{4'}$ are independently selected from hydrogen, substituted or unsubstituted $C_{1-9}$ alkyl, substituted or unsubstituted $C_{2-9}$ alkenyl and substituted or unsubstituted $C_{2-9}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ and $R_{4'}$ are independently selected from hydrogen and substituted or unsubstituted $C_{1-9}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$CHOR_7$ and —$C(O)OR_7$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ and $R_{5'}$ taken together with the connecting C-atom form a substituted or unsubstituted cycloalkyl or a substituted or unsubstituted non-aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ and $R_{5'}$ taken together with the connecting C-atom form a substituted or unsubstituted cycloalkyl or a substituted or unsubstituted non-aromatic heterocyclyl, m is 1, X is a bond, n is 0 and $R_2$ is hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ and $R_{5'}$ taken together with the connecting C-atom form a substituted or unsubstituted cycloalkyl or a substituted or unsubstituted saturated heterocyclyl, m is 1, X is a bond, n is 0 and $R_2$ is hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$OR_{10}$, —$CHOR_{10}$ and —$C(O)OR_{10}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_9$ is selected from hydrogen, substituted or unsubstituted $C_{1-9}$ alkyl, substituted or unsubstituted $C_{2-9}$ alkenyl and substituted or unsubstituted $C_{2-9}$ alkynyl; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{10}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers a racemate or in form of a mixture of at least two of the stereoisomers, preferably enantiomers and/or diastereomers, in any mixing ratio, or a salt thereof, or a corresponding solvate thereof.

In another preferred embodiment of the compound according to the invention of general Formula (I) is a compound wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is compound wherein $R_{12}$, $R_{12'}$ and $R_{12''}$ independently selected from hydrogen, unsubstituted $C_{1-6}$ alkyl, unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$ is selected from hydrogen, unsubstituted $C_{1-6}$ alkyl, unsubstituted $C_{2-6}$ alkenyl, and unsubstituted $C_{2-6}$ alkynyl;

$R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$ is selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from halogen, substituted or unsubstituted $C_{1-6}$ alkyl, substituted or unsubstituted $C_{2-6}$ alkenyl substituted or unsubstituted $C_{2-6}$ alkynyl, and —$OR_8$;

$R_{x'}$ is selected from hydrogen, halogen or substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from halogen, substituted or unsubstituted $C_{1-6}$ alkyl, substituted or unsubstituted $C_{2-6}$ alkenyl substituted or unsubstituted $C_{2-6}$ alkynyl, and —$OR_8$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{x'}$ is selected from hydrogen, halogen or substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I), is a compound wherein p is 0 or 1;
m is 1, 2 or 3;
n is 0, 1 or 2;
Y is —$CH_2$— or —C(O)—;
X is a bond, —$C(R_xR_{x'})$—, —C(O)— or —O—;
$R_1$ is selected from substituted or unsubstituted $C_{1-6}$ alkyl, substituted or unsubstituted $C_{2-6}$ alkenyl, substituted or unsubstituted $C_{2-6}$ alkynyl and substituted or unsubstituted cycloalkyl;

wherein the $C_{1-6}$ alkyl is preferably selected from methyl, ethyl, propyl, butyl, pentyl, hexyl, isopropyl and 2-methylpropyl; more preferably the $C_{1-6}$ alkyl is methyl, ethyl, propyl, isopropyl, isobutyl, sec-butyl, isopentyl or neopentyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; preferably the cycloalkyl is cyclopropyl;

and/or $R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, wherein the $C_{1-6}$ alkyl is preferably selected from methyl, ethyl, propyl, butyl, pentyl, hexyl, isopropyl and 2-methylpropyl; more preferably the $C_{1-6}$ alkyl is methyl, ethyl, propyl, isopropyl, isobutyl, tert-butyl or neopentyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or the aryl is selected from phenyl, naphtyl, or anthracene; preferably is napthyl or phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; more preferably is pyridine;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; preferably the cycloalkyl is cyclopropyl;

and/or $R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl; preferably is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_3$ and $R_{3'}$, taken together with the connecting C-atom may form a substituted or unsubstituted cycloalkyl;

wherein the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

and/or $R_4$ and $R_{4'}$ are independently selected from hydrogen, substituted or unsubstituted $C_{1-9}$ alkyl, substituted or unsubstituted $C_{2-9}$ alkenyl, substituted or unsubstituted $C_{2-9}$ alkynyl, —CHOR$_9$ and —C(O)OR$_9$;

wherein the $C_{1-6}$ alkyl is preferably selected from methyl, ethyl, propyl, butyl, pentyl, hexyl, isopropyl and 2-methylpropyl; preferably is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR$_7$ and —C(O)OR$_7$;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_5$ and $R_{5'}$ taken together with the connecting C-atom may form a substituted or unsubstituted cycloalkyl or a substituted or unsubstituted non-aromatic heterocyclyl;

wherein the non-aromatic heterocyclyl is a heterocyclic ring system of one or more saturated or unsaturated rings of which at least one ring contains one or more heteroatoms from the group consisting of nitrogen, oxygen and/or sulfur in the ring; preferably is a non-aromatic heterocyclic ring system of one or two saturated or unsaturated rings of which at least one ring contains one or more heteroatoms from the group consisting of nitrogen, oxygen and/or sulfur in the ring, more preferably is selected from piperidine, piperazine, tetrahydropyrane, morpholine, oxopyrrolidine; preferably, the non-aromatic heterocyclyl is tetrahydropyrane;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably is cyclobutyl, cyclopentyl or cyclohexyl;

and/or $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$OR_{10}$, —$CHOR_{10}$ and —$C(O)OR_{10}$;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_7$ selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_9$ selected from hydrogen, substituted or unsubstituted $C_{1-9}$ alkyl, substituted or unsubstituted $C_{2-9}$ alkenyl and substituted or unsubstituted $C_{2-9}$ alkynyl;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{10}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl preferably selected from ethylene, propylene, butylene, pentylene and hexylene;

and/or the $C_{2-6}$-alkynyl is preferably selected from ethyne, propyne, butyne, pentyne and hexyne, and/or $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

$R_{11'''}$ is selected from hydrogen, unsubstituted $C_{1-6}$ alkyl, unsubstituted $C_{2-6}$ alkenyl and unsubstituted $C_{2-6}$ alkynyl and -Boc;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

$R_{12'''}$ is selected from hydrogen, unsubstituted $C_{1-6}$ alkyl, unsubstituted $C_{2-6}$ alkenyl and unsubstituted $C_{2-6}$ alkynyl and -Boc;

wherein the $C_{1-6}$ alkyl is preferably selected from methyl, ethyl, propyl, butyl, pentyl, hexyl, isopropyl and 2-methylpropyl; preferably the $C_{1-6}$ alkyl is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{13}$ is selected from hydrogen, unsubstituted $C_{1-6}$ alkyl, unsubstituted $C_{2-6}$ alkenyl, and unsubstituted $C_{2-6}$ alkynyl;

$R_{13'''}$ is selected from hydrogen, unsubstituted $C_{1-6}$ alkyl, unsubstituted $C_{2-6}$ alkenyl and unsubstituted $C_{2-6}$ alkynyl and -Boc;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

$R_{14'''}$ is selected from hydrogen, unsubstituted $C_{1-6}$ alkyl, unsubstituted $C_{2-6}$ alkenyl, unsubstituted $C_{2-6}$ alkynyl and -Boc;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl and anthracene; preferably is napthyl or phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
$R_x$ is selected from halogen, substituted or unsubstituted $C_{1-6}$ alkyl, substituted or unsubstituted $C_{2-6}$ alkenyl substituted or unsubstituted $C_{2-6}$ alkynyl, and —$OR_8$—;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_{x'}$ is selected from hydrogen, halogen or substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_1$ as defined in any of the embodiments of the present invention,
the $C_{1-6}$ alkyl is preferably selected from methyl, ethyl, propyl, butyl, pentyl, hexyl, isopropyl and 2-methylpropyl; more preferably the $C_{1-6}$ alkyl is methyl, ethyl, propyl, isopropyl, isobutyl, sec-butyl, isopentyl or neopentyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; preferably the cycloalkyl is cyclopropyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_2$ as defined in any of the embodiments of the present invention,
the $C_{1-6}$ alkyl is preferably selected from methyl, ethyl, propyl, butyl, pentyl, hexyl, isopropyl and 2-methylpropyl; more preferably the $C_{1-6}$ alkyl is methyl, ethyl, propyl, isopropyl, isobutyl, tert-butyl or neopentyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl, or anthracene; preferably is napthyl or phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; preferably is pyridine;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; preferably the cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_3$ and $R_{3'}$ as defined in any of the embodiments of the present invention, the $C_{1-6}$ alkyl is preferably selected from methyl, ethyl, propyl, butyl, pentyl, hexyl, isopropyl and 2-methylpropyl; more preferably is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_4$ and $R_{4'}$ as defined in any of the embodiments of the present invention, the $C_{1-6}$ alkyl is preferably selected from methyl, ethyl, propyl, butyl, pentyl, hexyl, isopropyl and 2-methylpropyl; more preferably is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_5$ and $R_{5'}$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or the non-aromatic heterocyclyl is a heterocyclic ring system of one or more saturated or unsaturated rings of which at least one ring contains one or more heteroatoms from the group consisting of nitrogen, oxygen and/or sulfur in the ring; preferably is a non-aromatic heterocyclic ring system of one or two saturated or unsaturated rings of which at least one ring contains one or more heteroatoms from the group consisting of nitrogen, oxygen and/or sulfur in the ring, more preferably is selected from piperidine, piperazine, tetrahydropyrane, morpholine, oxopyrrolidine; preferably, the non-aromatic heterocyclyl is tetrahydropyrane;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably is cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_6$ and $R_{6'}$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_7$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_8$ as defined in any of the embodiments of the present invention, the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_9$ as defined in any of the embodiments of the present invention, the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{10}$ as defined in any of the embodiments of the present invention, the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11}$, $R_{11'}$ and $R_{11''}$ as defined in any of the embodiments of the present invention, the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11'''}$ as defined in any of the embodiments of the present invention.

the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12}$, $R_{12'}$ and $R_{12''}$ as defined in any of the embodiments of the present invention, the $C_{1-6}$ alkyl is preferably selected from methyl, ethyl, propyl, butyl, pentyl, hexyl, isopropyl and 2-methylpropyl; preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12'''}$ as defined in any of the embodiments of the present invention, the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13}$ and $R_{13'''}$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14}$, $R_{14'}$ and $R_{14''}$ as defined in any of the embodiments of the present invention.

the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or the aryl is selected from phenyl, naphtyl and anthracene; preferably is napthyl or phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14'''}$ as defined in any of the embodiments of the present invention.

the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_x$ as defined in any of the embodiments of the present invention.

the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{x'}$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{1-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein n is 0, 1 or 2; preferably, n is 0;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 1, 2 or 3; preferably m is 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein p is 0 or 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein p is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein X is a bond, —C($R_x R_{x'}$)—, —C(O)— or —O—; preferably, X is a bond or —O—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein Y is —CH$_2$— or —C(O)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein X is a bond, —C($R_x R_{x'}$)—, —C(O)— or —O—; preferably X is a bond or —O— and/or m is 1, 2 or 3; preferably m is 1 or 2; and/or n is 0, 1 or 2; preferably n is 0; and/or p is 0 or 1; preferably p is 0;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I), the compound is a compound of Formula (I')

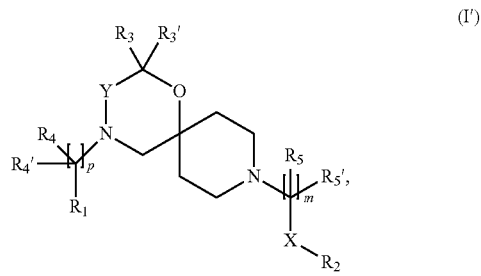

(I')

wherein $R_1$, $R_2$, $R_3$, $R_{3'}$, $R_4$, $R_{4'}$, $R_5$, $R_{5'}$, X, Y, m and p are as described above or as described below.

In another preferred embodiment of the invention according to general Formula (I), the compound is a compound of Formula (I')

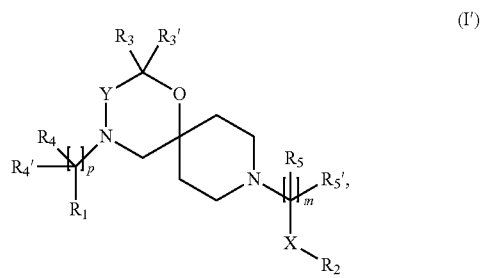

(I')

wherein
p is 0 or 1;
m is 1, 2 or 3;
V is —CH$_2$— or —C(O)—;
X is a bond, —C($R_x R_{x'}$)—, —C(O)— or —O—;
wherein $R_x$ is selected from halogen, substituted or unsubstituted $C_{1-6}$ alkyl, substituted or unsubstituted $C_{2-6}$ alkenyl substituted or unsubstituted $C_{2-6}$ alkynyl, and —OR$_8$;
$R_{x'}$ is selected from hydrogen, halogen or substituted or unsubstituted $C_{1-6}$ alkyl, substituted or unsubstituted $C_{2-6}$ alkenyl and substituted or unsubstituted $C_{2-6}$ alkynyl;
$R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_1$ is selected from substituted or unsubstituted $C_{1-6}$ alkyl, substituted or unsubstituted $C_{2-6}$ alkenyl, substituted or unsubstituted $C_{2-6}$ alkynyl and substituted or unsubstituted cycloalkyl;
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
$R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
alternatively, $R_3$ and $R_{3'}$, taken together with the connecting C-atom may form a substituted or unsubstituted cycloalkyl;
$R_4$ and $R_{4'}$ are independently selected from hydrogen, substituted or unsubstituted $C_{1-9}$ alkyl, substituted or unsubstituted $C_{2-9}$ alkenyl, substituted or unsubstituted $C_{2-9}$ alkynyl, —CHOR$_9$ and —C(O)OR$_9$;
  wherein R$_9$ is selected from hydrogen, substituted or unsubstituted $C_{1-9}$ alkyl, substituted or unsubstituted $C_{2-9}$ alkenyl and substituted or unsubstituted $C_{2-9}$ alkynyl;
R$_5$ and R$_{5'}$ are independently selected from hydrogen substituted or unsubstituted $C_{1-6}$ alkyl, substituted or unsubstituted $C_{2-6}$ alkenyl, substituted or unsubstituted $C_{2-6}$ alkynyl, —CHOR$_7$ and —C(O)OR$_7$.
  wherein R$_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl; alternatively, R$_5$ and R$_{5'}$ taken together with the connecting C-atom may form a substituted or unsubstituted cycloalkyl or a substituted or unsubstituted non-aromatic heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I), the compound is a compound of Formula (I$^{a'}$)

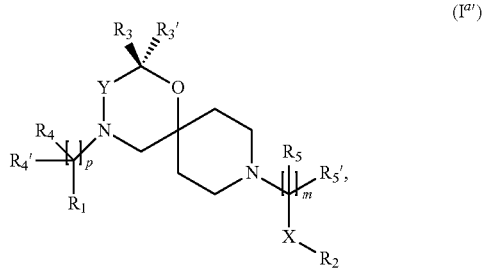

(I$^{a'}$)

wherein
p is 0 or 1',
m is 1, 2 or 3;
Y is —CH$_2$— or —C(O)—;
X is a bond, —C(R$_x$R$_{x'}$)—, —C(O)— or —O—;
  wherein R$_x$ is selected from halogen, substituted or unsubstituted $C_{1-6}$ alkyl, substituted or unsubstituted $C_{2-6}$ alkenyl substituted or unsubstituted $C_{2-6}$ alkynyl, and —OR$_8$;
R$_{x'}$ is selected from hydrogen, halogen or substituted or unsubstituted $C_{1-6}$ alkyl, substituted or unsubstituted $C_{2-6}$ alkenyl and substituted or unsubstituted $C_{2-6}$ alkynyl;
R$_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
R$_1$ is selected from substituted or unsubstituted $C_{1-6}$ alkyl, substituted or unsubstituted $C_{2-6}$ alkenyl, substituted or unsubstituted $C_{2-6}$ alkynyl and substituted or unsubstituted cycloalkyl;
R$_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, R$_3$ and R$_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
alternatively, R$_3$ and R$_{3'}$, taken together with the connecting C-atom may form a substituted or unsubstituted cycloalkyl;
R$_4$ and R$_{4'}$ are independently selected from hydrogen, substituted or unsubstituted $C_{1-9}$ alkyl, substituted or unsubstituted $C_{2-9}$ alkenyl, substituted or unsubstituted $C_{2-9}$ alkynyl, —CHOR$_9$ and —C(O)OR$_9$;
  wherein R$_9$ is selected from hydrogen, substituted or unsubstituted $C_{1-9}$ alkyl, substituted or unsubstituted $C_{2-9}$ alkenyl and substituted or unsubstituted $C_{2-9}$ alkynyl;
R$_5$ and R$_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR$_7$ and —C(O)OR$_7$;
  wherein R$_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
alternatively, R$_5$ and R$_{5'}$ taken together with the connecting C-atom may form a substituted or unsubstituted cycloalkyl or a substituted or unsubstituted non-aromatic heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I), the compound is a compound of Formula (I$^{b'}$)

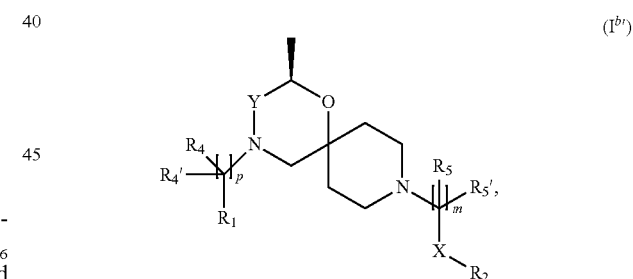

(I$^{b'}$)

wherein
p is 0 or 1;
m is 1, 2 or 3;
V is —CH$_2$— or —C(O)—;
X is a bond, —C(R$_x$R$_{x'}$)—, —C(O)— or —O—;
  wherein R$_x$ is selected from halogen, substituted or unsubstituted $C_{1-6}$ alkyl, substituted or unsubstituted $C_{2-6}$ alkenyl substituted or unsubstituted $C_{2-6}$ alkynyl, and —OR$_8$;
R$_{x'}$ is selected from hydrogen, halogen or substituted or unsubstituted $C_{1-6}$ alkyl, substituted or unsubstituted $C_{2-6}$ alkenyl and substituted or unsubstituted $C_{2-6}$ alkynyl;
R$_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_1$ is selected from substituted or unsubstituted $C_{1-6}$ alkyl, substituted or unsubstituted $C_{2-6}$ alkenyl, substituted or unsubstituted $C_{2-6}$ alkynyl and substituted or unsubstituted cycloalkyl;

$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, $R_4$ and $R_{4'}$ are independently selected from hydrogen, substituted or unsubstituted $C_{1-9}$ alkyl, substituted or unsubstituted $C_{2-9}$ alkenyl, substituted or unsubstituted $C_{2-9}$ alkynyl, —CHOR$_9$ and —C(O)OR$_9$;
   wherein $R_9$ is selected from hydrogen, substituted or unsubstituted $C_{1-9}$ alkyl, substituted or unsubstituted $C_{2-9}$ alkenyl and substituted or unsubstituted $C_{2-9}$ alkynyl;

$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR$_7$ and —C(O)OR$_7$;
   wherein $R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
   alternatively, $R_5$ and $R_{5'}$ taken together with the connecting C-atom may form a substituted or unsubstituted cycloalkyl or a substituted or unsubstituted non-aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I), the compound is a compound of Formula (I$^{c'}$)

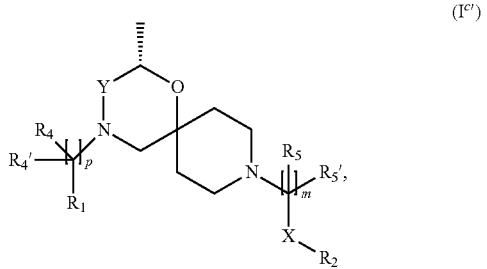

wherein
   p is 0 or 1;
   m is 1, 2 or 3;
   Y is —CH$_2$— or —C(O)—;
   X is a bond, —C(R$_x$R$_{x'}$)—, —C(O)— or —O—;
   wherein R$_x$ is selected from halogen, substituted or unsubstituted $C_{1-6}$ alkyl, substituted or unsubstituted $C_{2-6}$ alkenyl substituted or unsubstituted $C_{2-6}$ alkynyl, and —OR$_8$;
   R$_{x'}$ is selected from hydrogen, halogen or substituted or unsubstituted $C_{1-6}$ alkyl, substituted or unsubstituted $C_{2-6}$ alkenyl and substituted or unsubstituted $C_{2-6}$ alkynyl;

$R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_1$ is selected from substituted or unsubstituted $C_{1-6}$ alkyl, substituted or unsubstituted $C_{2-6}$ alkenyl, substituted or unsubstituted $C_{2-6}$ alkynyl and substituted or unsubstituted cycloalkyl;

$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, $R_4$ and $R_{4'}$ are independently selected from hydrogen, substituted or unsubstituted $C_{1-9}$ alkyl, substituted or unsubstituted $C_{2-9}$ alkenyl, substituted or unsubstituted $C_{2-9}$ alkynyl, —CHOR$_9$ and —C(O)OR$_9$;
   wherein $R_9$ is selected from hydrogen, substituted or unsubstituted $C_{1-9}$ alkyl, substituted or unsubstituted $C_{2-9}$ alkenyl and substituted or unsubstituted $C_{2-9}$ alkynyl;

$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR$_7$ and —C(O)OR$_7$;
   wherein $R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
   alternatively, $R_5$ and $R_{5'}$ taken together with the connecting C-atom may form a substituted or unsubstituted cycloalkyl or a substituted or unsubstituted non-aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I$^{2'}$),

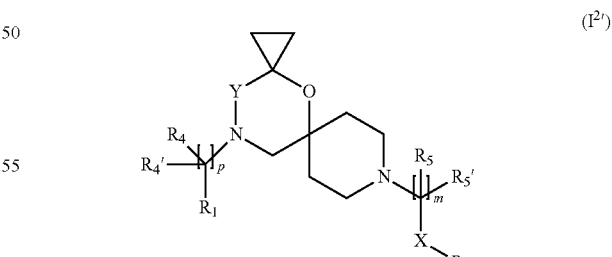

wherein $R_1$, $R_2$, $R_4$, $R_{4'}$, $R_5$, $R_{5'}$, X, Y, m and p are as described above or as described below.

In a further preferred embodiment of the invention according to general Formula (I) the compound is a compound of Formula (I$^{2'}$),

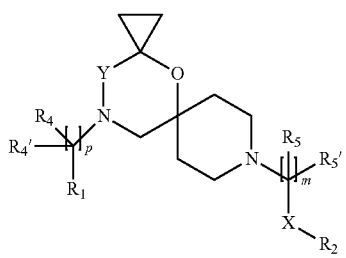

(I²')

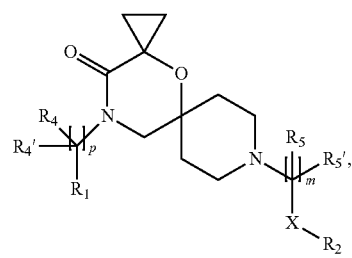

(I³')

wherein
p is 0 or 1;
m is 1, 2 or 3;
Y is —CH₂— or —C(O)—;
X is a bond, —C(R$_x$R$_{x'}$)—, —C(O)— or —O—;
wherein R$_x$ is selected from halogen, substituted or unsubstituted C$_{1-6}$ alkyl, substituted or unsubstituted C$_{2-6}$ alkenyl substituted or unsubstituted C$_{2-6}$ alkynyl, and —OR$_8$;
R$_{x'}$ is selected from hydrogen, halogen or substituted or unsubstituted C$_{1-6}$ alkyl, substituted or unsubstituted C$_{2-6}$ alkenyl and substituted or unsubstituted C$_{2-6}$ alkynyl;
R$_8$ is selected from hydrogen, substituted or unsubstituted C$_{1-6}$ alkyl, substituted or unsubstituted C$_{2-6}$ alkenyl and substituted or unsubstituted C$_{2-6}$ alkynyl;
R$_1$ is selected from substituted or unsubstituted C$_{1-6}$ alkyl, substituted or unsubstituted C$_{2-6}$ alkenyl, substituted or unsubstituted C$_{2-6}$ alkynyl and substituted or unsubstituted cycloalkyl;
R$_2$ is selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl,
R$_4$ and R$_{4'}$ are independently selected from hydrogen, substituted or unsubstituted C$_{1-9}$ alkyl, substituted or unsubstituted C$_{2-9}$ alkenyl, substituted or unsubstituted C$_{2-9}$ alkynyl, —CHOR$_9$ and —C(O)OR$_9$;
wherein R$_9$ is selected from hydrogen, substituted or unsubstituted C$_{1-9}$ alkyl, substituted or unsubstituted C$_{2-9}$ alkenyl and substituted or unsubstituted C$_{2-9}$ alkynyl;
R$_5$ and R$_{5'}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl, —CHOR$_7$ and —C(O)OR$_7$;
wherein R$_7$ is selected from hydrogen, substituted or unsubstituted C$_{1-6}$ alkyl, substituted or unsubstituted C$_{2-6}$ alkenyl and substituted or unsubstituted C$_{2-6}$ alkynyl;
alternatively, R$_5$ and R$_{5'}$ taken together with the connecting C-atom may form a substituted or unsubstituted cycloalkyl or a substituted or unsubstituted non-aromatic heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I³'), wherein R$_1$, R$_2$, R$_4$, R$_{4'}$, R$_5$, R$_{5'}$, X, Y, m and p are as described above or as described below.

In a further preferred embodiment of the invention according to general Formula (I) the compound is a compound of Formula (I³'),

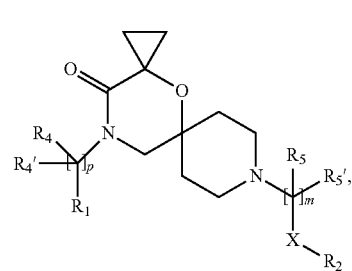

(I³')

wherein
p is 0 or 1;
m is 1, 2 or 3;
X is a bond, —C(R$_x$R$_{x'}$)—, —C(O)— or —O—;
wherein R$_x$ is selected from halogen, substituted or unsubstituted C$_{1-6}$ alkyl, substituted or unsubstituted C$_{2-6}$ alkenyl substituted or unsubstituted C$_{2-6}$ alkynyl, and —OR$_8$;
R$_{x'}$ is selected from hydrogen, halogen or substituted or unsubstituted C$_{1-6}$ alkyl, substituted or unsubstituted C$_{2-6}$ alkenyl and substituted or unsubstituted C$_{2-6}$ alkynyl;
R$_8$ is selected from hydrogen, substituted or unsubstituted C$_{1-6}$ alkyl, substituted or unsubstituted C$_{2-6}$ alkenyl and substituted or unsubstituted C$_{2-6}$ alkynyl;
R$_1$ is selected from substituted or unsubstituted C$_{1-6}$ alkyl, substituted or unsubstituted C$_{2-6}$ alkenyl, substituted or unsubstituted C$_{2-6}$ alkynyl and substituted or unsubstituted cycloalkyl;
R$_2$ is selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl,
R$_4$ and R$_{4'}$ are independently selected from hydrogen, substituted or unsubstituted C$_{1-9}$ alkyl, substituted or unsubstituted C$_{2-9}$ alkenyl, substituted or unsubstituted C$_{2-9}$ alkynyl, —CHOR$_9$ and —C(O)OR$_9$;
wherein R$_9$ is selected from hydrogen, substituted or unsubstituted C$_{1-9}$ alkyl, substituted or unsubstituted C$_{2-9}$ alkenyl and substituted or unsubstituted C$_{2-9}$ alkynyl;
R$_5$ and R$_{5'}$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, —CHOR$_7$ and —C(O)OR$_7$;
wherein R$_7$ is selected from hydrogen, substituted or unsubstituted C$_{1-6}$ alkyl, substituted or unsubstituted C$_{2-6}$ alkenyl and substituted or unsubstituted C$_{2-6}$ alkynyl;
alternatively, R$_5$ and R$_{5'}$ taken together with the connecting C-atom may form a substituted or unsubstituted cycloalkyl or a substituted or unsubstituted non-aromatic heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I$^{4'}$).

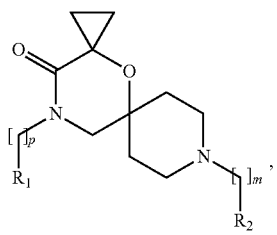

wherein R$_1$, R$_2$, m and p are as described above or as described below.

In a further preferred embodiment of the invention according to general Formula (I) the compound is a compound of Formula (I$^{4'}$),

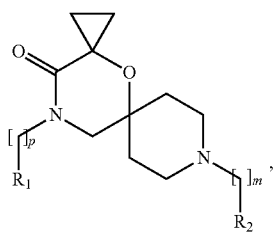

wherein
p is 0 or 1;
m is 1, 2 or 3;
R$_1$ is selected from substituted or unsubstituted C$_{1-6}$ alkyl, substituted or unsubstituted C$_{2-6}$ alkenyl, substituted or unsubstituted C$_{2-6}$ alkynyl and substituted or unsubstituted cycloalkyl;
R$_2$ is selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I$^{5'}$),

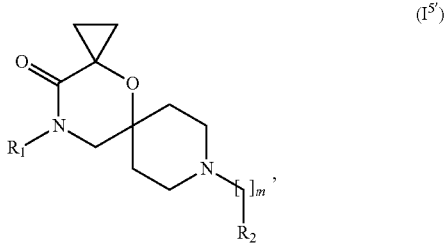

wherein
m is 1, 2 or 3;
R$_1$ is selected from substituted or unsubstituted C$_{1-6}$ alkyl, substituted or unsubstituted C$_{2-6}$ alkenyl, substituted or unsubstituted C$_{2-6}$ alkynyl and substituted or unsubstituted cycloalkyl;
R$_2$ is selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl,
optionally in form of one of the stereoisomers, preferably enantiomers or diastereomers, a racemate or in form of a mixture of at least two of the stereoisomers, preferably enantiomers and/or diastereomers in any mixing ratio, or a corresponding salt thereof, or a corresponding solvate thereof.

In another preferred embodiment of the invention according to general Formula (I), the compound is a compound of Formula (I$^{6'}$)

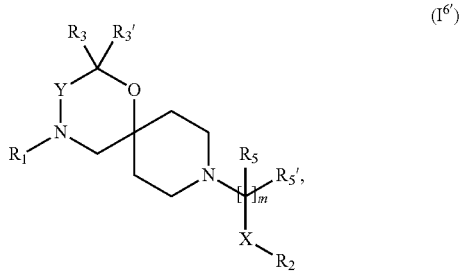

wherein
m is 1, 2 or 3;
Y is —CH$_2$— or —C(O)—;
X is a bond, —C(R$_x$R$_{x'}$)—, —C(O)— or —O—;

wherein $R_x$ is selected from halogen, substituted or unsubstituted $C_{1-6}$ alkyl, substituted or unsubstituted $C_{2-6}$ alkenyl substituted or unsubstituted $C_{2-6}$ alkynyl, and —$OR_8$;

$R_{x'}$ is selected from hydrogen, halogen or substituted or unsubstituted $C_{1-6}$ alkyl, substituted or unsubstituted $C_{2-6}$ alkenyl and substituted or unsubstituted $C_{2-6}$ alkynyl;

$R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_1$ is selected from substituted or unsubstituted $C_{1-6}$ alkyl, substituted or unsubstituted $C_{2-6}$ alkenyl, substituted or unsubstituted $C_{2-6}$ alkynyl and substituted or unsubstituted cycloalkyl;

$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, $R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively, $R_3$ and $R_{3'}$, taken together with the connecting C-atom may form a substituted or unsubstituted cycloalkyl;

$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$CHOR_7$ and —$C(O)OR_7$;

wherein $R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively, $R_5$ and $R_{5'}$ taken together with the connecting C-atom may form a substituted or unsubstituted cycloalkyl or a substituted or unsubstituted non-aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment
$R_1$ is a substituted or unsubstituted group selected from methyl, ethyl, propyl, isopropyl, isobutyl, sec-butyl, isopentyl, neo-pentyl and cyclopropyl.

In a preferred embodiment
$R_1$ is an unsubstituted group selected from methyl, ethyl, propyl, isopropyl, isobutyl, sec-butyl, isopentyl, neo-pentyl and cyclopropyl.

In a preferred embodiment
$R_1$ is a substituted or unsubstituted cyclopropyl, preferably unsubstituted cyclopropyl.

In a preferred embodiment
$R_2$ is hydrogen or a substituted or unsubstituted group selected from methyl, ethyl, propyl, isopropyl, isobutyl, tert-butyl, neo-pentyl, cyclopropyl, phenyl and pyridine; more preferably hydrogen or an unsubstituted group selected from methyl, ethyl, propyl, isopropyl, isobutyl, tert-butyl, neo-pentyl, cyclopropyl, or a substituted or unsubstituted group selected from phenyl and pyridine.

In a preferred embodiment
$R_3$ and $R_{3'}$ taken together with the connecting C-atom may form a substituted or unsubstituted cyclopropyl: preferably unsubstituted cyclopropyl.

In a preferred embodiment
$R_3$ is hydrogen or substituted or unsubstituted methyl, preferably $R_3$ is hydrogen or unsubstituted methyl.

In a preferred embodiment
$R_{3'}$ is hydrogen or substituted or unsubstituted methyl, preferably $R_{3'}$ is hydrogen or unsubstituted methyl.

In a preferred embodiment
$R_{3'}$ is hydrogen while $R_3$ is substituted or unsubstituted methyl, preferably $R_{3'}$ is hydrogen while $R_3$ is unsubstituted methyl.

In a preferred embodiment
$R_3$ is hydrogen while $R_{3'}$ is substituted or unsubstituted methyl, preferably $R_3$ is hydrogen while $R_{3'}$ is unsubstituted methyl.

In a preferred embodiment
$R_3$ and $R_{3'}$ are both substituted or unsubstituted methyl, preferably $R_3$ and $R_{3'}$ are both unsubstituted methyl.

In a preferred embodiment
$R_3$ and $R_{3'}$ are both hydrogen.

In a preferred embodiment
$R_4$ is hydrogen or substituted or unsubstituted methyl, preferably $R_4$ is hydrogen or unsubstituted methyl.

In a preferred embodiment
$R_{4'}$ is hydrogen.

In a preferred embodiment
$R_{4'}$ is hydrogen while $R_4$ is substituted or unsubstituted methyl, preferably $R_{4'}$ is hydrogen while $R_4$ is unsubstituted methyl.

In a preferred embodiment
$R_4$ and $R_{4'}$ are both hydrogen.

In a preferred embodiment
$R_5$ and $R_{5'}$ are both hydrogen.

In a preferred embodiment
$R_5$ and $R_{5'}$ taken together with the connecting C-atom form a substituted or unsubstituted group selected from cyclobutyl, cyclopentyl, cyclohexyl or tetrahydropyrane, preferably an unsubstituted group selected from cyclobutyl, cyclopentyl, cyclohexyl or tetrahydropyrane.

In a preferred embodiment
$R_6$ and $R_{6'}$ are both hydrogen.

In a preferred embodiment
X is a bond.

In a preferred embodiment
X is —O—.

In a preferred embodiment
Y is —$CH_2$—;

In a preferred embodiment
Y is —C(O)—;

In another preferred embodiment
n is 0.

In another preferred embodiment
n is 1.

In another preferred embodiment
n is 2.

In another preferred embodiment
m is 1 or 2;

In another preferred embodiment
p is 0, 1 or 2.

In another preferred embodiment
p is 0 or 1.

In another preferred embodiment
p is 0.

In an particular embodiment
the halogen is fluorine or chlorine.

In a preferred further embodiment, the compounds of the general Formula (I) are selected from

| EXAMPLE | Structure | CHEMICAL NAME |
|---|---|---|
| 1 | 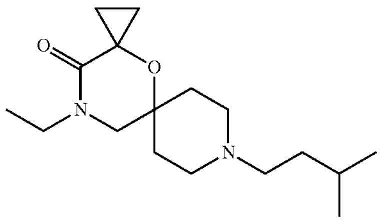 [SMILES: CCN1CC2(CCN(CCC(C)C)CC2)OC2(CC2)C1=O] | 12-ethyl-8-isopentyl-4-oxa-8,12-diazadispiro[2.1.5.3]tridecan-13-one |
| 2 | 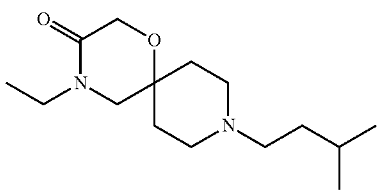 [SMILES: CCN1CC2(CCN(CCC(C)C)CC2)OCC1=O] | 4-ethyl-9-isopentyl-1-oxa-4,9-diazaspiro[5.5]undecan-3-one |
| 3 | 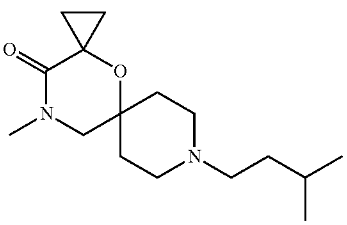 [SMILES: CC(C)CCN1CCC2(CC1)CN(C)C(=O)C1(CC1)O2] | 8-isopentyl-12-methyl-4-oxa-8,12-diazadispiro[2.1.5.3]tridecan-13-one |
| 4 | 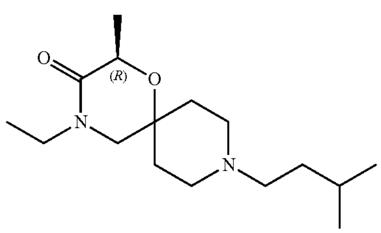 | (R)-4-ethyl-9-isopentyl-2-methyl-1-oxa-4,9-diazaspiro[5.5]undecan-3-one |
| 5 | 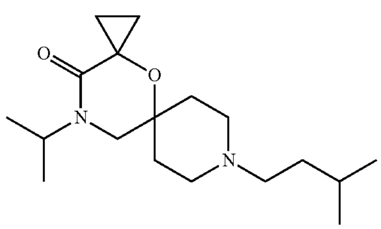 [SMILES: CC(C)CCN1CCC2(CC1)CN(C(C)C)C(=O)C1(CC1)O2] | 8-isopentyl-12-isopropyl-4-oxa-8,12-diazadispiro[2.1.5.3]tridecan-13-one |
| 6 | 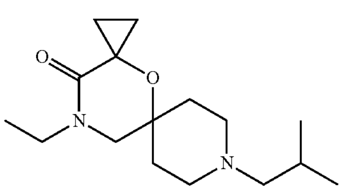 [SMILES: CCN1CC2(CCN(CC(C)C)CC2)OC2(CC2)C1=O] | 12-ethyl-8-isobutyl-4-oxa-8,12-diazadispiro[2.1.5.3]tridecan-13-one |
| 7 | 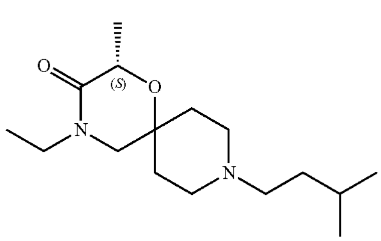 | (S)-4-ethyl-9-isopentyl-2-methyl-1-oxa-4,9-diazaspiro[5.5]undecan-3-one |

| EXAMPLE | Structure | CHEMICAL NAME |
| --- | --- | --- |
| 8 | 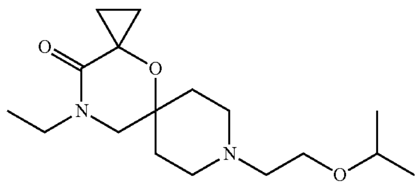 [SMILES: CCN1CC2(CCN(CCOC(C)C)CC2)OC2(CC2)C1=O] | 12-ethyl-8-(2-isopropoxyethyl)-4-oxa-8,12-diazadispiro[2.1.5.3]tridecan-13-one |
| 9 | 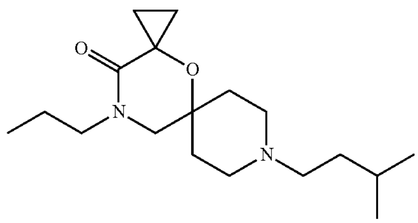 [SMILES: CCCN1CC2(CCN(CCC(C)C)CC2)OC2(CC2)C1=O] | 8-isopentyl-12-propyl-4-oxa-8,12-diazadispiro[2.1.5.3]tridecan-13-one |
| 10 | 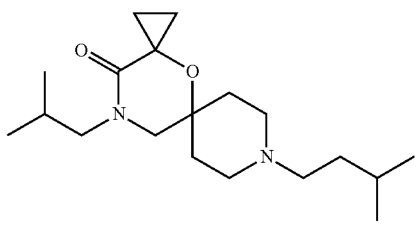 [SMILES: CC(C)CCN1CCC2(CC1)CN(CC(C)C)C(=O)C1(CC1)O2] | 12-isobutyl-8-isopentyl-4-oxa-8,12-diazadispiro[2.1.5.3]tridecan-13-one |
| 11 | 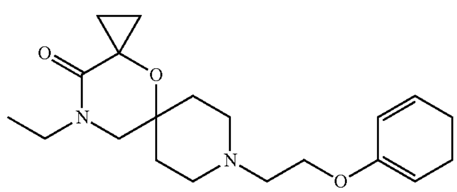 [SMILES: CCN1CC2(CCN(CCOC3=CCCC=C3)CC2)OC2(CC2)C1=O] | 12-ethyl-8-(2-phenoxyethyl)-4-oxa-8,12-diazadispiro[2.1.5.3]tridecan-13-one |
| 12 | 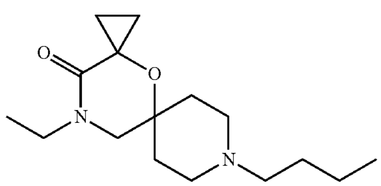 [SMILES: CCCCN1CCC2(CC1)CN(CC)C(=O)C1(CC1)O2] | 8-butyl-12-ethyl-4-oxa-8,12-diazadispiro[2.1.5.3]tridecan-13-one |
| 13 | 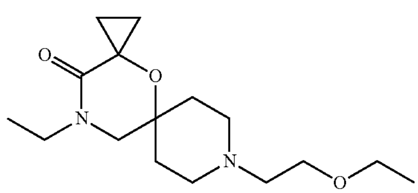 [SMILES: CCOCCN1CCC2(CC1)CN(CC)C(=O)C1(CC1)O2] | 8-(2-ethoxyethyl)-12-ethyl-4-oxa-8,12-diazadispiro[2.1.5.3]tridecan-13-one |
| 14 | 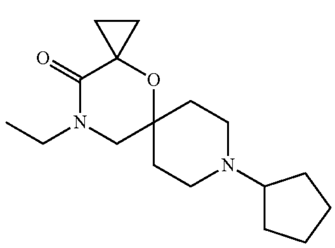 [SMILES: CCN1CC2(CCN(C3CCCC3)CC2)OC2(CC2)C1=O] | 8-cyclopentyl-12-ethyl-4-oxa-8,12-diazadispiro[2.1.5.3]tridecan-13-one |

| EXAMPLE | Structure | CHEMICAL NAME |
| --- | --- | --- |
| 15 | 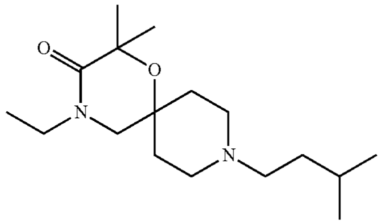 [SMILES: CCN1CC2(CCN(CCC(C)C)CC2)OC(C)(C)C1=O] | 4-ethyl-9-isopentyl-2,2-dimethyl-1-oxa-4,9-diazaspiro[5.5]undecan-3-one |
| 16 | 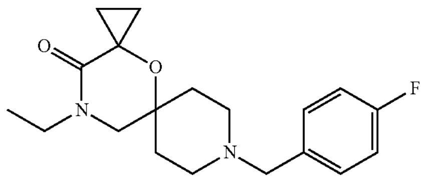 [SMILES: CCN1CC2(CCN(Cc3ccc(F)cc3)CC2)OC2(CC2)C1=O] | 12-ethyl-8-(4-fluorobenzyl)-4-oxa-8,12-diazadispiro[2.1.5.3]tridecan-13-one |
| 17 | 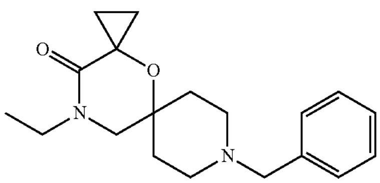 [SMILES: CCN1CC2(CCN(Cc3ccccc3)CC2)OC2(CC2)C1=O] | 8-benzyl-12-ethyl-4-oxa-8,12-diazadispiro[2.1.5.3]tridecan-13-one |
| 18 | 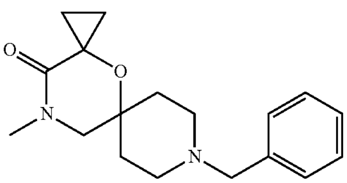 [SMILES: CN1CC2(CCN(Cc3ccccc3)CC2)OC2(CC2)C1=O] | 8-benzyl-12-methyl-4-oxa-8,12-diazadispiro[2.1.5.3]tridecan-13-one |
| 19 | 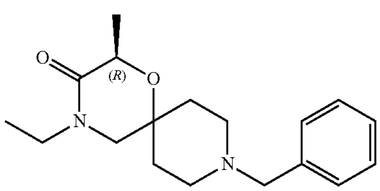 | (R)-9-benzyl-4-ethyl-2-methyl-1-oxa-4,9-diazaspiro[5.5]undecan-3-one |
| 20 | 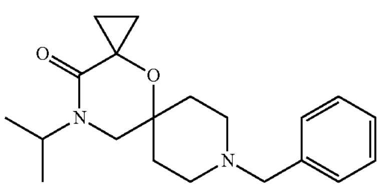 [SMILES: CC(C)N1CC2(CCN(Cc3ccccc3)CC2)OC2(CC2)C1=O] | 8-benzyl-12-isopropyl-4-oxa-8,12-diazadispiro[2.1.5.3]tridecan-13-one |
| 21 | 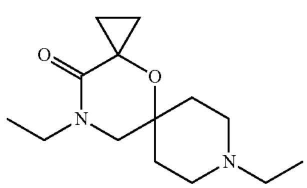 [SMILES: CCN1CCC2(CC1)CN(CC)C(=O)C1(CC1)O2] | 8,12-diethyl-4-oxa-8,12-diazadispiro[2.1.5.3]tridecan-13-one |
| 22 | 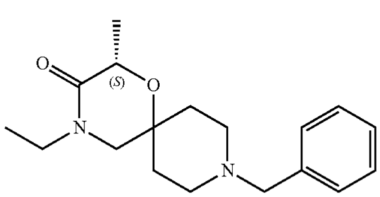 | (S)-9-benzyl-4-ethyl-2-methyl-1-oxa-4,9-diazaspiro[5.5]undecan-3-one |

| EXAMPLE | Structure | CHEMICAL NAME |
|---|---|---|
| 23 | 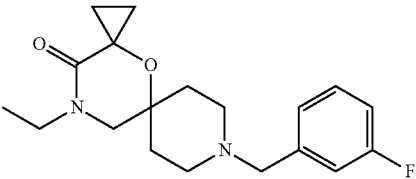 [SMILES: CCN1CC2(CCN(Cc3cccc(F)c3)CC2)OC2(CC2)C1=O] | 12-ethyl-8-(3-fluorobenzyl)-4-oxa-8,12-diazadispiro[2.1.5.3]tridecan-13-one |
| 24 | 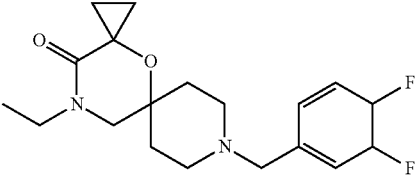 [SMILES: CCN1CC2(CCN(CC3=CC(F)C(F)C=C3)CC2)OC2(CC2)C1=O] | 8-(3,4-difluorobenzyl)-12-ethyl-4-oxa-8,12-diazadispiro[2.1.5.3]tridecan-13-one |
| 25 | 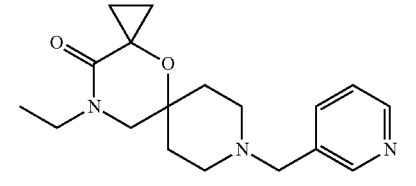 | 12-ethyl-8-(pyridin-3-ylmethyl)-4-oxa-8,12-diazadispiro[2.1.5.3]tridecan-13-one |
| 26 | 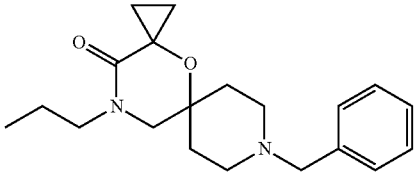 [SMILES: CCCN1CC2(CCN(Cc3ccccc3)CC2)OC2(CC2)C1=O] | 8-benzyl-12-propyl-4-oxa-8,12-diazadispiro[2.1.5.3]tridecan-13-one |
| 27 | 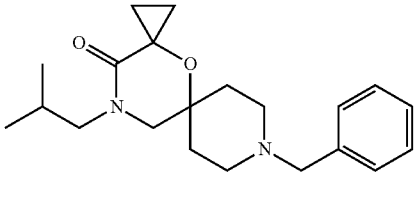 [SMILES: CC(C)CN1CC2(CCN(Cc3ccccc3)CC2)OC2(CC2)C1=O] | 8-benzyl-12-isobutyl-4-oxa-8,12-diazadispiro[2.1.5.3]tridecan-13-one |
| 28 | 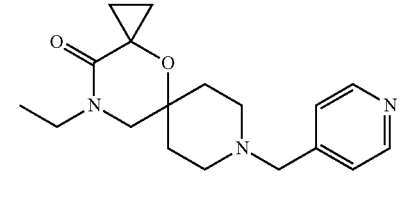 [SMILES: CCN1CC2(CCN(Cc3ccncc3)CC2)OC2(CC2)C1=O] | 12-ethyl-8-(pyridin-4-ylmethyl)-4-oxa-8,12-diazadispiro[2.1.5.3]tridecan-13-one |
| 29 | 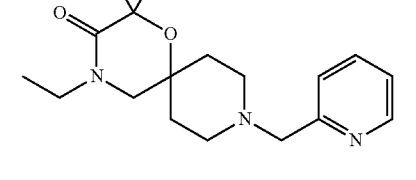 | 12-ethyl-8-(pyridin-2-ylmethyl)-4-oxa-8,12-diazadispiro[2.1.5.3]tridecan-13-one |
| 30 | 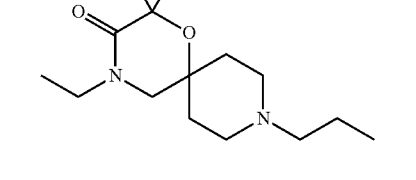 | 12-ethyl-8-propyl-4-oxa-8,12-diazadispiro[2.1.5.3]tridecan-13-one |

-continued

| EXAMPLE | Structure | CHEMICAL NAME |
|---|---|---|
| 31 | 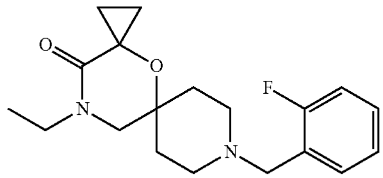 [SMILES: CCN1CC2(CCN(Cc3ccccc3F)CC2)OC2(CC2)C1=O] | 12-ethyl-8-(2-fluorobenzyl)-4-oxa-8,12-diazadispiro[2.1.5.3]tridecan-13-one |
| 32 | 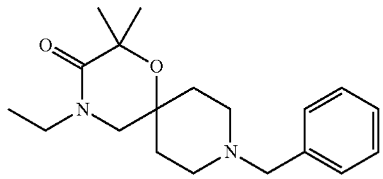 [SMILES: CCN1CC2(CCN(Cc3ccccc3)CC2)OC(C)(C)C1=O] | 9-benzyl-4-ethyl-2,2-dimethyl-1-oxa-4,9-diazaspiro[5.5]undecan-3-one |
| 33 | 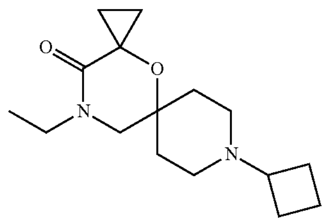 [SMILES: CCN1CC2(CCN(C3CCC3)CC2)OC2(CC2)C1=O] | 8-cyclobutyl-12-ethyl-4-oxa-8,12-diazadispiro[2.1.5.3]tridecan-13-one |
| 34 | 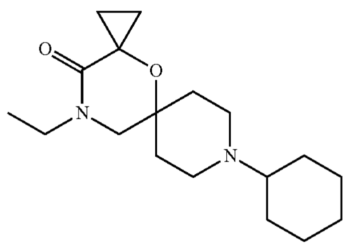 [SMILES: CCN1CC2(CCN(C3CCCCC3)CC2)OC2(CC2)C1=O] | 8-cyclohexyl-12-ethyl-4-oxa-8,12-diazadispiro[2.1.5.3]tridecan-13-one |
| 35 | 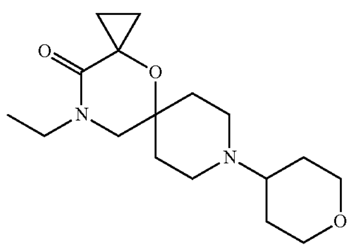 [SMILES: CCN1CC2(CCN(C3CCOCC3)CC2)OC2(CC2)C1=O] | 12-ethyl-8-(tetrahydro-2H-pyran-4-yl)-4-oxa-8,12-diazadispiro[2.1.5.3]tridecan-13-one |
| 36 | 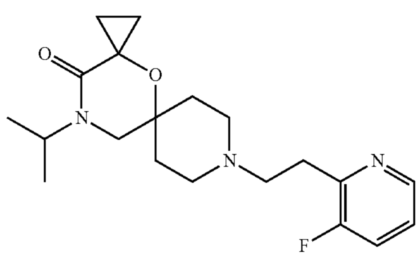 [SMILES: CC(C)N1CC2(CCN(CCc3ncccc3F)CC2)OC2(CC2)C1=O] | 8-(2-(3-fluoropyridin-2-yl)ethyl)-12-isopropyl-4-oxa-8,12-diazadispiro[2.1.5.3]tridecane |
| 37 | 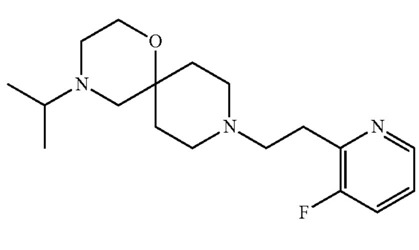 [SMILES: CC(C)N1CCOC2(CCN(CCc3ncccc3F)CC2)C1] | 9-(2-(3-fluoropyridin-2-yl)ethyl)-4-isopropyl-1-oxa-4,9-diazaspiro[5.5]undecane |

| EXAMPLE | Structure | CHEMICAL NAME |
|---|---|---|
| 38 | 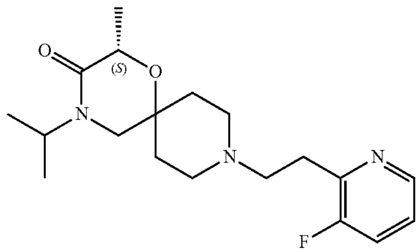 | (S)-9-(2-(3-fluoropyridin-2-yl)ethyl)-4-isopropyl-2-methyl-1-oxa-4,9-diazaspiro[5.5]undecane |
| 39 | 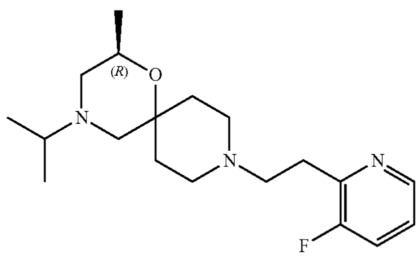 | (R)-9-(2-(3-fluoropyridin-2-yl)ethyl)-4-isopropyl-2-methyl-1-oxa-4,9-diazaspiro[5.5]undecane |
| 40 | 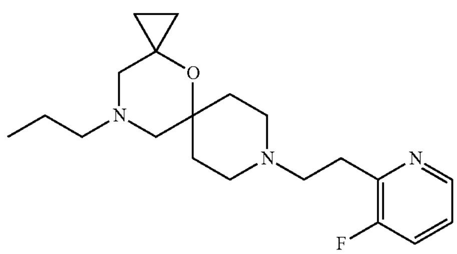 [SMILES: CCCN1CC2(CCN(CCc3ncccc3F)CC2)OC2(CC2)C1] | 8-(2-(3-fluoropyridin-2-yl)ethyl)-12-propyl-4-oxa-8,12-diazadispiro[2.1.5.3]tridecane |
| 41 | 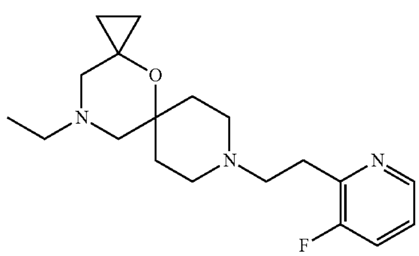 [SMILES: CCN1CC2(CCN(CCc3ncccc3F)CC2)OC2(CC2)C1] | 12-ethyl-8-(2-(3-fluoropyridin-2-yl)ethyl)-4-oxa-8,12-diazadispiro[2.1.5.3]tridecane |
| 42 | 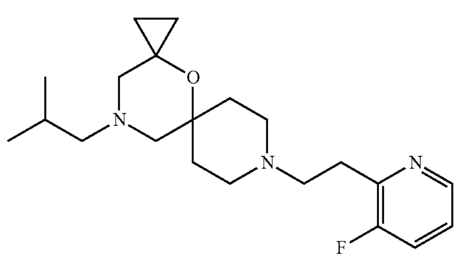 [SMILES: CC(C)CN1CC2(CCN(CCc3ncccc3F)CC2)OC2(CC2)C1] | 8-(2-(3-fluoropyridin-2-yl)ethyl)-12-isobutyl-4-oxa-8,12-diazadispiro[2.1.5.3]tridecane |
| 43 | | 8-(2-(3-fluoropyridin-2-yl)ethyl)-12-methyl-4-oxa-8,12-diazadispiro[2.1.5.3]tridecane | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred further embodiment, the compounds of the general Formula (I) are selected from

| EXAMPLE | Structure | CHEMICAL NAME |
|---|---|---|
| 44 | 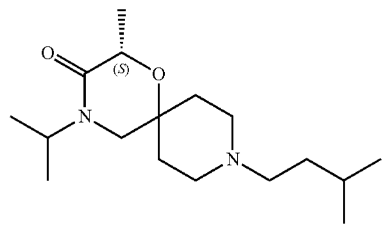 | (S)-9-isopentyl-4-isopropyl-2-methyl-1-oxa-4,9-diazaspiro[5.5]undecan-3-one |
| 45 | 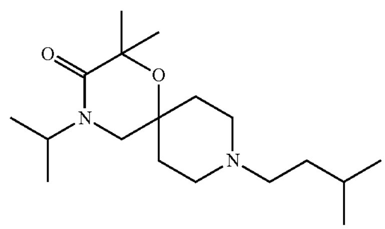 [SMILES: CC(C)CCN1CCC2(CC1)CN(C(C)C)C(=O)C(C)(C)O2] | 9-isopentyl-4-isopropyl-2,2-dimethyl-1-oxa-4,9-diazaspiro[5.5]undecan-3-one |
| 46 | 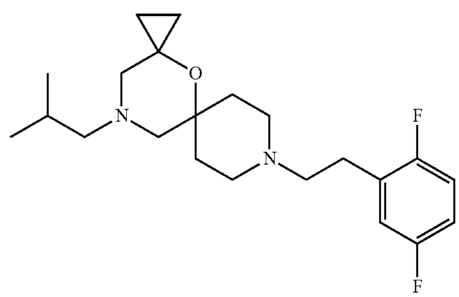 [SMILES: CC(C)CN1CC2(CCN(CCc3cc(F)ccc3F)CC2)OC2(CC2)C1] | 8-(2,5-difluorophenethyl)-12-isobutyl-4-oxa-8,12-diazadispiro[2.1.5.3]tridecane |
| 47 | 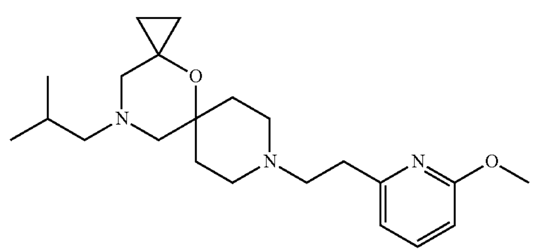 [SMILES: COc1cccc(CCN2CCC3(CC2)CN(CC(C)C)CC2(CC2)O3)n1] | 12-isobutyl-8-(2-(6-methoxypyridin-2-yl)ethyl)-4-oxa-8,12-diazadispiro[2.1.5.3]tridecane |
| 48 | 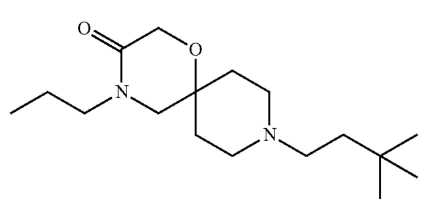 [SMILES: CCCN1CC2(CCN(CCC(C)(C)C)CC2)OCC1=O] | 9-(3,3-dimethylbutyl)-4-propyl-1-oxa-4,9-diazaspiro[5.5]undecan-3-one |
| 49 | 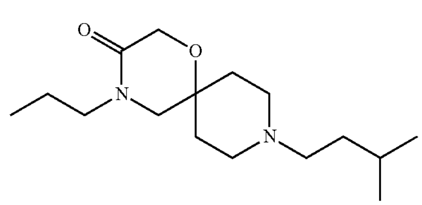 [SMILES: CCCN1CC2(CCN(CCC(C)C)CC2)OCC1=O] | 9-isopentyl-4-propyl-1-oxa-4,9-diazaspiro[5.5]undecan-3-one |

-continued

| EXAMPLE | Structure | CHEMICAL NAME |
|---|---|---|
| 50 | 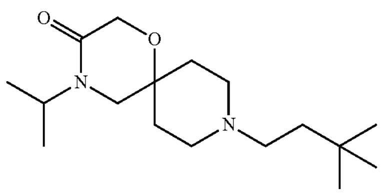 [SMILES: CC(C)N1CC2(CCN(CCC(C)(C)C)CC2)OCC1=O] | 9-(3,3-dimethylbutyl)-4-isopropyl-1-oxa-4,9-diazaspiro[5.5]undecan-3-one |
| 51 | 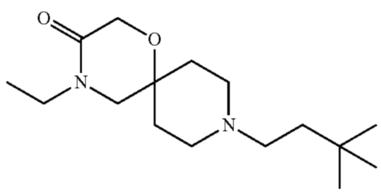 [SMILES: CCN1CC2(CCN(CCC(C)(C)C)CC2)OCC1=O] | 9-(3,3-dimethylbutyl)-4-ethyl-1-oxa-4,9-diazaspiro[5.5]undecan-3-one |
| 52 | 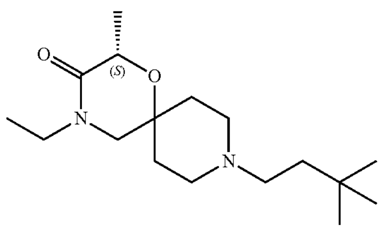 | (S)-9-(3,3-dimethylbutyl)-4-ethyl-2-methyl-1-oxa-4,9-diazaspiro[5.5]undecan-3-one |
| 53 | 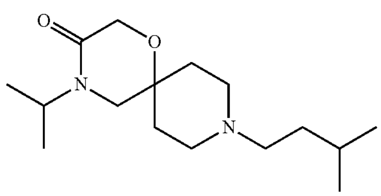 [SMILES: CC(C)CCN1CCC2(CC1)CN(C(C)C)C(=O)CO2] | 9-isopentyl-4-isopropyl-1-oxa-4,9-diazaspiro[5.5]undecan-3-one |
| 54 | 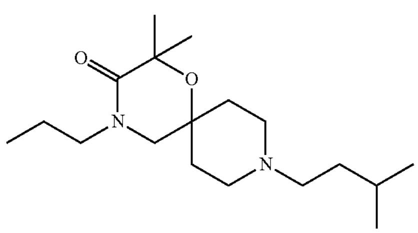 [SMILES: CCCN1CC2(CCN(CCC(C)C)CC2)OC(C)(C)C1=O] | 9-isopentyl-2,2-dimethyl-4-propyl-1-oxo-4,9-diazaspiro[5.5]undecan-3-one |
| 55 | 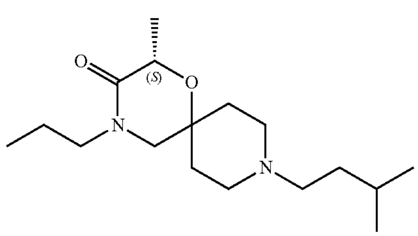 | (S)-9-isopentyl-2-methyl-4-propyl-1-oxa-4,9-diazaspiro[5.5]undecan-3-one |
| 56 | 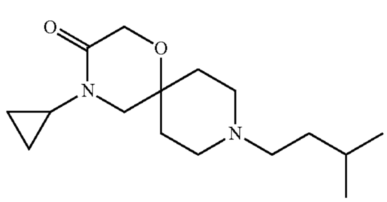 [SMILES: CC(C)CCN1CCC2(CC1)CN(C1CC1)C(=O)CO2] | 4-cyclopropyl-9-isopentyl-1-oxa-4,9-diazaspiro[5.5]undecan-3-one |

| EXAMPLE | Structure | CHEMICAL NAME |
|---|---|---|
| 57 | 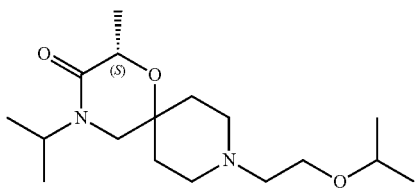 | (S)-9-(2-isopropoxyethyl)-4-isopropyl-2-methyl-1-oxa-4,9-diazaspiro[5.5]undecan-3-one |
| 58 | 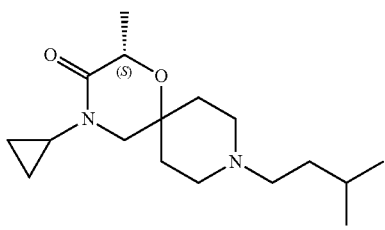 | (S)-4-cyclopropyl-9-isopentyl-2-methyl-1-oxa-4,9-diazaspiro[5.5]undecan-3-one |
| 59 | 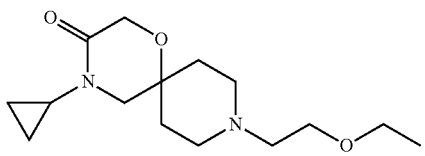 [SMILES: CCOCCN1CCC2(CC1)CN(C1CC1)C(=O)CO2] | 4-cyclopropyl-9-(2-isopropoxyethyl)-1-oxa-4,9-diazaspiro[5.5]undecan-3-one |
| 60 | 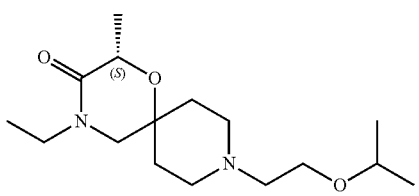 | (S)-4-ethyl-9-(2-isopropoxyethyl)-2-methyl-1-oxa-4,9-diazaspiro[5.5]undecan-3-one |
| 61 | 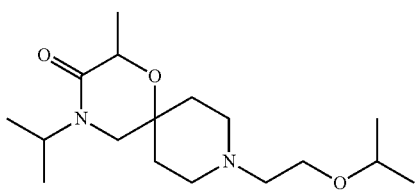 [SMILES: CC(C)OCCN1CCC2(CC1)CN(C(C)C)C(=O)C(C)O2] | 9-(2-isopropoxyethyl)-4-isopropyl-2-methyl-1-oxa-4,9-diazaspiro[5.5]undecan-3-one |
| 62 | 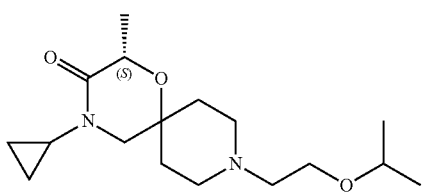 | (S)-4-cyclopropyl-9-(2-isopropoxyethyl)-2-methyl-1-oxa-4,9-diazaspiro[5.5]undecan-3-one |
| 63 | 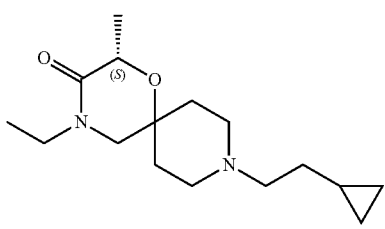 | (S)-9-(2-cyclopropylethyl)-4-ethyl-2-methyl-1-oxa-4,9-diazaspiro[5.5]undecan-3-one |

-continued

| EXAMPLE | Structure | CHEMICAL NAME |
|---|---|---|
| 64 | 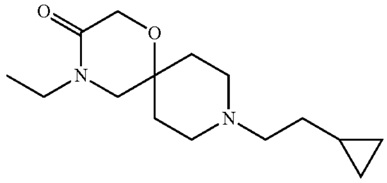 [SMILES: CCN1CC2(CCN(CCC3CC3)CC2)OCC1=O] | 9-(2-cyclopropylethyl)-4-ethyl-1-oxa-4,9-diazaspiro[5.5]undecan-3-one |
| 65 | 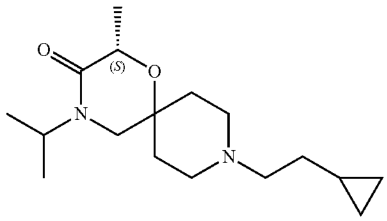 | (S)-9-(2-cyclopropylethyl)-4-isopropyl-2-methyl-1-oxa-4,9-diazaspiro[5.5]undecan-3-one |
| 66 | 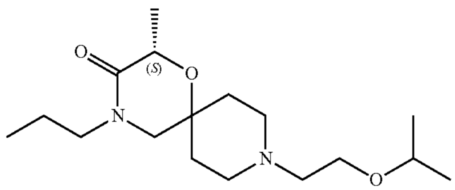 | (S)-9-(2-isopropoxyethyl)-2-methyl-4-propyl-1-oxa-4,9-diazaspiro[5.5]undecan-3-one |
| 67 | 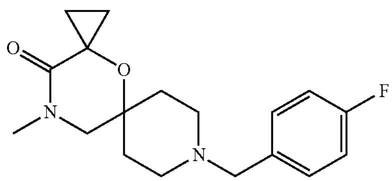 [SMILES: CN1CC2(CCN(Cc3ccc(F)cc3)CC2)OC2(CC2)C1=O] | 8-(4-fluorobenzyl)-12-methyl-4-oxa-8,12-diazadispiro[2.1.5.3]tridecan-13-one |
| 68 | 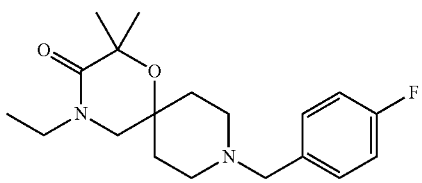 [SMILES: CCN1CC2(CCN(Cc3ccc(F)cc3)CC2)OC(C)(C)C1=O] | 4-ethyl-9-(4-fluorobenzyl)-2,2-dimethyl-1-oxa-4,9-diazaspiro[5.5]undecan-3-one |
| 69 | 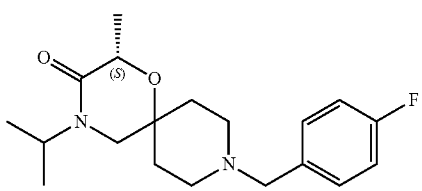 | (S)-9-(4-fluorobenzyl)-4-isopropyl-2-methyl-1-oxo-4,9-diazaspiro[5.5]undecan-3-one |
| 70 | 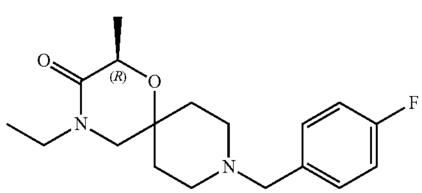 | (R)-4-ethyl-9-(4-fluorobenzyl)-2-methyl-1-oxa-4,9-diazaspiro[5.5]undecan-3-one |
| 71 | 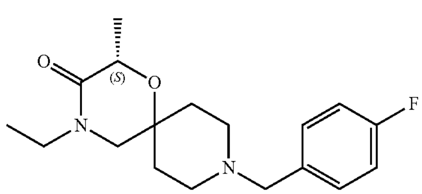 | (S)-4-ethyl-9-(4-fluorobenzyl)-2-methyl-1-oxa-4,9-diazaspiro[5.5]undecan-3-one |

| EXAMPLE | CHEMICAL NAME |
|---------|---------------|
| 72 | (S)-9-(4-chlorobenzyl)-4-ethyl-2-methyl-1-oxa-4,9-diazaspiro[5.5]undecan-3-one |
| 73 | (R)-9-(4-chlorobenzyl)-4-ethyl-2-methyl-1-oxa-4,9-diazaspiro[5.5]undecan-3-one |
| 74 | (R)-4-((4-ethyl-2-methyl-3-oxo-1-oxa-4,9-diazaspiro[5.5]undecan-9-yl)methyl)benzonitrile |
| 75 | (R)-4-ethyl-9-(4-methoxybenzyl)-2-methyl-1-oxa-4,9-diazaspiro[5.5]undecan-3-one |
| 76 | 9-(4-chlorobenzyl)-4-ethyl-2,2-dimethyl-1-oxa-4,9-diazaspiro[5.5]undecan-3-one |
| 77 | 4-((4-ethyl-2,2-dimethyl-3-oxo-1-oxa-4,9-diazaspiro[5.5]undecan-9-yl)methyl)benzonitrile |
| 78 | 4-ethyl-9-(4-methoxybenzyl)-2,2-dimethyl-1-oxa-4,9-diazaspiro[5.5]undecan-3-one |
| 79 | (S)-4-ethyl-2-methy-9-neopentyl-1-oxa-4,9-diazaspiro[5.5]undecan-3-one |

-continued

| EXAMPLE | Structure | CHEMICAL NAME |
|---|---|---|
| 80 | 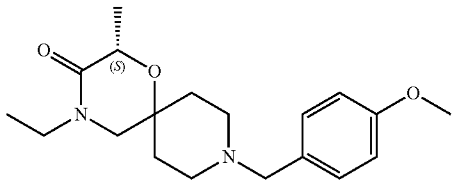 | (S)-4-ethyl-9-(4-methoxybenzyl)-2-methyl-1-oxa-4,9-diazaspiro[5.5]undecan-3-one |
| 81 | 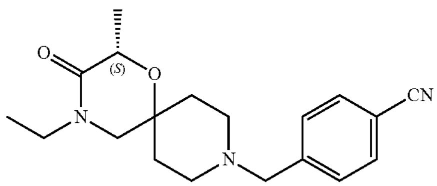 | (S)-4-((4-ethyl-2-methyl-3-oxo-1-oxa-4,9-diazaspiro[5.5]undecan-9-yl)methyl)benzonitrile |
| 82 | 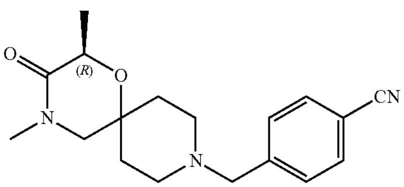 | (R)-4-((2,4-dimethyl-3-oxo-1-oxa-4,9-diazaspiro[5.5]undecan-9-yl)methyl)benzonitrile |
| 83 | 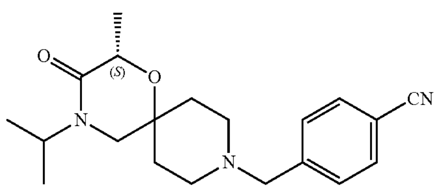 | (S)-4-((4-isopropyl-2-methyl-3-oxo-1-oxa-4,9-diazaspino[5.5]undecan-9-yl)methyl)benzonitrile |
| 84 | 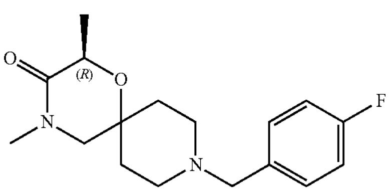 | (R)-9-(4-fluorobenzyl)-2,4-dimethyl-1-oxa-4,9-diazaspiro[5.5]undecan-3-one |
| 85 | 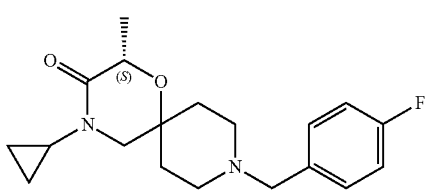 | (S)-4-cyclopropyl-9-(4-fluorobenzyl)-2-methyl-1-oxa-4,9-diazaspiro[5.5]undecan-3-one |
| 86 | 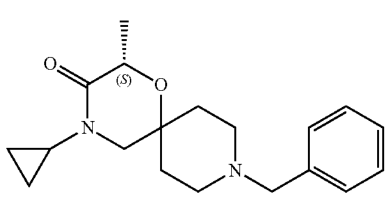 | (S)-9-benzyl-4-cyclopropyl-2-methyl-1-oxa-4,9-diazaspiro[5.5]undecan-3-one |
| 87 | 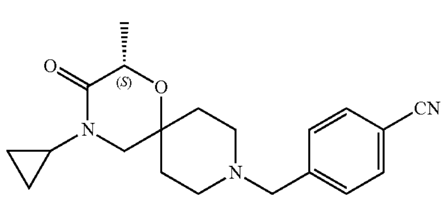 | (S)-4-((4-cyclopropyl-2-methyl-3-oxo-1-oxa-4,9-diazaspiro[5.5]undecan-9-yl)methyl)benzonitrile |

| EXAMPLE | Structure | CHEMICAL NAME |
| --- | --- | --- |
| 88 | 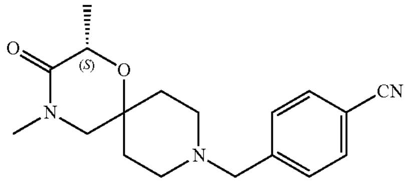 | (S)-4-((2,4-dimethyl-3-oxo-1-oxa-4,9-diazaspiro[5.5]undecan-9-yl)methyl)benzonitrile |
| 89 | 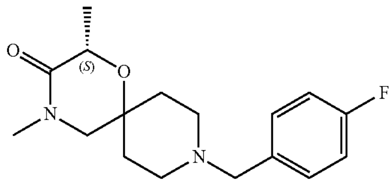 | (S)-9-(4-fluorobenzyl)-2,4-dimethyl-1-oxa-4,9-diazaspiro[5.5]undecan-3-one |
| 90 | 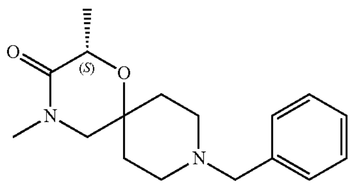 | (S)-9-benzyl-2,4-dimethyl-1-oxa-4,9-diazaspiro[5.5]undecan-3-one |
| 91 | 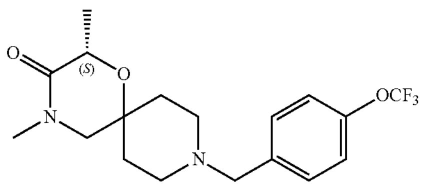 | (S)-2,4-dimethyl-9-(4-(trifluoromethoxy)benzyl)-1-oxa-4,9-diazaspiro[5.5]undecan-3-one |
| 92 | 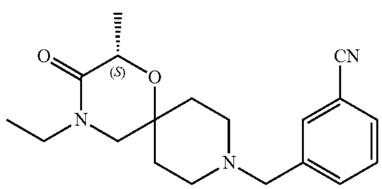 | (S)-3-((4-ethyl-2-methyl-3-oxo-1-oxa-4,9-diazaspiro[5.5]undecan-9-yl)methyl)benzonitrile |
| 93 | 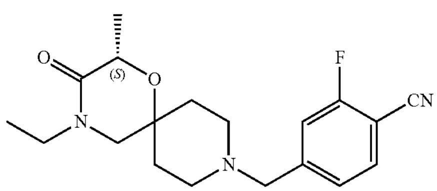 | (S)-4-((4-ethyl-2-methyl-3-oxo-1-oxa-4,9-diazaspiro[5.5]undecan-9-yl)methyl)-2-fluorobenzonitrile |
| 94 | 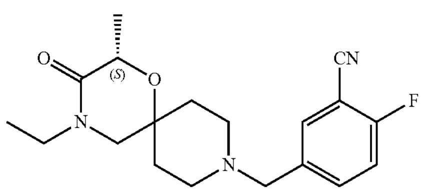 | (S)-5-((4-ethyl-2-methyl-3-oxo-1-oxa-4,9-diazaspiro[5.5]undecan-9-yl)methyl)-2-fluorobenzonitrile |
| 95 | 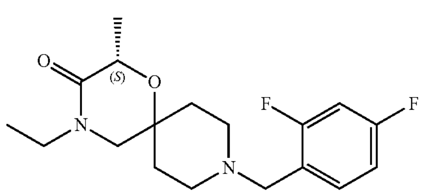 | (S)-9-(2,4-difluorobenzyl)-4-ethyl-2-methyl-1-oxa-4,9-diazaspiro[5.5]undecan-3-one |

-continued

| EXAMPLE | Structure | CHEMICAL NAME |
|---|---|---|
| 96 | 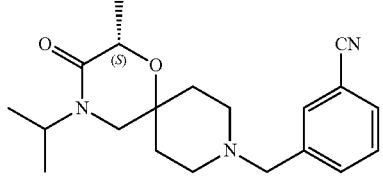 | (S)-3-((4-isopropyl-2-methyl-3-oxo-1-oxa-4,9-diazaspiro[5.5]undecan-9-yl)methyl)benzonitrile |
| 97 | 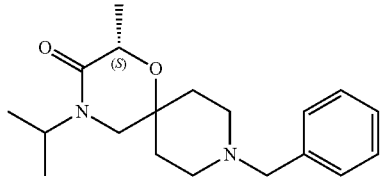 | (S)-9-benzyl-4-isopropyl-2-methyl-1-oxa-4,9-diazaspiro[5.5]undecan-3-one |
| 98 | 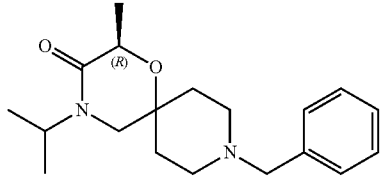 | (R)-9-benzyl-4-isopropyl-2-methyl-1-oxa-4,9-diazaspiro[5.5]undecan-3-one |
| 99 | 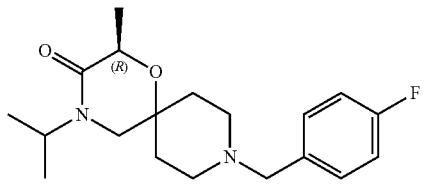 | (R)-9-(4-fluorobenzyl)-4-isopropyl-2-methyl-1-oxa-4,9-diazaspiro[5.5]undecan-3-one |
| 100 | 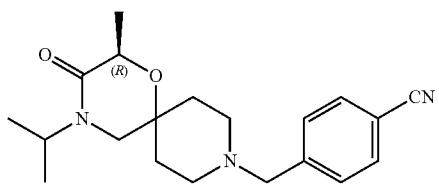 | (R)-4-((4-isopropyl-2-methyl-3-oxo-1-oxa-4,9-diazaspiro[5.5]undecan-9-yl)methyl)benzonitrile |
| 101 | 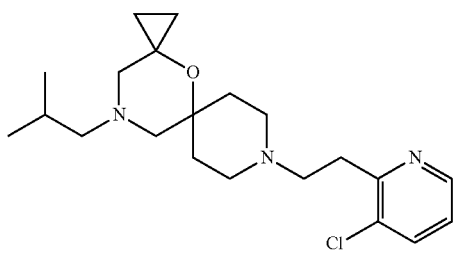 [SMILES: CC(C)CN1CC2(CCN(CCc3ncccc3Cl)CC2)OC2(CC2)C1] | 8-(2-(3-chloropyridin-2-yl)ethyl)-12-isobutyl-4-oxa-8,12-diazadispiro[2.1.5.3]tridecane |
| 102 | 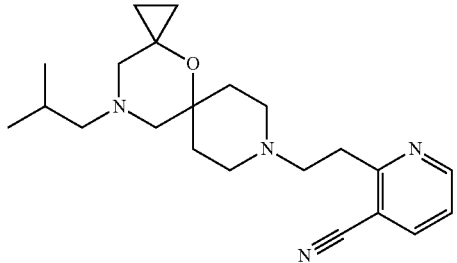 [SMILES: CC(C)CN1CC2(CCN(CCc3ncccc3C#N)CC2)OC2(CC2)C1] | 2-(2-(12-isobutyl-4-oxa-8,12-diazadispiro[2.1.5.3]tridecan-8-yl)ethyl)nicotinonitrile |

-continued

| EXAMPLE | Structure | CHEMICAL NAME |
|---|---|---|
| 103 | 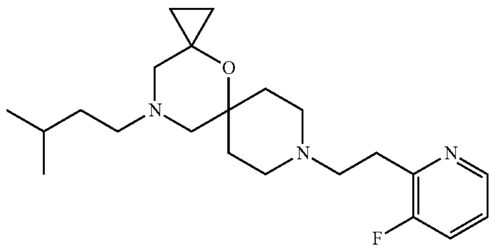 [SMILES: CC(C)CCN1CC2(CCN(CCc3ncccc3F)CC2)OC2(CC2)C1] | 8-(2-(3-fluoropyridin-2-yl)ethyl)-12-isopentyl-4-oxa-8,12-diazadispiro[2.1.5.3]tridecane |
| 104 | 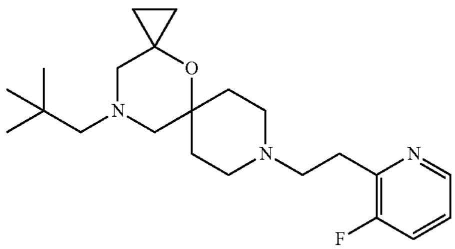 [SMILES: CC(C)(C)CN1CC2(CCN(CCc3ncccc3F)CC2)OC2(CC2)C1] | 8-(2-(3-fluoropyridin-2-yl)ethyl)-12-neopentyl-4-oxa-8,12-diazadispiro[2.1.5.3]tridecane |
| 105 | 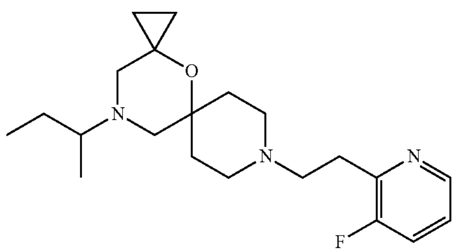 | 12-(sec-butyl)-8-(2-(3-fluoropyridin-2-yl)ethyl)-4-oxa-8,12-diazadispiro[2.1.5.3]tridecane |
| 106 | 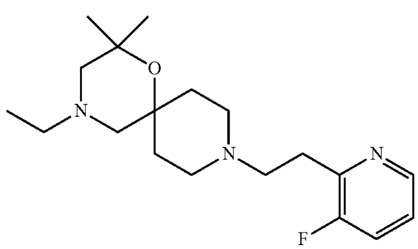 [SMILES: CCN1CC(C)(C)OC2(CCN(CCc3ncccc3F)CC2)C1] | 4-ethyl-9-(2-(3-fluoropyridin-2-yl)ethyl)-2,2-dimethyl-1-oxa-4,9-diazaspiro[5.5]undecane |
| 107 | 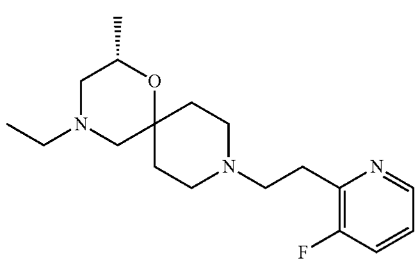 [SMILES: CCN1C[C@H](C)OC2(CCN(CCc3ncccc3F)CC2)C1] | (S)-4-ethyl-9-(2-(3-fluoropyridin-2-yl)ethyl)-2-methyl-1-oxa-4,9-diazaspiro[5.5]undecane |
| 108 | 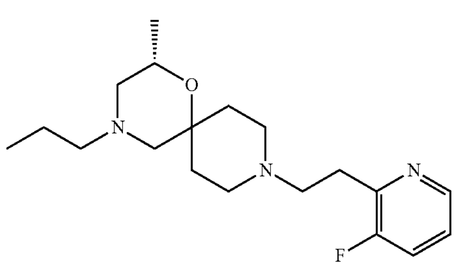 [SMILES: CCCN1C[C@H](C)OC2(CCN(CCc3ncccc3F)CC2)C1] | (S)-9-(2-(3-fluoropyridin-2-yl)ethyl)-2-methyl-4-propyl-1-oxa-4,9-diazaspiro[5.5]undecane |

-continued

| EXAMPLE | Structure | CHEMICAL NAME |
|---|---|---|
| 109 | 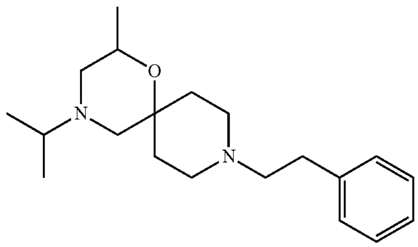 [SMILES: CC1CN(C(C)C)CC2(CCN(CCc3ccccc3)CC2)O1] | 4-Isopropyl-2-methyl-9-phenethyl-1-oxa-4,9-diazaspiro[5.5]undecane |
| 110 | 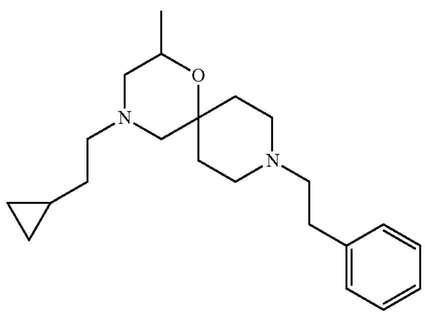 [SMILES: CC1CN(CCC2CC2)CC2(CCN(CCc3ccccc3)CC2)O1] | 4-(2-cyclopropylethyl)-2-methyl-9-phenethyl-1-oxa-4,9-diazaspiro[5.5]undecane |
| 111 | 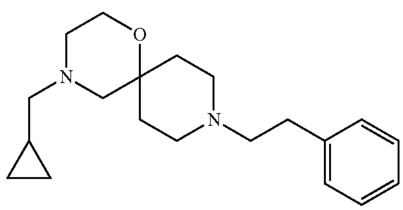 [SMILES: c1ccc(CCN2CCC3(CC2)CN(CC2CC2)CCO3)cc1] | 4-(cyclopropylmethyl)-9-phenethyl-1-oxa-4,9-diazaspiro[5.5]undecane |
| 112 | 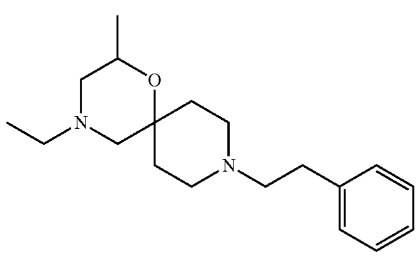 [SMILES: CCN1CC(C)OC2(CCN(CCc3ccccc3)CC2)C1] | 4-Ethyl-2-methyl-9-phenethyl-1-oxa-4,9-diazaspiro[5.5]undecane |
| 113 | | 4-isopropyl-2,2-dimethyl-9-phenethyl-1-oxa-4,9-diazaspiro[5.5]undecane | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I), $R_1$ is selected from substituted or unsubstituted $C_{1-6}$ alkyl, substituted or unsubstituted $C_{2-6}$ alkenyl, substituted or unsubstituted $C_{2-6}$ alkynyl and substituted or unsubstituted cycloalkyl;

wherein said cycloalkyl in $R_1$ if substituted, is substituted with one or more substituent/s selected from halogen, $—R_{11}$, $—OR_{11}$, $—NO_2$, $—NR_{11}R_{11'''}$, $NR_{11}C(O)R_{11'}$, $—NR_{11}S(O)_2R_{11'}$, $—S(O)_2NR_{11}R_{11'}$, $—NR_{11}C(O)NR_{11}R_{11'''}$, $—SR_{11}$, $—S(O)R_{11}$, $S(O)_2R_{11}$, $—CN$, haloalkyl, haloalkoxy, $—C(O)OR_{11}$, $—C(O)NR_{11}R_{11'}$, $—OCH_2CH_2OH$, $—NR_{11}S(O)_2NR_{11'}R_{11'''}$ and $C(CH_3)_2OR_{11}$;

additionally, cycloalkyl in $R_1$ if substituted, may also be substituted with  or $=O$;

wherein the alkyl, alkenyl or alkynyl in $R_1$, if substituted, is substituted with one or more substituent/s selected from $—OR_{11}$, halogen, $—CN$, haloalkyl, haloalkoxy and $—NR_{11}R_{11'''}$;

wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of mixture of at least two of the stereoisomers, preferably enantiomers and/or diastereomers, in any mixing ratio, or a corresponding salt thereof, or a corresponding solvate, thereof.

In another embodiment of the invention the compound of general Formula (I), $R_2$ is selected from hydrogen, substituted or unsubstituted $C_{1-6}$ substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, wherein said cycloalkyl, aryl or heterocyclyl in $R_2$, if substituted, is substituted with one or more substituent/s selected from halogen, $—R_{12}$, $—OR_{12}$, $—NO_2$, $—NR_{12}R_{12'''}$, $NR_{12}C(O)R_{12'}$, $—NR_{12}S(O)_2R_{12'}$, $—S(O)_2NR_{12}R_{12'}$, $—NR_{12}C(O)NR_{12}R_{12'''}$, $—SR_{12}$, $—S(O)R_{12}$, $S(O)_2R_{12}$, $—CN$, haloalkyl, haloalkoxy, $—C(O)OR_{12}$, $—C(O)NR_{12}R_{12'}$, $—OCH_2CH_2OH$, $—NR_{12}S(O)_2NR_{12'}R_{12'''}$ and $C(CH_3)_2OR_{12}$;

additionally, cycloalkyl or non-aromatic heterocyclyl in $R_2$, if substituted, may also be substituted with  or $=O$;

wherein the alkyl, alkenyl or alkynyl in $R_2$, if substituted, is substituted with one or more substituent/s selected from $—OR_{12}$, halogen, $—CN$, haloalkyl, haloalkoxy and $—NR_{12}R_{12'''}$;

wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers in any mixing ratio, or a corresponding salt thereof, or a corresponding solvate thereof.

In another embodiment of the invention the compound of general Formula (I), the alkyl, alkenyl or alkynyl, other than those defined in $R_1$ or $R_2$, if substituted, is substituted with one or more substituent/s selected from $—OR_{13}$, halogen, $—CN$, haloalkyl, haloalkoxy and $—NR_{13}R_{13'''}$;

wherein $R_{13}$ is selected from hydrogen, unsubstituted $C_{1-6}$ alkyl, unsubstituted $C_{2-6}$ alkenyl, and unsubstituted $C_{2-6}$ alkynyl;

$R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), the aryl, heterocyclyl or cycloalkyl other than those defined in $R_1$ or $R_2$, if substituted, is substituted with one or more substituent/s selected from halogen, $—R_{14}$, $—OR_{14}$, $—NO_2$, $—NR_{14}R_{14'''}$, $NR_{14}C(O)R_{14'}$, $—NR_{14}S(O)_2R_{14'}$, $—S(O)_2NR_{14}R_{14'}$, $—NR_{14}C(O)NR_{14}R_{14'''}$, $—SR_{14}$, $—S(O)R_{14}$, $S(O)_2R_{14}$, $—CN$, haloalkyl, haloalkoxy, $—C(O)OR_{14}$, $—C(O)NR_{14}R_{14'}$, $—OCH_2CH_2OH$, $—NR_{14}S(O)_2NR_{14'}R_{14'''}$ and $C(CH_3)_2OR_{14}$;

additionally, wherein cycloalkyl or non-aromatic heterocyclyl, other than those defined in $R_1$ or $R_2$, if substituted, may also be substituted with  or $=O$;

wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the embodiments of the present invention, the cycloalkyl in $R_1$ if substituted, is substituted with one or more substituent/s selected from halogen, $—R_{11}$, $—OR_{11}$, $—NO_2$, $—NR_{11}R_{11'''}$, $NR_{11}C(O)R_{11'}$, $—NR_{11}S(O)_2R_{11'}$, $—S(O)_2NR_{11}R_{11'}$, $—NR_{11}C(O)NR_{11}R_{11'''}$, $—SR_{11}$, $—S(O)R_{11}$, $S(O)_2R_{11}$, $—CN$, haloalkyl, haloalkoxy, $—C(O)OR_{11}$, $—C(O)NR_{11}R_{11'}$, $—OCH_2CH_2OH$, $—NR_{11}S(O)_2NR_{11'}R_{11'''}$ and $C(CH_3)_2OR_{11}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the embodiments of the present invention, the cycloalkyl in $R_1$ if substituted, may also be substituted with  or $=O$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the embodiments of the present invention, the alkyl, alkenyl or alkynyl in $R_1$, if substituted, is substituted with one or more substituent/s selected from —$OR_{11}$, halogen, —CN, haloalkyl, haloalkoxy and —$NR_{11}R_{11'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention, the cycloalkyl, aryl or heterocyclyl in $R_2$, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}C(O)R_{12'}$, —$S(O)_2R_{12'}$, —$NR_{12}C(O)_2NR_{12}R_{12'}$, —$SR_{12}$, $S(O)_2R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention, the cycloalkyl or non-aromatic heterocyclyl in $R_2$, if substituted, may also be substituted with  or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention, the alkyl, alkenyl or alkynyl in $R_2$, if substituted, is substituted with one or more substituent/s selected from —$OR_{12}$, halogen, —CN, haloalkyl, haloalkoxy and —$NR_{12}R_{12'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to alkyls other than those defined in $R_1$ or $R_2$ of any of the embodiments of the present invention, the alkyl, alkenyl or alkynyl, other than those defined in $R_1$ or $R_2$, if substituted, is substituted with one or more substituent/s selected from —$OR_{13}$, halogen, —CN, haloalkyl, haloalkoxy and —$NR_{13}R_{13'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to the cycloalkyl, aryl or heterocyclyl other than those defined in $R_1$ or $R_2$ of any of the embodiments of the present invention.

the aryl, heterocyclyl or cycloalkyl other than those defined in $R_1$ or $R_2$, if substituted, is substituted with one or more substituent/s selected from halogen, —$R_{14}$, —$OR_{14}$, —$NO_2$, —$NR_{14}R_{14'''}$, —$NR_{14}C(O)R_{14'}$, —$NR_{14}S(O)_2R_{14'}$, —$S(O)_2NR_{14}R_{14'}$, —$NR_{14}C(O)NR_{14'}R_{14''}$, —$SR_{14}$, —$S(O)R_{14}$, $S(O)_2R_{14}$, —CN, haloalkyl, haloalkoxy, —$C(O)OR_{14}$, —$C(O)NR_{14}R_{14'}$, —$OCH_2CH_2OH$, —$NR_{14}S(O)_2NR_{14'}R_{14''}$ and $C(CH_3)_2OR_{14}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to the cycloalkyl, aryl or heterocyclyl other than those defined in $R_1$ or $R_2$ of any of the embodiments of the present invention, the cycloalkyl or non-aromatic heterocyclyl, other than those defined in $R_1$ or $R_2$, if substituted, may also be substituted with  or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I), the halogen is fluorine, chlorine, iodine or bromine, preferably fluorine or chlorine; more preferably fluorine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I), the haloalkyl is —$CF_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the compound according to the invention of general Formula (I), the haloalkoxy is —$OCF_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As this invention is aimed at providing a compound or a chemically related series of compounds which act as ligands of the σ₁ receptor it is a very preferred embodiment in which the compounds are selected which act as ligands of the σ₁ receptor and especially compounds which have a binding expressed as $K_i$ which is preferably <1000 nM, more preferably <500 nM, even more preferably <100 nM.

In the following the phrase "compound of the invention" is used. This is to be understood as any compound according to the invention as described above according to general Formula (I), (I'), ($I^{a'}$), ($I^{b'}$), ($I^{c'}$), ($I^{2'}$), ($I^{3'}$), ($I^{4'}$), ($I^{5'}$), ($I^{6'}$) or ($I^{7'}$).

The compounds of the invention represented by the above described Formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In general the processes are described below in the experimental part. The starting materials are commercially available or can be prepared by conventional methods.

A preferred aspect of the invention is also a process for the production of a compound according to Formula (I).

A preferred aspect of the invention is a process for the production of a compound according to Formula (I),

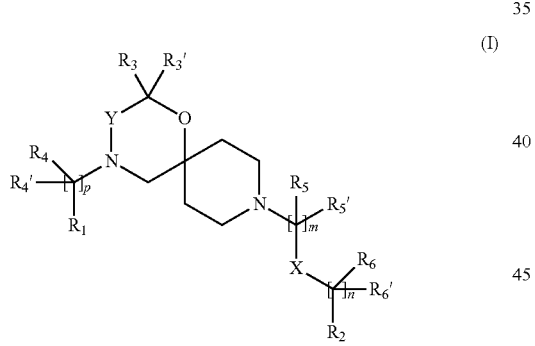

and wherein $R_1$, $R_2$, $R_3$, $R_{3'}$, $R_4$, $R_{4'}$, $R_5$, $R_{5'}$, $R_6$, $R_{6'}$, m, n, p, X and Y are as defined in the description, following schemes 1 to 4.

In all processes and uses described underneath, the values of $R_1$, $R_2$, $R_3$, $R_{3'}$, $R_4$, $R_{4'}$, $R_5$, $R_{5'}$, $R_6$, $R_{6'}$, m, n, p, X and Y are as defined in the deception (unless otherwise stated), LG represents a leaving group, such as halogen, mesylate, tosylate or triflate, with the proviso that when Y=CO it can only be chloro or bromo, V represents an aldehyde or another leaving group (such as halogen, mesylate, tosylate or triflate) and P' represents a suitable protecting group (preferably 4-methoxybenzyl or benzyl).

A preferred embodiment of the invention is a process for the preparation of compounds of general formula (I), said process comprises:

a) an intramolecular cyclization of a compound of formula VIIa

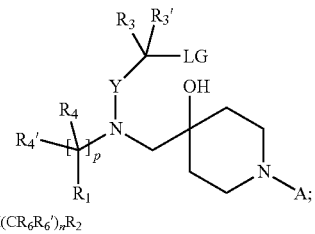

or b) the reaction of a compound of formula VIIIH

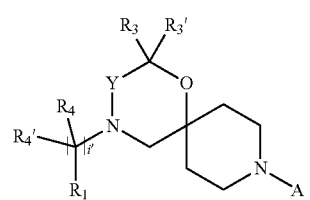

with a compound of formula IX, X or XI,

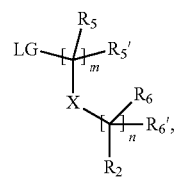

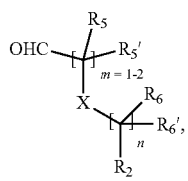

or c1) when Y is CH₂, by the alkylation of a compound of formula XIV

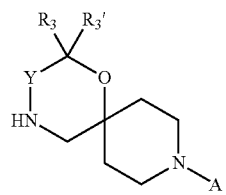

XIV

A = (CR₅R₅')ₘX(CR₆R₆')ₙR₂ with a compound of formula XV

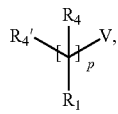

XV being the compound of formula XV an alkylating agent and V a leaving group, or alternatively by the reductive amination reaction of a compound of formula XIV with a compound of formula XV, being the compound of formula XV an aldehyde and V a C(O)H group;

or c2) when Y is C(O), by the alkylation of a compound of formula XIV

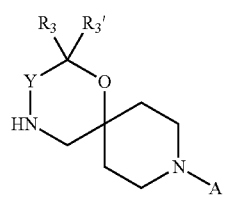

XIV

A = (CR₅R₅')ₘX(CR₆R₆')ₙR₂ with a compound of formula XV

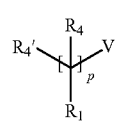

XV being the compound of formula XV an alkylating agent and V a leaving group.

In another embodiment of the invention is a process for the preparation of compounds of general formula (I), said process comprises an intramolecular cyclization of a compound of formula VIIa

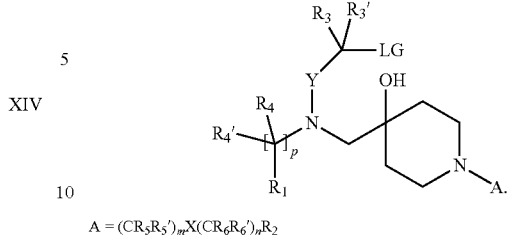

VIIa

A = (CR₅R₅')ₘX(CR₆R₆')ₙR₂

In another embodiment of the invention is a process for the preparation of compounds of general formula (I) said process comprises the reaction of a compound of formula VIIIH

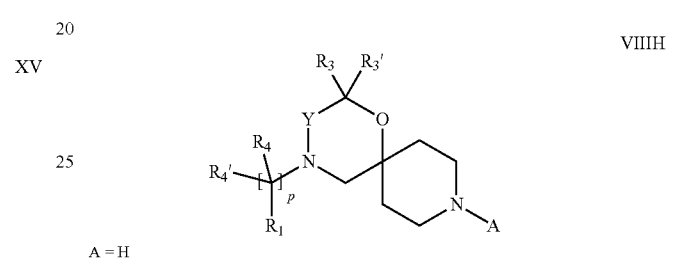

VIIIH

A = H with a compound of formula IX, X or XI,

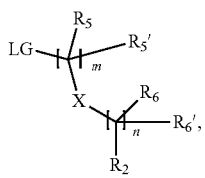

IX

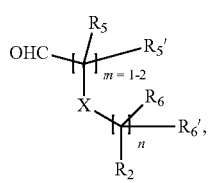

X

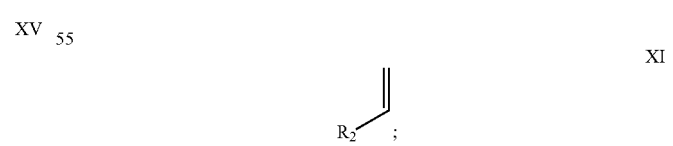

XI

In another embodiment of the invention is a process for the preparation of compounds of general formula (I) wherein Y is CH₂, said process comprises the alkylation of a compound of formula XIV

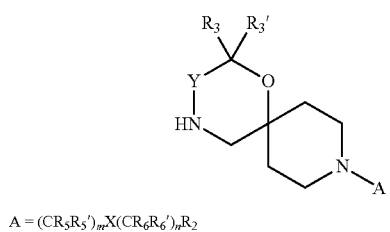

A = (CR$_5$R$_5$')$_m$X(CR$_6$R$_6$')$_n$R$_2$ with a compound of formula XV

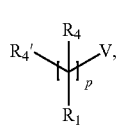

being the compound of formula XV an alkylating agent and V a leaving group, or alternatively by the reductive amination reaction of a compound of formula XIV with a compound of formula XV, being the compound of formula XV an aldehyde and V a C(O)H group;

In another embodiment of the invention is a process for the preparation of compounds of general formula (I) wherein Y is C(O), by the alkylation of a compound of formula XIV

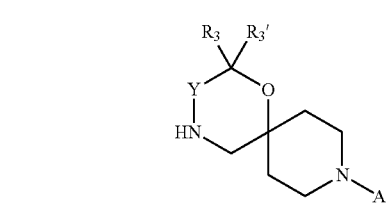

A = (CR$_5$R$_5$')$_m$X(CR$_6$R$_6$')$_n$R$_2$ with a compound of formula XV

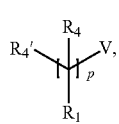

being the compound of formula XV an alkylating agent and V a leaving group.

In another preferred embodiment of the invention is a process for the preparation, of compounds of general formula (I) wherein Y represents CO and R$_3$ and R$_3'$ taken together with the connecting C-atom form a cyclopropyl (compounds of formula Ic),

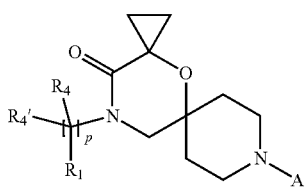

A = (CR$_5$R$_5$')$_m$X(CR$_6$R$_6$')$_n$R$_2$ said process comprises a) the treatment with a strong base of a compound of formula Ib wherein R$_s$=R$_s'$=H and s=1

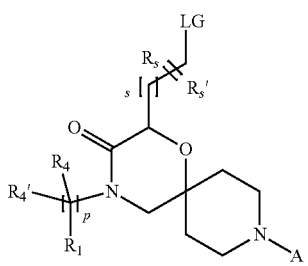

A = (CR$_5$R$_5$')$_m$X(CR$_6$R$_6$')$_n$R$_2$ or b) a cyclopropanation reaction on a compound of formula XXI

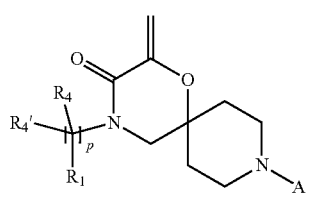

A = (CR$_5$R$_5$')$_m$X(CR$_6$R$_6$')$_n$R$_2$ or c) the alkylation of a compound of formula XXV

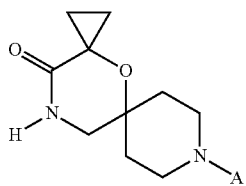

A = (CR$_5$R$_5$')$_m$X(CR$_6$R$_6$')$_n$R$_2$ with a compound of formula XV

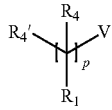

XV being the compound of formula XV an alkylating agent and V a leaving group;
or
d) the reaction of a compound of formula XIXH

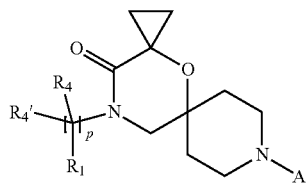

XIXH

A = H with compound of formula IX, X, or XI

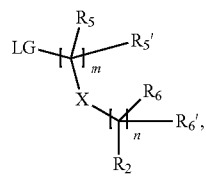

IX

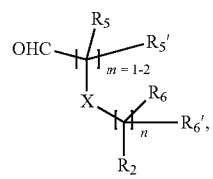

X

XI

In another preferred embodiment of the invention is a process for the preparation, of compounds of general formula (I) wherein Y represents CO and $R_3$ and $R_{3'}$ taken together with the connecting C-atom form a cyclopropyl (compounds of formula Ic),

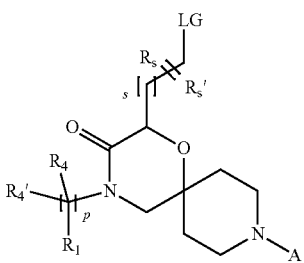

Ic $A = (CR_5R_5')_m X(CR_6R_6')_n R_2$ said process comprises
the treatment with a strong base of a compound of formula Ib wherein $R_s = R_{s'} = H$ and $s = 1$ Ib $A = (CR_5R_5')_m X(CR_6R_6')_n R_2$ In another preferred embodiment of the invention is a process for the preparation, of compounds of general formula (I) wherein Y represents CO and
$R_3$ and $R_{3'}$ taken together with the connecting C-atom form a cyclopropyl (compounds of formula Ic), Ic $A = (CR_5R_5')_m X(CR_6R_6')_n R_2$ said process comprises a cyclopropanation reaction on a compound of formula XXI

XXI $A = (CR_5R_5')_m X(CR_6R_6')_n R_2$

In another preferred embodiment of the invention is a process for the preparation, of compounds of general formula (I) wherein Y represents CO and $R_3$ and $R_{3'}$ taken together with the connecting C-atom form a cyclopropyl (compounds of formula Ic),

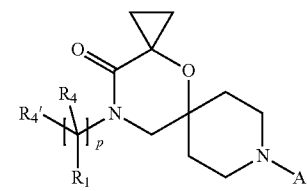

Ic

A = (CR$_5$R$_5$')$_m$X(CR$_6$R$_6$')$_n$R$_2$ said process comprises the alkylation of a compound of formula XXV

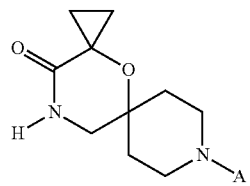

XXV

A = (CR$_5$R$_5$')$_m$X(CR$_6$R$_6$')$_n$R$_2$ with a compound of formula XV

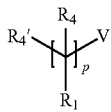

XV being the compound of formula XV an alkylating agent and V a leaving group.

In another preferred embodiment of the invention is a process for the preparation, of compounds of general formula (I) wherein Y represents CO and R$_3$ and R$_3$' taken together with the connecting C-atom form a cyclopropyl (compounds of formula Ic),

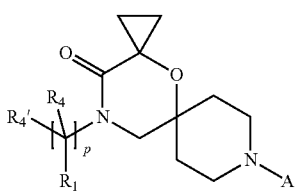

Ic

A = (CR$_5$R$_5$')$_m$X(CR$_6$R$_6$')$_n$R$_2$ said process comprises the reaction of a compound of formula XIXH

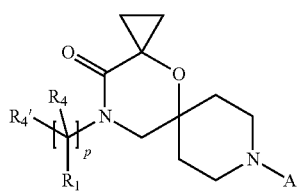

XIXH

A = H with a compound of formula IX, X or XI,

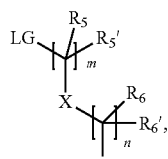

IX

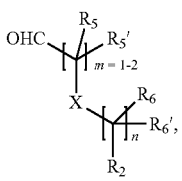

X

XI

In another particular embodiment a compound of Formula II, IIP, III, IIIP, IVa, IVb, Vb, VbP, Va, VaP, VI, VIIa, VIIb, VIIb, VIIbP, VIIIP, VIIIH, IX, X, XI, XII, XIIP, XIII, XIIIP, XIV, XIVP, XIVH, XV, XVI, XVIP, XVIH, Ia, XVIIP, XVIIH, Ib, XVIIIP, Ic, XIXP, XIXH, Id, XXP, XXH, XXI, XXIP, XXIH, XXII, XXIIP, XXIIH, XXIII, XXIIIP, XXIIIH, XXIV, XXIVP, XXIVH, XXV, XXVP, XXVH, Ie, XXVIP, XXVIH, XXVIIa, XXVIIb, XXVIIc, If, XXVIIIP, XXVIIIH, Ig, XXIXP, XXIXH, Ih, XXXP, XXXH, XXXI, XXXIP, XXXIH, XXXII, XXXIIP, XXXIIH, XXXIII, XXXIIIP, XXXIIIH, XXXIV, XXXIVP or XXXIVH,

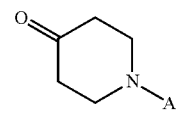

II

A = (CR$_5$R$_5$')$_m$X(CR$_6$R$_6$')$_n$R$_2$
IIP A = P

III

A = (CR$_5$R$_5$')$_m$X(CR$_6$R$_6$')$_n$R$_2$
IIIP A = P

101
-continued

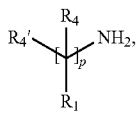
IVa

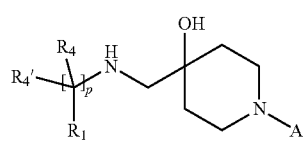
IVb

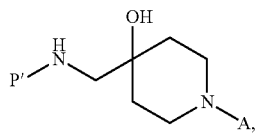
Va

A = (CR$_5$R$_5$')$_m$X(CR$_6$R$_6$')$_n$R$_2$
VaP A = P

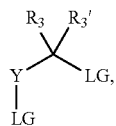
Vb

A = (CR$_5$R$_5$')$_m$X(CR$_6$R$_6$')$_n$R$_2$
VbP A = P

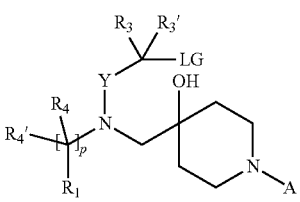
VI

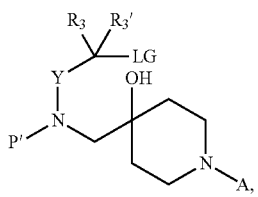
VIIa

A = (CR$_5$R$_5$')$_m$X(CR$_6$R$_6$')$_n$R$_2$
VIIaP A = P

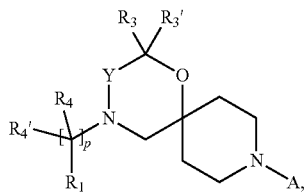
VIIb

A = (CR$_5$R$_5$')$_m$X(CR$_6$R$_6$')$_n$R$_2$
VIIbP A = P

I

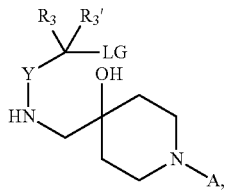

A = (CR$_5$R$_5$')$_m$X(CR$_6$R$_6$')$_n$R$_2$
VIIIP A = P
VIIIH A = H

102
-continued

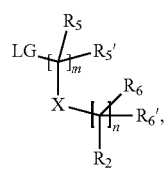
XIII

A = (CR$_5$R$_5$')$_m$X(CR$_6$R$_6$')$_n$R$_2$
XIIIP A = P

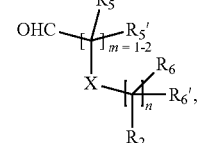
IX

X

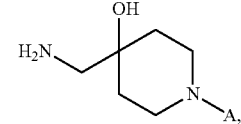
XI

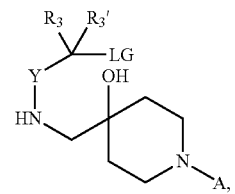
XII

A = (CR$_5$R$_5$')$_m$X(CR$_6$R$_6$')$_n$R$_2$
XIIP A = P

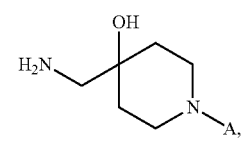
XIII

A = (CR$_5$R$_5$')$_m$X(CR$_6$R$_6$')$_n$R$_2$
XIIIP A = P

XII

A = (CR$_5$R$_5$')$_m$X(CR$_6$R$_6$')$_n$R$_2$
XIIP A = P

103
-continued

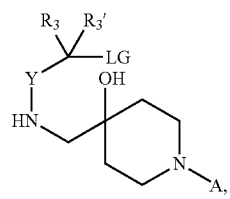

A = (CR₅R₅')ₘX(CR₆R₆')ₙR₂
XIIIP A = P

XIII

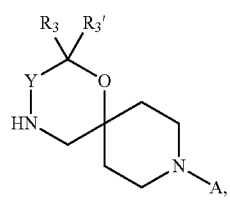

A = (CR₅R₅')ₘX(CR₆R₆')ₙR₂
XIVP A = P
XIVH A = H

XIV

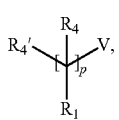

XV

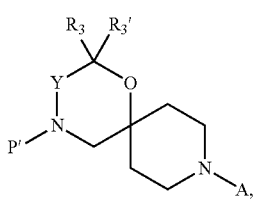

A = (CR₅R₅')ₘX(CR₆R₆')ₙR₂
XVIP A = P
XVIH A = H

XVI

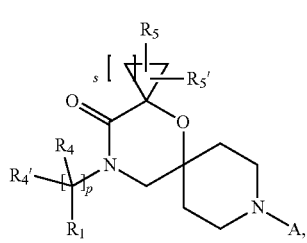

A = (CR₅R₅')ₘX(CR₆R₆')ₙR₂
XVIIP A = P
XVIIH A = H

Ia

104
-continued

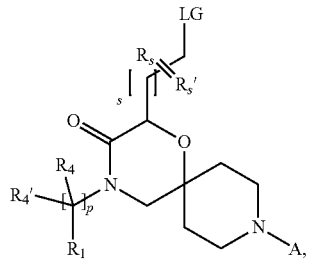

A = (CR₅R₅')ₘX(CR₆R₆')ₙR₂
XVIIIP A = P

Ib

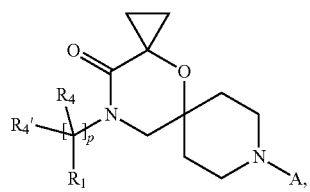

XIXH A = H
A = (CR₅R₅')ₘX(CR₆R₆')ₙR₂
XIXP A = P
XIXH A = H

Ic

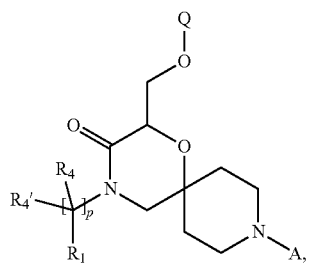

A = (CR₅R₅')ₘX(CR₆R₆')ₙR₂
XXP A = P
XXH A = H

Id

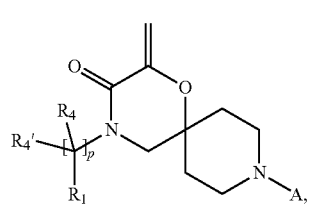

A = (CR₅R₅')ₘX(CR₆R₆')ₙR₂
XXIP A = P
XXIH A = H

XXI

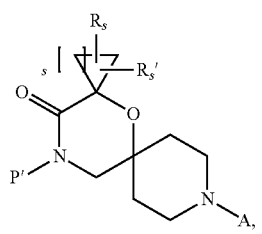

A = (CR₅R₅')ₘX(CR₆R₆')ₙR₂
XXIIP A = P
XXIIH A = H

XXII

-continued

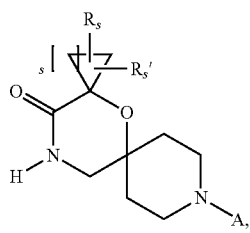

A = (CR₅R₅')ₘX(CR₆R₆')ₙR₂
XXIIIP A = P
XXIIIH A = H

XXIII

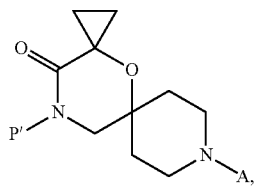

A = (CR₅R₅')ₘX(CR₆R₆')ₙR₂
XXIVP A = P
XXIVH A = H

XXIV

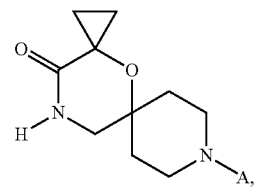

A = (CR₅R₅')ₘX(CR₆R₆')ₙR₂
XXVP A = P
XXVH A = H

XXV

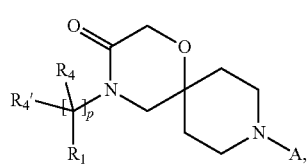

A = (CR₅R₅')ₘX(CR₆R₆')ₙR₂
XXVIP A = P
XXVIH A = H

Ie

R₃X',  XXVIIa

R₃'X',  XXVIIb

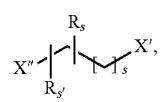  XXVIIc

-continued

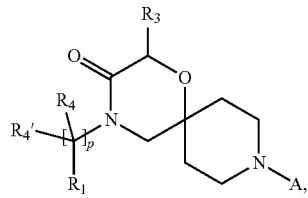

A = (CR₅R₅')ₘX(CR₆R₆')ₙR₂
XXVIIIP A = P
XXVIIIH A = H

If

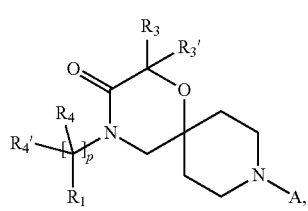

A = (CR₅R₅')ₘX(CR₆R₆')ₙR₂
XXIXP A = P
XXIXH A = H

Ig

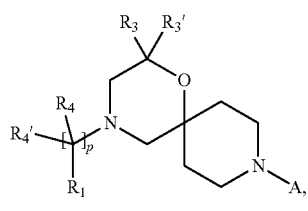

A = (CR₅R₅')ₘX(CR₆R₆')ₙR₂
XXXP A = P
XXXH A = H

Ih

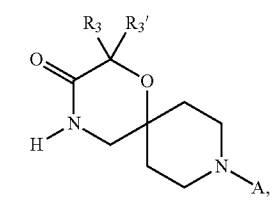

A = (CR₅R₅')ₘX(CR₆R₆')ₙR₂
XXXIP A = P
XXXIH A = H

XXXI

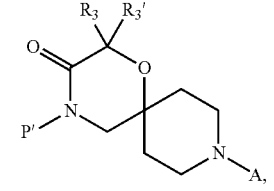

A = (CR₅R₅')ₘX(CR₆R₆')ₙR₂
XXXIIP A = P
XXXIIH A = H

XXXII

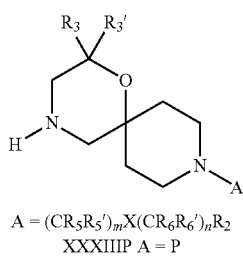

XXXIII

A = (CR₅R₅')ₘX(CR₆R₆')ₙR₂
XXXIIIP A = P
XXXIIIH A = H

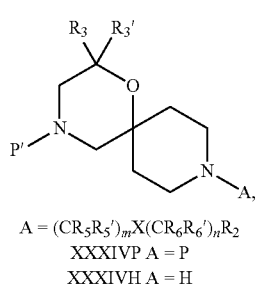

XXXIV

A = (CR₅R₅')ₘX(CR₆R₆')ₙR₂
XXXIVP A = P
XXXIVH A = H is used for the preparation of a compound of Formula (I).

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formula I or a pharmaceutically acceptable salt or stereoisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such a sterile solutions, suspensions or lyophilized products in the appropriate unit dosage form. Adequate excipients can be used, such as hulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight a the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formula I, or a pharmaceutically acceptable salt or isomer thereof, for use as a medicament for the treatment of drug abuse or addiction.

Another aspect of the invention refers to the use of a compound of the invention in the manufacture of a medicament for the treatment or prophylaxis of drug abuse or addiction.

Another aspect of this invention relates to a method of treating or preventing drug abuse or addiction which method comprises administering to a patient in need of such a treatment a therapeutically effective amount of a compound as above defined or a pharmaceutical composition thereof.

The present invention is illustrated below with the aid of examples. These illustrations are given solely by way of example and do not limit the general spirit of the present invention.

General Experimental Part (Methods and Equipment of the Synthesis and Analysis

Scheme 1:

A 4-step process is described for the preparation of compounds of general formula (I) starting from a ketone of formula II, as shown in the following scheme:

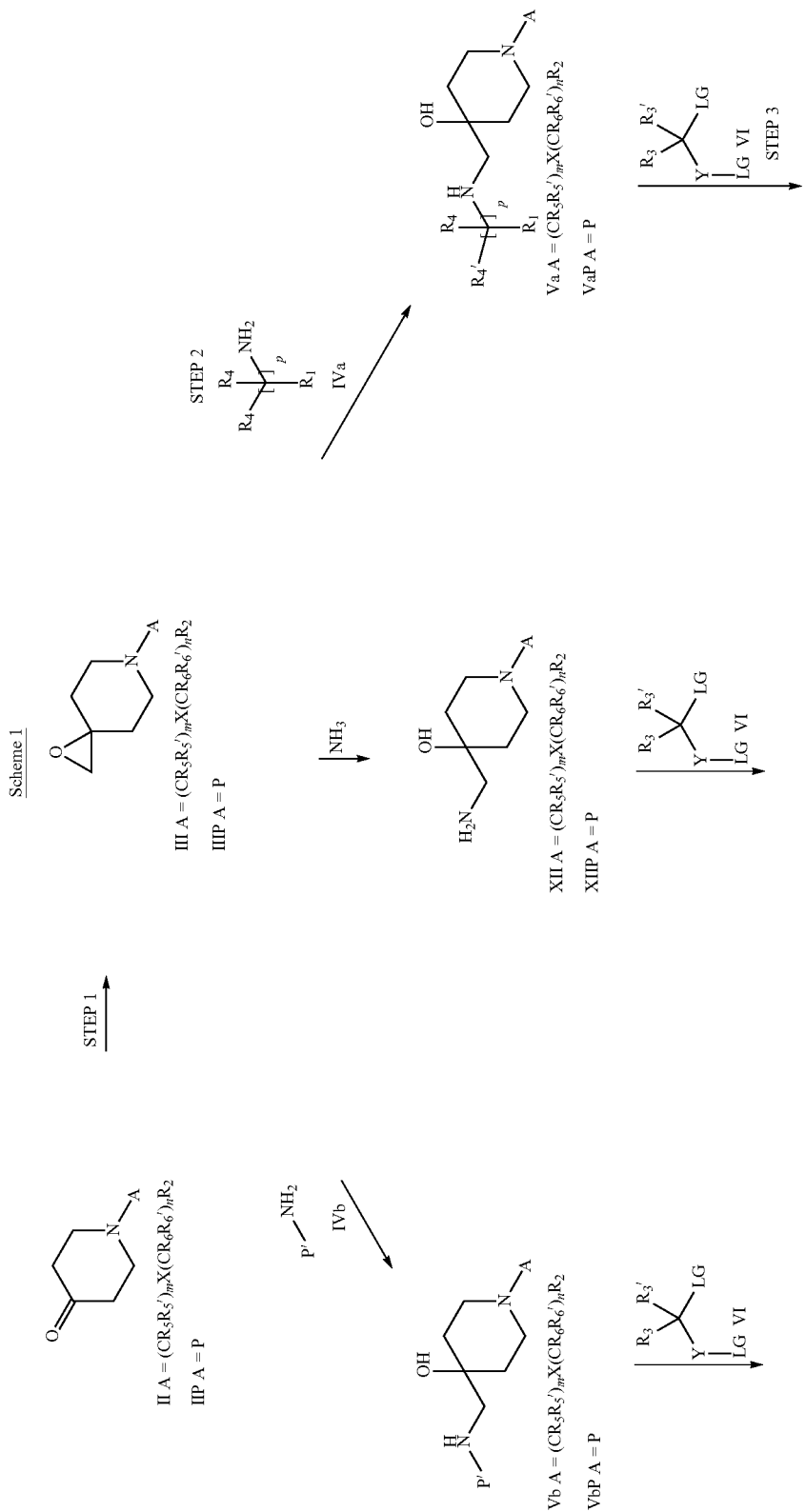

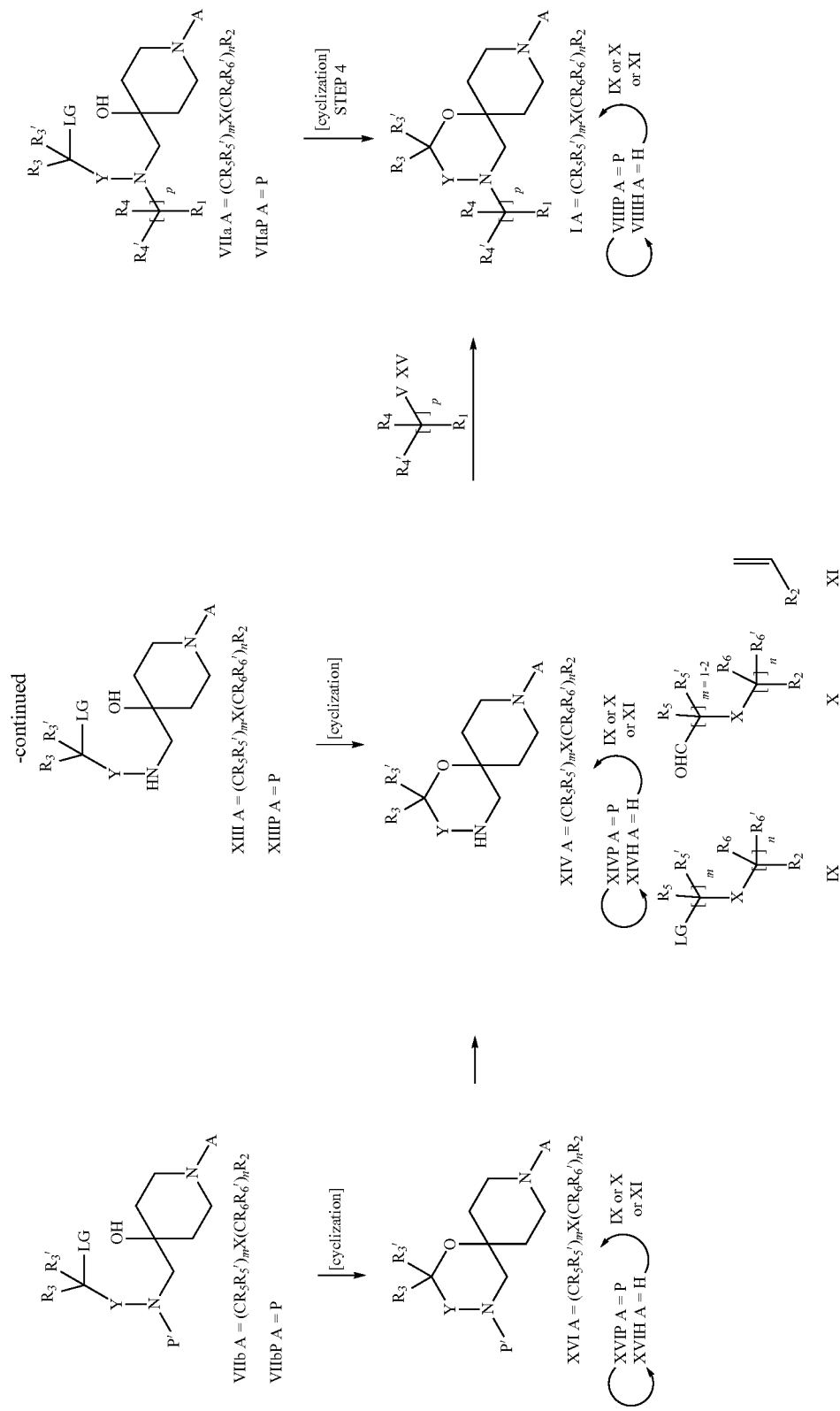

wherein $R_1$, $R_2$, $R_3$, $R_{3'}$, $R_4$, $R_{4'}$, $R_5$, $R_{5'}$, $R_6$, $R_{6'}$, X, Y, m, n and p have the meanings as defined above for a compound of formula (I), LG represents a leaving group such such as halogen, mesylate, tosylate or triflate, with the proviso that when Y=CO it can only be chloro or bromo, V represents an aldehyde or another leaving group (such as halogen, mesylate, tosylate or triflate), P represents a suitable protecting group (preferably Boc) and P' represents an orthogonal protecting group (preferably 4-methoxybenzyl or benzyl).

The 4 step-process is carried out as described below:

Step 1: A compound of formula III is prepared by treating a compound of formula II with a suitable methyl-transfer reagent such as trimethylsulfoxonium iodide or trimethylsulfonium iodide, in a suitable aprotic solvent such as dimethylsulfoxide or 1,2-dimethoxyethane or mixtures, and in the presence of a strong base such as sodium hydride or potassium tert-butoxide, at a suitable temperature, preferably comprised between 0° C. and 60° C.

Step 2: A compound of formula Va is prepared by reacting a compound of formula III with an amine of formula IVa, in a suitable solvent such as an alcohol, preferably ethanol-water mixtures, at a suitable temperature comprised between room temperature and the reflux temperature.

Step 3: A compound of formula VIIa is prepared by reacting a compound of formula Va with a compound of formula VI. Depending on the meaning of Y, the compound of formula VI can be of different nature and different reaction conditions will apply:
  a) When Y represents CO, VI is an acylating agent. The acylation reaction is carried out in a suitable solvent, such as dichloromethane or ethyl acetate-water mixtures; in the presence of an organic base such as triethylamine or diisopropylethylamine or an inorganic base such as $K_2CO_3$; and at a suitable temperature, preferably comprised between −78° C. and room temperature.
  b) When Y represents $CH_2$, VI is an alkylating agent. The alkylation reaction may be carried out in a suitable solvent, such as acetonitrile, dichloromethane, tetrahydrofuran, 1,4-dioxane or dimethylformamide; in the presence of an inorganic base such as $K_2CO_3$, $CS_2CO_3$ or NaH, or an organic base such as triethylamine or diisopropylethylamine, at a suitable temperature comprised between room temperature and the reflux temperature. The OH group present may need protection previous to the alkylation reaction.

Step 4: The intramolecular cyclization of a compound of formula VIIa renders a compound of formula I. The cyclization reaction is carried out in a suitable solvent, such as tetrahydrofuran; in the presence of a strong base such as potassium tert-butoxide or sodium hydride; and at a suitable temperature, comprised between −78° C. and the reflux temperature, preferably cooling.

Alternatively, the group $—(CR_5R_{5'})_mX(CR_6R_{6'})_nR_2$ can be incorporated in the last step of the synthesis by reaction of a compound of formula VIIIH with a compound of formula IX, X or XI, as shown in Scheme 1. A compound of formula VIIIH is obtained by deprotection of a compound of formula VIIIP, wherein P represents a suitable protecting group, preferably Boc (tert-butoxycarbonyl). When the protecting group is Boc, the deprotection can be conducted by adding a solution of a strong acid such as HCl, in a suitable solvent such as diethyl ether, 1,4-dioxane or methanol, or with trifluoroacetic acid in dichloromethane. A compound of formula VIIIP is prepared from a compound of formula IIP following the same sequence described for the synthesis of compounds of formula I.

The alkylation reaction between a compound of formula VIIIH (or a suitable salt such as trifluoroacetate or hydrochloride) and a compound of formula IX is carried out in a suitable solvent, such as acetonitrile, dichloromethane, 1,4-dioxane or dimethylformamide, preferably in acetonitrile; in the presence of an inorganic base such as $K_2CO_3$ or $Cs_2CO_3$, or an organic base such as triethylamine or diisopropylethylamine, preferably $K_2CO_3$; at a suitable temperature comprised between room temperature and the reflux temperature, preferably heating, or alternatively, the reactions can be carried out in a microwave reactor. Additionally, an activating agent such as NaI can be used.

The reductive amination reaction between a compound of formula VIIIH and a compound of formula X is carried out in the presence of a reductive reagent, preferably sodium triacetoxyborohydride, in an aprotic solvent, preferably tetrahydrofuran or dichloroethane, optionally in the presence of an acid, preferably acetic acid.

The condensation reaction between a compound of general formula VIIIH and a compound of formula XI is preferably carried out in a suitable solvent, such as ethanol, isopropanol, n-butanol or 2-methoxyethanol, optionally in the presence of an organic base such as triethylamine or diisopropylethylamine, at a suitable temperature comprised between room temperature and the reflux temperature, preferably heating, or alternatively, the reactions can be carried out in a microwave reactor.

In another alternative approach, the $—(CR_4R_{4'})_pR_1$ substituent can be incorporated later in the sequence by the reaction of a compound of formula XIV with a compound of formula XV. Depending on the meaning of Y, V can be of different nature and different reaction conditions will apply:
  a) When Y is $CH_2$, compound XV is an alkylating agent and V represents a leaving group such as halogen, mesylate, tosylate or triflate. The alkylation reaction is carried out under the same reaction conditions described above for the reaction of a compound of formula VIIIH and a compound of formula IX.
  Alternatively, compound XV can be an aldehyde wherein V represents a C(O)—H group. The reductive amination reaction is carried out under the same reaction conditions described above for the reaction of a compound of formula VIIIH and a compound of formula X.
  b) When Y is C(O), compound XV is an alkylating agent and V represents a leaving group such as halogen, mesylate, tosylate or triflate. This alkylation reaction is carried out in an aprotic solvent, preferably dimethylformamide, in the presence of an inorganic base such as NaH, at a suitable temperature, preferably between room temperature and 60° C.

A compound of formula XIV is synthesized following analogous sequence as described for the synthesis of compounds of formula I, but effecting step 2 using ammonia instead of an amine IVa. Alternatively, when Y is C(O), a compound of formula XIV can be prepared by reaction of a compound of formula XIVH (prepared from a compound of formula XIVP, wherein P represents a suitable protecting group) with a compound of formula IX, X or XI, as described above.

Additionally, a compound of formula XIV can be prepared from a compound of formula XVI, wherein P' presents an orthogonal protecting group. When Y is C(O), P' is preferably a 4-methoxybenzyl group and the deprotection reaction is carried out with cerium ammonium nitrate in a suitable solvent such as mixtures of acetonitrile-water or by heating in trifluoroacetic acid or hydrochloric acid. When Y is —CH$_2$—, P' is preferably a 4-methoxybenzyl or a benzyl group, and the deprotection reaction is preferably carried out by hydrogenation under hydrogen atmosphere and metal catalysis, preferably by the use of palladium over charcoal as catalyst in a suitable solvent such as methanol or ethanol, optionally in the presence of an acid such as acetic acid or hydrochloric acid.

A compound of formula XVI is synthesized from a compound of formula III following an analogous sequence as described for the synthesis of compounds of formula I. Alternatively, a compound of formula XVI can be prepared by reaction of a compound of formula XVIIH (prepared from a compound of formula XVIP, wherein P represents a suitable protecting group) with a compound of formula IX, X or XI, as described above.

The compounds of general formula II, IIP, IVa, IVb, VI, IX, X, XI and XV wherein R$_1$, R$_2$, R$_3$, R$_3'$, R$_4$, R$_4'$, R$_5$, R$_5'$, R$_6$, R$_6'$, X, Y, m, n and p have the meaning as described above, are commercially available or can be prepared by conventional methods described in the bibliography.

Scheme 2

The preparation of compounds of general formula (I) wherein Y represents CO and R$_3$ and R$_3'$ are taken together with the connecting C-atom to form a cycloalkyl (compounds of formula Ia) is described in the following scheme:

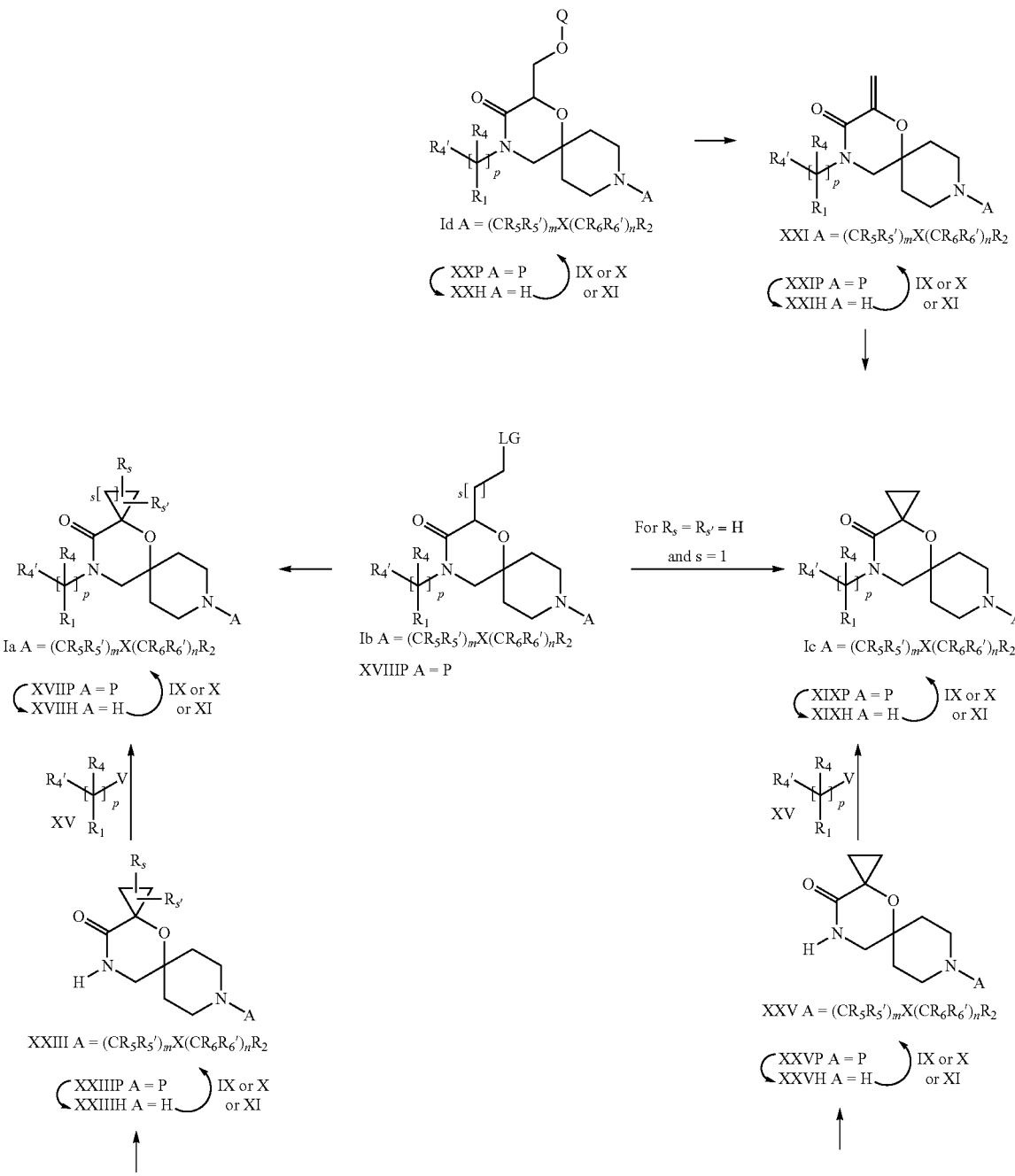

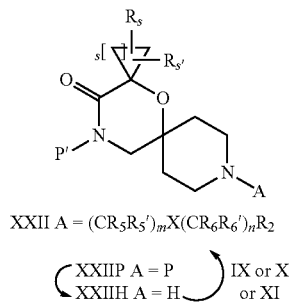

XXII A = (CR$_5$R$_5'$)$_m$X(CR$_6$R$_6'$)$_n$R$_2$ $\begin{pmatrix} \text{XXIIP A = P} \\ \text{XXIIIH A = H} \end{pmatrix}$ IX or X or XI

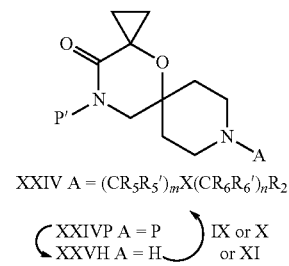

XXIV A = (CR$_5$R$_5'$)$_m$X(CR$_6$R$_6'$)$_n$R$_2$ $\begin{pmatrix} \text{XXIVP A = P} \\ \text{XXVH A = H} \end{pmatrix}$ IX or X or XI

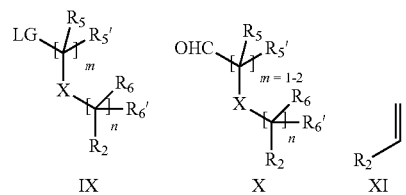

IX     X     XI wherein $R_1$, $R_2$, $R_4$, $R_{4'}$, $R_5$, $R_{5'}$, $R_6$, $R_{6'}$, X, Y, m, n and p have the meanings as defined above for a compound of formula (I), s represents 1, 2, 3 or 4, $R_s$ and $R_{s'}$ represent hydrogen or alkyl, LG represents a leaving group such as halogen, mesylate, tosylate or triflate, V represents another leaving group (such as halogen, mesylate, tosylate or triflate), P represents a suitable protecting grope (preferably Boc), P' represents an orthogonal protecting group (preferably 4-methoxybenzyl), and Q represents methyl or benzyl.

A compound of formula Ia can be prepared from a compound of formula Ib by treatment with a strong base such as lithium diisopropylamide or potassium tert-butoxide, in an aprotic solvent such as tetrahydrofuran, at a suitable temperature, preferably cooling. And analogously, a compound of formula Ic (wherein $R_5=R_{5'}=H$ and s=1) can be prepared from a compound of formula Ib under the same reaction conditions.

Alternatively, compounds of formula Ic can be prepared from compounds of formula XXI. The cyclopropanation reaction is carried out using a suitable methyl-transfer reagent such as trimethylsulfoxonium iodide or trimethylsulfonium iodide, in a suitable aprotic solvent such as dimethylsulfoxide, and in the presence of a strong base such as sodium hydride or potassium tert-butoxide, at a suitable temperature, preferably comprised between room temperature and 60° C. Alternatively, typical Simmons-Smith reaction conditions could be used, comprising the treatment of a compound of formula XXI with diiodomethane, a zinc source such as zinc-copper, zinc iodide or diethylzinc, in a suitable aprotic solvent, such as diethyl ether.

Compounds of formula XXI can be prepared from a compound of formula Id wherein Q represents methyl or benzyl. The elimination reaction is carried out in the presence of a base, such as potassium tert-butoxide, in a suitable solvent, such as tetrahydrofuran.

In another alternative approach, the —(CR$_4$R$_{4'}$)$_p$R$_1$ substituent can be incorporated later in the synthesis. Thus, compounds of formula Ia and Ic can be prepared from compounds of formula XXIII and XXV, respectively, following the reaction conditions described in Scheme 1 for the preparation of compounds of formula I from compounds of formula XIV. The compounds of formula XXIII and XXV can be prepared from suitable protected precursors XXII and XXIV, respectively, following the conditions described in Scheme 1.

In addition, the group —(CR$_5$R$_{5'}$)$_m$X(CR$_6$R$_{6'}$)$_m$R$_2$ can be incorporated in the last step of the synthesis to prepare compounds of formula Ia and Ic from suitable protected precursors, by deprotection followed by reaction with a compound of formula IX or X or XI, as described in Scheme 1 for the preparation of compounds of formula I.

The compounds of general formula Ib and Id can be prepared by the procedures described in Scheme 1 from a compound of formula Va using suitable starting materials. The compounds of general formula XXII and XXIV can be prepared following the procedures described in Scheme 2 for the preparation of compounds of formula Ia and Ic using the corresponding protected starting materials.

Scheme 3 and Scheme 4

Compounds of formula (I) can also be prepared starting from other compounds of formula (I), as described in Schemes 3 and 4 below.

Compounds of formula Ia, If and Ig can be prepared from a compound of formula Ie as shown in Scheme 3:

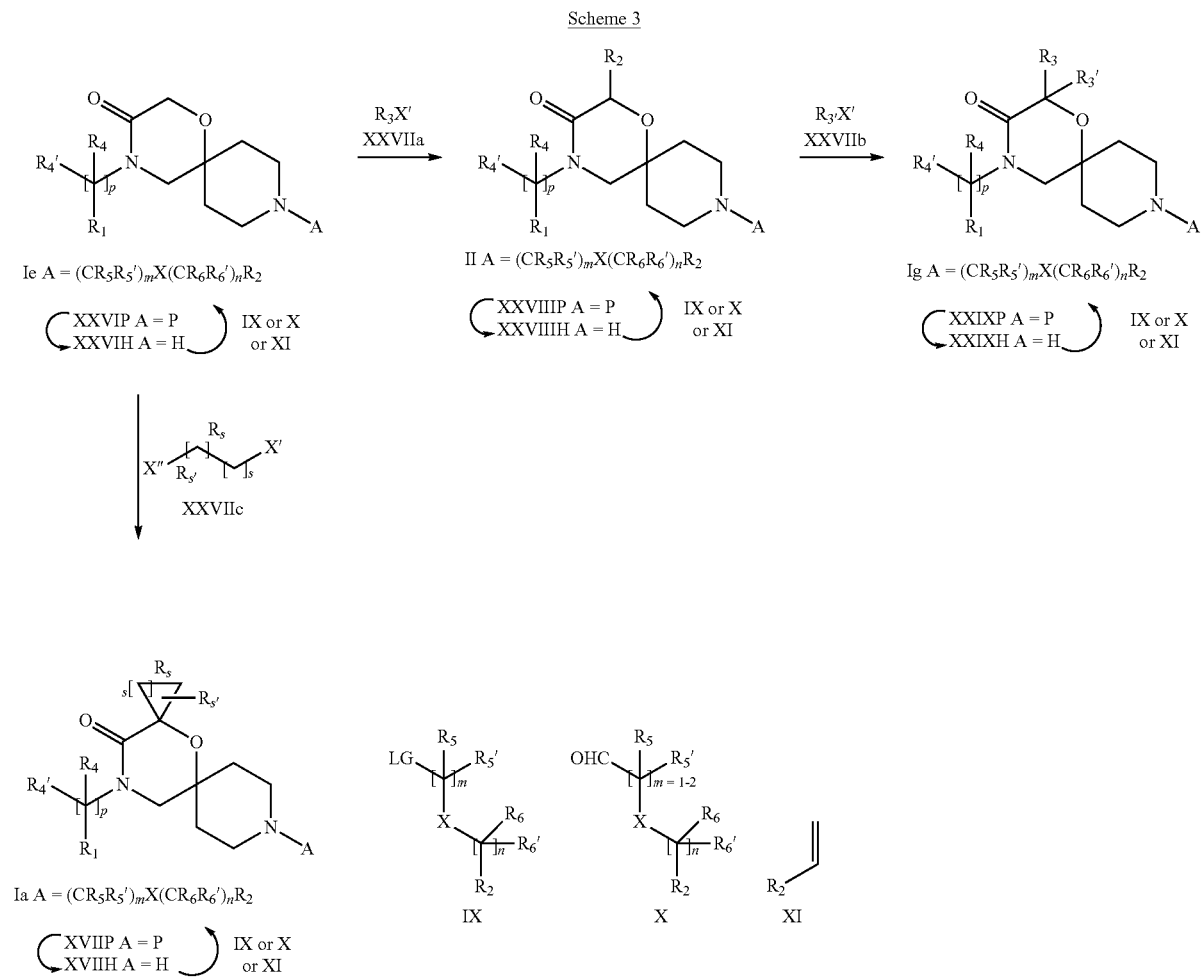

wherein $R_1$, $R_2$, $R_3$, $R_{3'}$, $R_4$, $R_{4'}$, $R_5$, $R_{5'}$, $R_6$, $R_{6'}$, X, m, n and p have the meanings as defined above for a compound of formula (I), s represents 1, 2, 3 or 4, $R_s$ and $R_{s'}$ represent hydrogen or alkyl, LG, X' and X" independently represent a leaving group such as halogen, mesylate, tosylate or triflate, and P represents a suitable protecting group (preferably Boc).

A compound of formula If can be prepared by treating a compound of formula Ie with an alkylating agent of formula XXVIIa in the presence of a strong base such as lithium diisopropylamide or potassium tert-butoxide, in an aprotic solvent such as tetrahydrofuran, at a suitable temperature, preferably comprised between −78° C. and room temperature. A second alkylation can be performed under the same reaction conditions to prepare a compound of formula Ig. An analogous double-alkylation process can be used for the preparation of compounds of formula Ia, by reacting a compound of formula Ie with an alkylating agent of formula XXVIIc, as an alternative to the procedure described in Scheme 2 for the preparation of compounds of formula Ia.

In addition, the group —$(CR_5R_{5'})_mX(CR_6R_{6'})_nR_2$ can be incorporated in the last step of the synthesis to prepare compounds of formula Ia, Ie, If and Ig from suitable protected precursors, by deprotection followed by reaction with a compound of formula IX or X or XI, under the reaction conditions described in Scheme 1 for the preparation of compounds of formula I.

The compounds of general formula Ie and If can be prepared by the procedures described in Scheme 1 using suitable starting materials.

The compounds of general formula XXVIIa, XXVIIb and XXVIIc wherein $R_3$, $R_{3'}$, $R_5$, $R_{5'}$, X', X" and s have the meanings as defined above, are commercially available or can be prepared by conventional methods described in the bibliography.

Scheme 4 shows the preparation of compounds of formula (I) wherein Y is $CH_2$ from compounds of formula (I) wherein Y is C(O):

Scheme 4

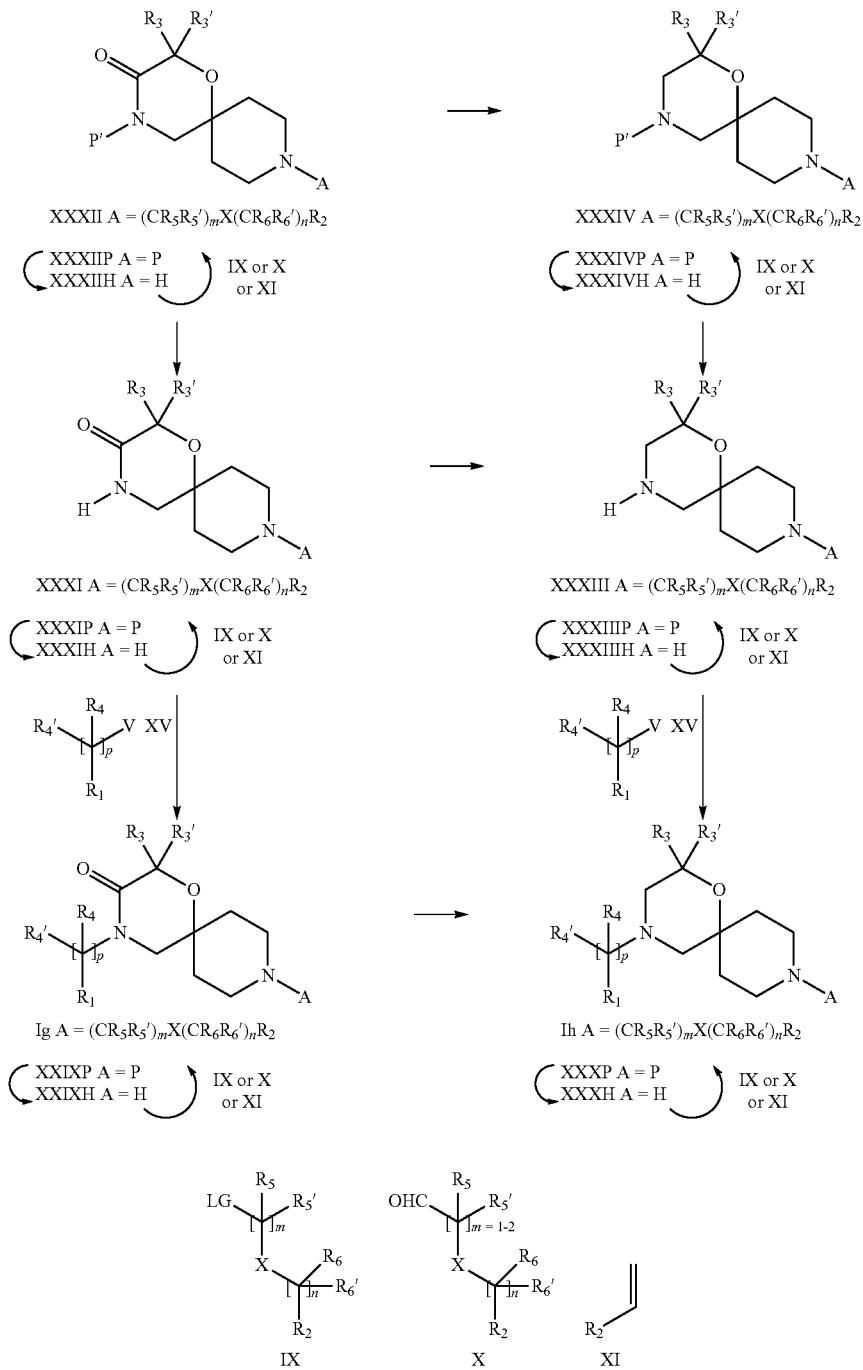

wherein $R_1$, $R_2$, $R_3$, $R_{3'}$, $R_4$, $R_{4'}$, $R_5$, $R_{5'}$, $R_6$, $R_{6'}$, X, m, n and p have the meanings as defined above for a compound of formula (I), LG represents a leaving group such as halogen, mesylate, tosylate or triflate, V represents an aldehyde or another leaving group (such as halogen, mesylate, tosylate or triflate), P represents a suitable protecting group (preferably Boc) and P represents an orthogonal protecting group (preferably 4-methoxybenzyl or benzyl).

The reduction reaction of a compound of formula Ig to yield a compound of formula Ih can be performed using a suitable reducing agent such as lithium aluminium hydride, borane-tetrahydrofuran complex or borane-dimethyl sulphide complex, in a suitable solvent such as tetrahydrofuran or diethyl ether, at a suitable temperature comprised between room temperature and the reflux temperature, preferably heating.

The reduction reaction can also be performed on a suitable precursor (compounds of formula XXXI or XXXII) or a protected derivative (compounds of formula XXIXP, XXXIP or XXXIIP, wherein A=P). When P represents Boc, borane is the preferred reducing agent.

The compounds of general formula Ig can be prepared by the procedures described in Schemes 1 to 3 using suitable starting materials, or they can be prepared from a compound of formula XXXI or XXXII. The deprotection of a compound of formula XXXII to give a compound of formula XXXI and the subsequent reaction with a compound of formula XV to yield a compound of formula Ig are performed following the procedures described in Scheme 1.

The compounds of general formula XXXI and XXXII can be prepared according to the procedures described in Scheme 1 using suitable starting materials.

Accordingly, the compounds of general formula Ih may be prepared from a compound of formula XXXIII or XXXIV following an analogous procedure.

In addition, the group —$(CR_5R_{5'})_mX(CR_6R_{6'})_nR_2$ may be incorporated at different stages of the synthesis to prepare compounds of formula Ig and Ih from suitable protected precursors, by deprotection followed by reaction with a compound of formula IX or X or XI, as described in Scheme 1 for the preparation of compounds of formula I.

Moreover, certain compounds of the present invention can also be obtained starting from other compounds of formula (I) by appropriate conversion reactions of functional groups, in one or several steps, using well-known reactions in organic chemistry under standard experimental conditions.

In addition, a compound of formula I that shows chirality can also be obtained by resolution of a racemic compound of formula I either by chiral preparative HPLC or by crystallization of a diastereomeric salt or co-crystal. Alternatively, the resolution step can be carried out at a previous stage, using any suitable intermediate.

EXAMPLES

Intermediates and Examples

The following abbreviations are used in the examples:
ACN: acetonitrile
AcOH: acetic acid
Boc: tert-butoxycarbonyl
Conc: concentrated
DCM: dichloromethane
DIPEA: N,N-diisopropylethylamine
DMF: dimethylformamide
DMSO: dimethylsulfoxide
EtOH: ethanol
EX: example
h: hour/s
HPLC: high performance liquid chromatography
INT: intermediate
LDA: lithium diisopropylamide
MeOH: methanol
MS: mass spectrometry
Min.: minutes
Quant: quantitative
Ret: retention
r.t.: room temperature
Sat: saturated
s.m.: starting material
TFA: trifluoroacetic acid
THF: tetrahydrofuran
Wt: weight The following methods were used to determine the HPLC-MS spectra:

Method A
Column: Gemini-NX 30×4.6 mm, 3 um
Temperature: 40° C.
Flow: 2.0 mL/min
Gradient: $NH_4HCO_3$ pH 8: ACN (95:5)—0.5 min—(95:5)—6.5 min—(0:100)—1 min—(0:100)
Sample dissolved aprox. 1 mg/mL in $NH_4HCO_3$PH 8/ACN Method B
Column: Xbridge $C_{18}$ XP 30×4.6 mm, 2.5 μm
Temperature: 40° C.
Flow: 2.0 mL/min
Gradient: $NH_4HCO_3$ pH 8: ACN (95:5)—0.5 min—(95:5)—6.5 min—(0:100)—1 min—(0:100)
Sample dissolved aprox. 1 mg/ml in $NH_4HCO_3$PH 8/ACN Method C
Column: Kinetex EVO 50×4.6 mm 2.6 um
Temperature: 40° C.
Flow. 2.0 mL/min
Gradient: $NH_4HCO_3$ pH 8: ACN (95:5)—0.5 min—(95:5)—6.5 min—(0:100)—1 min—(0:100)
Sample dissolved aprox. 1 mg/mL in $NH_4HCO_3$PH 8/ACN Method D
Column: Kinetex EVO 50×4.6 mm 2.6 um
Temperature: 40° C.
Flow: 1.5 mL/min
Gradient: $NH_4HCO_3$ pH 8: ACN (95:5)—0.5 min—(95:5)—6.5 min—(0:100)—2 min—(0:100)
Sample dissolved aprox. 1 mg/mL in $NH_4HCO_3$PH 8/ACN Synthesis of Intermediates Intermediate 1A: tert-Butyl 1-oxa-6-azaspiro[2.5]octane-6-carboxylate

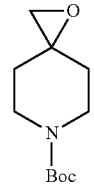

To a suspension of trimethylsulfoxonium iodide (24.3 g, 110 mmol) and NaH (4.4 g, 60 wt % in mineral oil, 110 mmol) in DMSO (140 mL), a solution of tert-butyl 4-oxopiperidine-1-carboxylate (20.0 g, 100 mmol) in DMSO (140 mL) was added dropwise. The reaction mixture was stirred at r.t. for 30 min, then heated at 50° C. for 1 h. After cooling to r.t., ice was slowly added, and the reaction mixture was extracted three times with ethyl acetate. The organic phases were combined, washed with water, dried over $MgSO_4$ and concentrated under vacuum to give the title compound (17.6 g, 82% yield) as a white solid.

This method was used for the preparation of intermediate 1B using suitable starting materials:

| INT | Structure | Chemical name | s.m. |
|---|---|---|---|
| 1B | 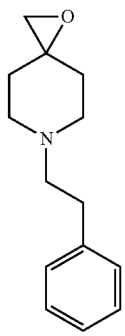 [SMILES: c1ccc(CCN2CCC3(CC2)CO3)cc1] | 6-phenethyl-1-oxa-6-azaspiro[2.5]octane | 1-phenethyl-piperidin-4-one |

Intermediate 2A: tert-Butyl 4-hydroxy-4-((methylamino)methyl)piperidine-1-carboxylate

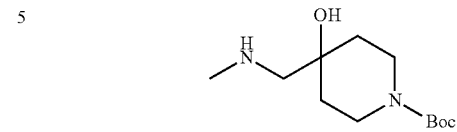

To a solution of intermediate 1A (0.50 g, 2.34 mmol) in a mixture of EtOH-water 5.5:1 (14 mL), methylamine (4.1 mL, 40% solution in water, 47 mmol) was added. The reaction mixture was stirred at r.t. overnight in a sealed tube. The solvent was removed under vacuum to give the title compound (0.534 g, 93% yield) as a white solid.

This method was used for the preparation of intermediates 2B-2I using suitable starting materials:

| INT | Structure | Chemical name | s.m. |
|---|---|---|---|
| 2B | 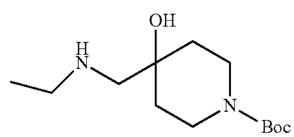 [SMILES: CCNCC1(O)CCN(C(=O)OC(C)(C)C)CC1] | tert-butyl 4-((ethylamino)methyl)-4-hydroxypiperidine-1-carboxylate | 1A |
| 2C | 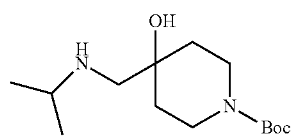 [SMILES: CC(C)NCC1(O)CCN(C(=O)OC(C)(C)C)CC1] | tert-butyl 4-hydroxy-4-((isopropylamino)methyl)piperidine-1-carboxylate | 1A |
| 2D | 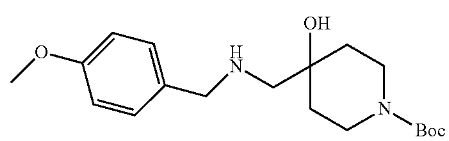 [SMILES: COc1ccc(CNCC2(O)CCN(C(=O)OC(C)(C)C)CC2)cc1] | tert-butyl 4-hydroxy-4-(((4-methoxybenzyl)amino)methyl)piperidine-1-carboxylate | 1A |
| 2E | 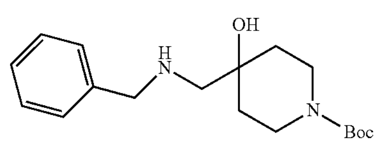 [SMILES: CC(C)(C)OC(=O)N1CCC(O)(CNCc2ccccc2)CC1] | tert-butyl 4-((benzylamino)methyl)-4-hydroxypiperidine-1-carboxylate | 1A |
| 2F | 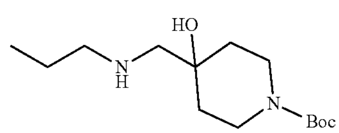 [SMILES: CCCNCC1(O)CCN(C(=O)OC(C)(C)C)CC1] | tert-butyl 4-hydroxy-4-((propylamino)methyl)piperidine-1-carboxylate | 1A |
| 2G | 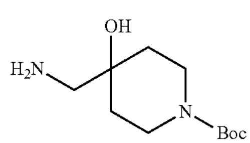 [SMILES: CC(C)(C)OC(=O)N1CCC(O)(CN)CC1] | tert-butyl 4-(aminomethyl)-4-hydroxypiperidine-1-carboxylate | 1A |
| 2H | 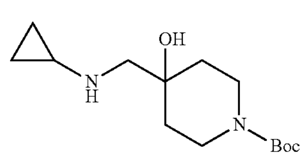 [SMILES: CC(C)(C)OC(=O)N1CCC(O)(CNC2CC2)CC1] | tert-butyl 4-((cyclopropylamino)methyl)-4-hydroxypiperidine-1-carboxylate | 1A |

| INT | Structure | Chemical name | s.m. |
|---|---|---|---|
| 2I | H$_2$N–CH$_2$–[4-hydroxypiperidine with N-CH$_2$CH$_2$-phenyl] | 4-(aminomethyl)-1-phenethylpiperidin-4-ol | 1B |

Intermediate 3A: tert-Butyl 12-(4-methoxybenzyl)-13-oxo-4-oxa-8,12-diazadispiro [2.1.5.3]tridecane-8-carboxylate

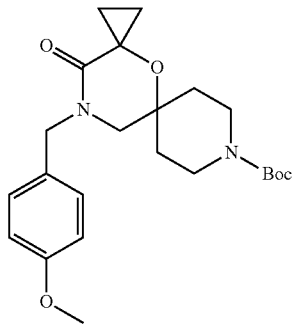 [SMILES: COc1ccc(CN2CC3(CCN(C(=O)OC(C)(C)C)CC3)OC3(CC3)C2=O)cc1]

Step 1. tert-Butyl 4-((2-bromo-4-chloro-N-(4-methoxybenzyl)butanamido)methyl)-4-hydroxypiperidine-1-carboxylate: To a solution of intermediate 2D (9.94 g, 28.4 mmol) and triethylamine (9.5 mL, 68.1 mmol) in DCM (500 mL), a solution of 2-bromo-4-chlorobutanoyl chloride (prepared as described in U.S. Pat. No. 6,114,541 A1 (2000) Ex1) (9.35 g, 20.2 mmol) in DCM (200 mL) was added dropwise at 0° C. The reaction mixture was stirred at 0° C. for 3 h. DCM and NaHCO$_3$ aqueous sat. solution were added and the phases were separated. The aqueous phase was extracted with DCM and the organic phases were combined, dried over MgSO$_4$, filtered and concentrated to dryness, to give the title compound (17.6 g, crude product).

Step 2. Title compound: A solution of the crude product obtained in step 1 (14.8 g, 27.7 mmol) in THF (185 mL) was cooled under nitrogen to 0° C. After addition of potassium tert-butoxide solution (111 mL, 1M in THF, 111 mmol), the reaction mixture was stirred at 0° C. for 2 h. NH$_4$Cl sat solution was then added, and the aqueous phase was extracted with ethyl acetate. The organic phases were combined, dried over MgSO$_4$, filtered and concentrated under vacuum. The residue was purified by flash chromatography, silica gel, gradient DCM to MeOH/DCM (1:4) to give the title compound (5.51 g, 48% yield for the 2 steps).

This method was used for the preparation of intermediates 3B-3E using suitable starting materials:

| INT | Structure | Chemical name | s.m. |
|---|---|---|---|
| 3B | [structure] | tert-butyl 12-isopropyl-13-oxo-4-oxa-8,12-diazadispiro[2.1.5.3]tridecane-8-carboxylate | 2C |
| 3C | [structure] | tert-butyl 12-ethyl-13-oxo-4-oxa-8,12-diazaspiro[2.1.5.3]tridecane-8-carboxylate | 2B |
| 3D | [structure] | tert-butyl 12-methyl-13-oxo-4-oxa-8,12-diazadispiro[2.1.5.3]tridecane-8-carboxylate | 2A |

| INT | Structure | Chemical name | s.m. |
|---|---|---|---|
| 3E | 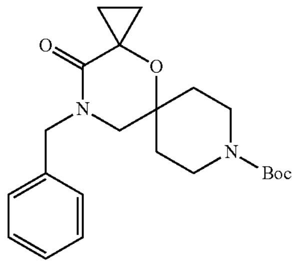 [SMILES: CC(C)(C)OC(=O)N1CCC2(CC1)CN(Cc1ccccc1)C(=O)C1(CC1)O2] | tert-butyl 12-benzyl-13-oxo-4-oxa-8,12-diazadispiro[2.1.5.3]tridecane-8-carboxylate | 2E |

Intermediate 4: tert-Butyl 13-oxo-4-oxa-8,12-diazadispiro[2.1.5.3]tridecane-8-carboxylate

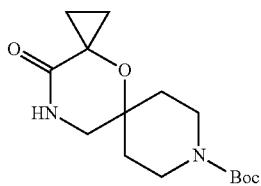 [SMILES: CC(C)(C)OC(=O)N1CCC2(CC1)CNC(=O)C1(CC1)O2]

Step 1. 4-Oxa-8,12-diazadispiro[2.1.5.3]tridecan-13-one trifluoroacetate: A solution of intermediate 3A (1.78 g, 4.26 mmol) in TFA (20 ml) was stirred in a sealed tube at 80° C. for 4 days. The reaction mixture was concentrated to dryness and water was added to the residue. The acidic aqueous phase was washed with ethyl ether, which was discarded. The aqueous layer was evaporated to dryness to give the title compound (1.17 g).

Step 2. Title compound: A mixture of the crude product obtained in step 1, di-tert-butyl dicarbonate (1.40 g, 6.40 mmol), 1,4-dioxane (40 mL) and 1M NaOH aqueous solution (10 mL) was stirred at r.t. overnight. Water was added and the resulting mixture was extracted with ethyl acetate. The organic phases were combined, cried over MgSO$_4$, filtered and concentrated to dryness. The residue was purified by flash chromatography, silica gel, gradient DCM to MeOH/DCM (1:4) to give the title compound (0.872 g, 69% yield for the 2 steps).

Intermediate 5A: tert-Butyl 13-oxo-12-propyl-4-oxa-8,12-diazadispiro[2.1.5.3]tridecane-8-carboxylate

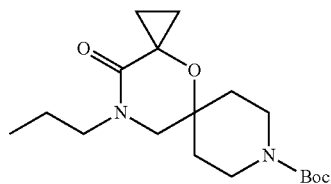 [SMILES: CCCN1CC2(CCN(C(=O)OC(C)(C)C)CC2)OC2(CC2)C1=O]

To a solution of intermediate 4 (0.200 g, 0.641 mmol) in dry DMF (6.7 mL), NaH (54 mg, 60 wt % in mineral oil, 1.35 mmol) was added at 0° C. The reaction mixture was stirred at 0° C. for 30 min, then 1-bromopropane (0.092 mL, 1.012 mmol) was added and the resulting mixture was stirred at r.t. for 3 h. NaHCO$_3$ aqueous sat. solution was added to the reaction mixture and it was extracted with ethyl acetate. The organic phases were combined, washed with brine, dried over MgSO$_4$, filtered and concentrated to dryness to give the title compound as a crude product that was used as such (229 mg, quant. yield).

This method was used for the preparation of intermediates 5B<5F using suitable starting materials:

| INT | Structure | Chemical name | s.m. |
|---|---|---|---|
| 5B | 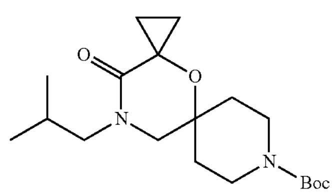 [SMILES: CC(C)CN1CC2(CCN(C(=O)OC(C)(C)C)CC2)OC2(CC2)C1=O] | tert-butyl 12-isobutyl-13-oxo-4-oxa-8,12-diazadispiro[2.1.5.3]tridecane-8-carboxylate | 4 |
| 5C | 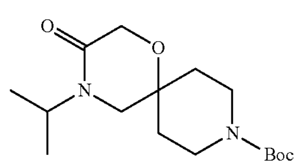 [SMILES: CC(C)N1CC2(CCN(C(=O)OC(C)(C)C)CC2)OCC1=O] | tert-butyl 4-isopropyl-3-oxo-1-oxa-4,9-diazaspiro[5.5]undecane-9-carboxylate | tert-butyl 3-oxo-1-oxa-4,9-diazaspiro[5.5]undecane-9-carboxylate |

| INT | Structure | Chemical name | s.m. |
|---|---|---|---|
| 5D | 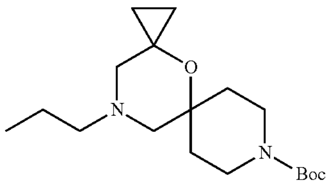 [SMILES: CCCN1CC2(CCN(C(=O)OC(C)(C)C)CC2)OC2(CC2)C1] | tert-butyl 12-propyl-4-oxa-8,12-diazadispiro[2.1.5.3]tridecane-8-carboxylate | 8 |
| 5E | 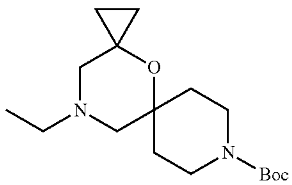 [SMILES: CCN1CC2(CCN(C(=O)OC(C)(C)C)CC2)OC2(CC2)C1] | tert-butyl 12-ethyl-4-oxa-8,12-diazadispiro[2.1.5.3]tridecane-8-carboxylate | 8 |
| 5F | 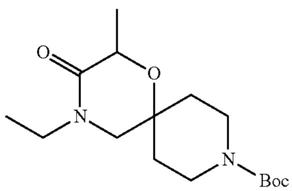 [SMILES: CCN1CC2(CCN(C(=O)OC(C)(C)C)CC2)O[C@@H](C)C1=O] | tert-butyl 4-ethyl-2-methyl-3-oxo-1-oxa-4,9-diazaspiro[5.5]undecane-9-carboxylate | 6N |

Intermediate 6A: (S)-tert-Butyl 4-ethyl-2-methyl-3-oxo-1-oxa-4,9-diazaspiro[5.5]undecane-9-carboxylate

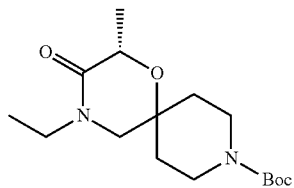

Step 1. (R)-tert-Butyl 4-((2-chloro-N-methylpropanamido)methyl)-4-hydroxypiperidine-1-carboxylate. To a solution of intermediate 2B (0.700 g, 2.71 mmol) in ethyl acetate (7 mL), a solution of K₂CO₃ (1.05 g, 7.59 mmol) in water (7.7 mL) was added. After cooling to 0° C., a solution of (R)-2-chloropropanoyl chloride (0.461 g, 3.63 mmol) in ethyl acetate (3.5 mL) was added dropwise. The reaction mixture was stirred at 0-5° C. for 30 min and then it was diluted with water. The layers were separated and the aqueous phase was extracted with ethyl acetate. The organic phases were combined, washed with 0.5 M HCl aqueous solution and then NaHCO₃ sat solution, dried over MgSO₄, filtered and concentrated to dryness to give the title compound (0.775 g, 82% yield).

Step 2. Title compound: A solution of the crude product obtained in step 1 (0.775 g, 2.22 mmol) in THF (15.5 mL) was cooled to −78° C. using a dry ice/acetone bath. After addition of potassium tert-butoxide solution (2.4 mL, 1M in THF, 2.4 mmol), the reaction mixture was stirred at −78° C. for 30 min. NH₄Cl sat solution was then added, and the aqueous phase was extracted with ethyl acetate. The organic phases were combined, dried over MgSO₄, filtered and concentrated under vacuum to give the title compound (0.683 g, 98% yield).

This method was used for the preparation of intermediates 6B-6P using suitable starting materials:

| INT | Structure | Chemical name | s.m. |
|---|---|---|---|
| 6B | 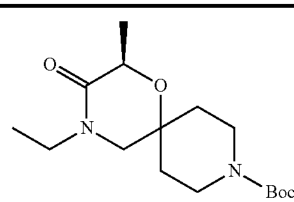 | (R)-tert-butyl 4-ethyl-2-methyl-3-oxo-1-oxa-4,9-diazaspiro[5.5]undecane-9-carboxylate | 2B |
| 6C | 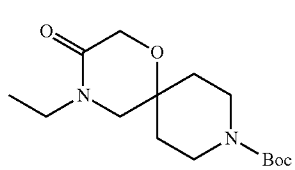 [SMILES: CCN1CC2(CCN(C(=O)OC(C)(C)C)CC2)OCC1=O] | tert-butyl 4-ethyl-3-oxo-1-oxa-4,9-diazaspiro[5.5]undecane-9-carboxylate | 2B |

| INT | Structure | Chemical name | s.m. |
|---|---|---|---|
| 6D | 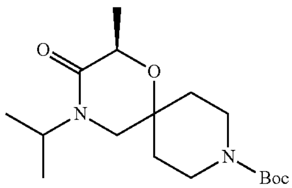 [SMILES: CC(C)N1CC2(CCN(C(=O)OC(C)(C)C)CC2)O[C@H](C)C1=O] | (R)-tert-butyl 4-isopropyl-2-methyl-3-oxo-1-oxa-4,9-diazaspiro[5.5]undecane-9-carboxylate | 2C |
| 6E | 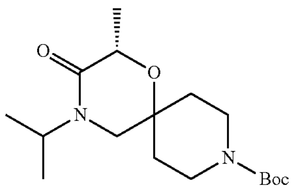 [SMILES: CC(C)N1CC2(CCN(C(=O)OC(C)(C)C)CC2)O[C@@H](C)C1=O] | (S)-tert-butyl 4-isopropyl-2-methyl-3-oxo-1-oxa-4,9-diazaspiro[5.5]undecane-9-carboxylate | 2C |
| 6F | 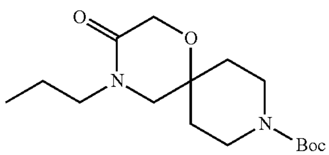 [SMILES: CCCN1CC2(CCN(C(=O)OC(C)(C)C)CC2)OCC1=O] | tert-butyl 3-oxo-4-propyl-1-oxa-4,9-diazaspiro[5.5]undecane-9-carboxylate | 2F |
| 6G | 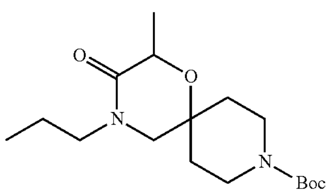 [SMILES: CCCN1CC2(CCN(C(=O)OC(C)(C)C)CC2)OC(C)C1=O] | tert-butyl 2-methyl-3-oxo-4-propyl-1-oxa-4,9-diazaspiro[5.5]undecane-9-carboxylate | 2F |
| 6H | 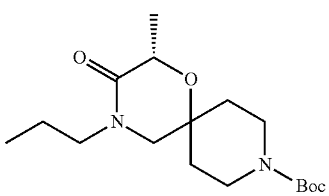 [SMILES: CCCN1CC2(CCN(C(=O)OC(C)(C)C)CC2)O[C@@H](C)C1=O] | (S)-tert-butyl 2-methyl-3-oxo-4-propyl-1-oxa-4,9-diazaspiro[5.5]undecane-9-carboxylate | 2F |
| 6I | 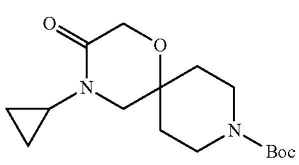 [SMILES: CC(C)(C)OC(=O)N1CCC2(CC1)CN(C1CC1)C(=O)CO2] | tert-butyl 4-cyclopropyl-3-oxo-1-oxa-4,9-diazaspiro[5.5]undecane-9-carboxylate | 2H |
| 6J | 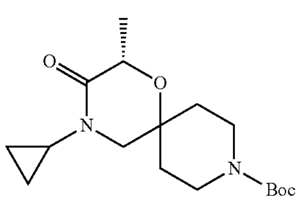 [SMILES: C[C@@H]1OC2(CCN(C(=O)OC(C)(C)C)CC2)CN(C2CC2)C1=O] | (S)-tert-butyl 4-cyclopropyl-2-methyl-3-oxo-1-oxa-4,9-diazaspiro[5.5]undecane-9-carboxylate | 2H |
| 6K | 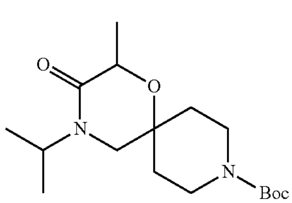 [SMILES: CC1OC2(CCN(C(=O)OC(C)(C)C)CC2)CN(C(C)C)C1=O] | tert-butyl 4-isopropyl-2-methyl-3-oxo-1-oxa-4,9-diazaspiro[5.5]undecane-9-carboxylate | 2C |

-continued

| INT | Structure | Chemical name | s.m. |
|---|---|---|---|
| 6L | 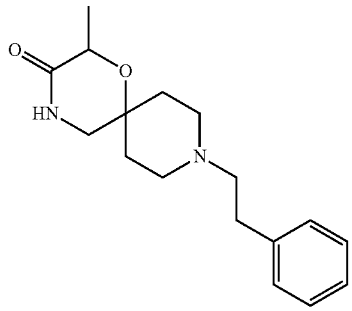 [SMILES: CC1OC2(CCN(CCc3ccccc3)CC2)CNC1=O] | 2-methyl-9-phenethyl-1-oxa-4,9-diazaspiro[5.5]undecan-3-one | 2I |
| 6M | 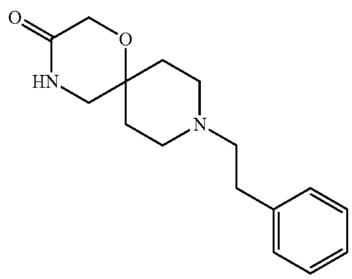 [SMILES: O=C1COC2(CCN(CCc3ccccc3)CC2)CN1] | 9-phenethyl-1-oxa-4,9-diazaspiro[5.5]undecan-3-one | 2I |
| 6N | 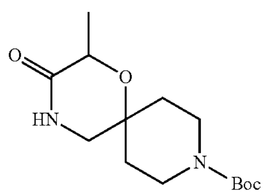 [SMILES: CC1OC2(CCN(C(=O)OC(C)(C)C)CC2)CNC1=O] | tert-butyl 2-methyl-3-oxo-1-oxa-4,9-diazaspiro[5.5]undecane-9-carboxylate | 2G |
| 6O | 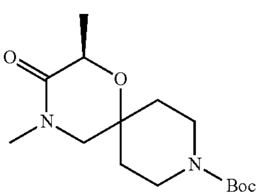 [SMILES: C[C@H]1OC2(CCN(C(=O)OC(C)(C)C)CC2)CN(C)C1=O] | (R)-tert-butyl 2,4-dimethyl-3-oxo-1-oxa-4,9-diazaspiro[5.5]undecane 9-carboxylate | 2A |
| 6P | 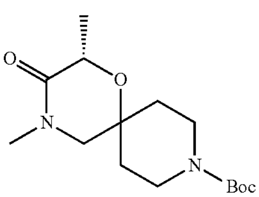 [SMILES: C[C@@H]1OC2(CCN(C(=O)OC(C)(C)C)CC2)CN(C)C1=O] | (S)-tert-butyl 2,4-dimethyl-3-oxo-1-oxa-4,9-diazaspiro[5.5]undecane-9-carboxylate | 2A |

Intermediate 7A: tert-Butyl 12-isopropyl-4-oxa-8,12-diazadispiro[2.1.5.3]tridecane-8-carboxylate

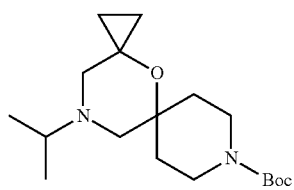 [SMILES: CC(C)N1CC2(CCN(C(=O)OC(C)(C)C)CC2)OC2(CC2)C1]

To a solution of intermediate 3B (1.00 g, 2.95 mmol) in THF (5 ml), borane-tetrahydrofuran complex solution (11.8 mL, 1M in THF, 11.8 mmol) was added dropwise at r.t. The reaction mixture was stirred at 65° C. for 2 h, then it was cooled to r.t., 1M NaOH aqueous sol (5 mL) was carefully added, cooling the mixture with an ice-water bath, and then it was heated to 70° C. for 2 h. After cooling to r.t., it was diluted with ethyl acetate. The phases were separated and the aqueous phase was back extracted with ethyl acetate. The organic phases were combined, dried over MgSO₄, filtered and concentrated to dryness to give the title compound as a crude product that was used as such (960 mg, quant. yield).

The method was used for the preparation of intermediates 7B-7H using suitable stating materials:

| INT | Structure | Chemical name | s.m. |
|---|---|---|---|
| 7B | 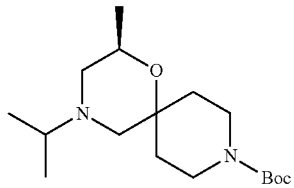 [SMILES: CC(C)N1C[C@@H](C)OC2(CCN(C(=O)OC(C)(C)C)CC2)C1] | (R)-tert-butyl 4-isopropyl-2-methyl-1-oxa-4,9-diazaspiro[5.5]undecane-9-carboxylate | 6D |
| 7C | 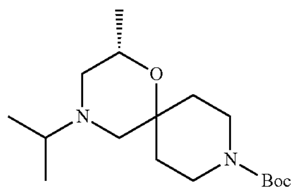 [SMILES: CC(C)N1C[C@H](C)OC2(CCN(C(=O)OC(C)(C)C)CC2)C1] | (S)-tert-butyl 4-isopropyl-2-methyl-1-oxa-4,9-diazaspiro[5.5]undecane-9-carboxylate | 6E |
| 7D | 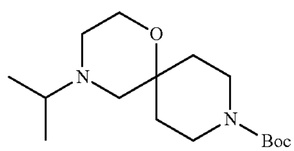 [SMILES: CC(C)N1CCOC2(CCN(C(=O)OC(C)(C)C)CC2)C1] | tert-butyl 4-isopropyl-1-oxa-4,9-diazaspiro[5.5]undecane-9-carboxylate | 5C |
| 7E | 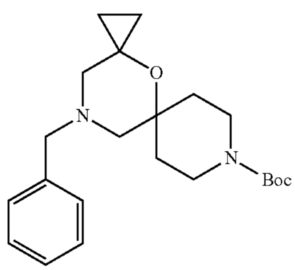 [SMILES: CC(C)(C)OC(=O)N1CCC2(CC1)CN(Cc1ccccc1)CC1(CC1)O2] | tert-butyl 12-benzyl-4-oxa-8,12-diazadispiro[2.1.5.3]tridecane-8-carboxylate | 3E |
| 7F | 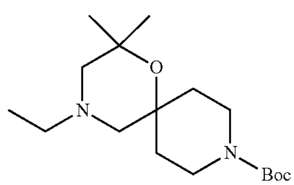 [SMILES: CCN1CC(C)(C)OC2(CCN(C(=O)OC(C)(C)C)CC2)C1] | tert-butyl 4-ethyl-2,2-dimethyl-1-oxa-4,9-diazaspiro[5.5]undecane-9-carboxylate | 9A |
| 7G | 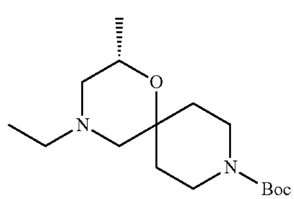 [SMILES: CCN1C[C@H](C)OC2(CCN(C(=O)OC(C)(C)C)CC2)C1] | (S)-tert-butyl 4-ethyl-2-methyl-1-oxa-4,9-diazaspiro[5.5]undecane-9-carboxylate | 6A |
| 7H | 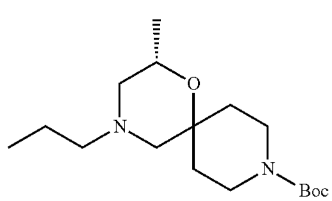 [SMILES: CCCN1C[C@H](C)OC2(CCN(C(=O)OC(C)(C)C)CC2)C1] | (S)-tert-butyl 2-methyl-4-propyl-1-oxa-4,9-diazaspiro[5.5]undecane-9-carboxylate | 6H |

Intermediate 8: tert-Butyl 4-oxa-8,12-diazadispiro[2.1.5.3]tridecane-8-carboxylate

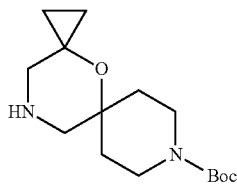

A mixture of intermediate 7E (7.4 g, 19.9 mmol), AcOH (1.14 mL, 19.9 mmol) and palladium (1.31 g, 10% wt on carbon, wet) in MeOH (37 mL) was stirred under 3 bars of H₂ at r.t. for 1 day. The solids were filtered off and the solvent was removed under vacuum. The residue was diluted with DCM and 1M NaOH aqueous solution. The phases were separated and the aqueous phase was extracted several times with DCM. The organic phases were combined, dried over MgSO₄, filtered and concentrated to dryness. The residue was purified by flash chromatography, silica gel, gradient DCM to MeOH/DCM (1:4) to give the title compound (3.57 g, 64% yield).

Intermediate 9A: tert-Butyl 4-ethyl-2,2-dimethyl-3-oxo-1-oxa-4,9-diazaspiro[5.5]undecane-9-carboxylate

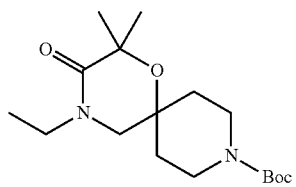 [SMILES: CCN1CC2(CCN(C(=O)OC(C)(C)C)CC2)OC(C)(C)C1=O]

A solution of intermediate 6B (18.15 g, 58.1 mmol) in dry THF (82 mL) was cooled to 0° C. After slow addition of LDA solution (77 mL, 1.5M in THF/n-heptane/ethylbenzene, 115.5 mmol), the reaction mixture was stirred at 0° C. for 30 min. Iodomethane (10.9 mL, 174.2 mmol) was then added and the reaction mixture was stirred at 0-5° C. for further 60 min. Again, LDA solution (77 mL, 1.5M in THF/n-heptane/ethylbenzene. 115.5 mmol), was slowly added and the reaction mixture was stirred at 0° C. for 30 min. Additional iodomethane (10.9 mL, 174.2 mmol) was then added and the reaction mixture was stirred at 0-5° C. for additional 60 min to achieve full conversion. NH₄Cl sat solution was then added, and the aqueous phase was extracted three times with ethyl acetate. The combined organic phases were dried over Na₂SO₄, filtered and concentrated under vacuum. The residue was purified by flash chromatography, silica gel, gradient DCM to MeOH/DCM (1:4) to give the title compound (8.42 g, 44% yield).

This method was used for the preparation of intermediates 9B-9C using suitable starting materials:

| INT | Structure | Chemical name | s.m. |
|---|---|---|---|
| 9B | 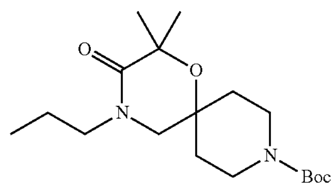 [SMILES: CCCN1CC2(CCN(C(=O)OC(C)(C)C)CC2)OC(C)(C)C1=O] | tert-butyl 2,2-dimethyl-3-oxo-4-propyl-1-oxa-4,9-diazaspiro[5.5]undecane-9-carboxylate | 6G |
| 9C | 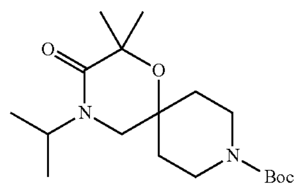 [SMILES: CC(C)N1CC2(CCN(C(=O)OC(C)(C)C)CC2)OC(C)(C)C1=O] | tert-butyl 4-isopropyl-2,2-dimethyl-3-oxo-1-oxa-4,9-diazaspiro[5.5]undecane-9-carboxylate | 6K |

Intermediate 10A: tert-Butyl 12-isobutyl-4-oxa-8,12-diazadispiro[2.1.5.3]tridecane-8-carboxylate

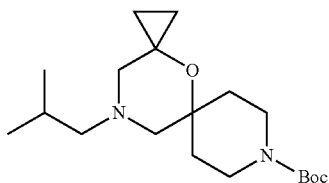 [SMILES: CC(C)CN1CC2(CCN(C(=O)OC(C)(C)C)CC2)OC2(CC2)C1]

A mixture of intermediate 8 (1.5 g, 5.31 mmol), 1-bromo-2-methylpropane (0.69 mL, 6.37 mmol) and K₂CO₃ (1.468 g, 10.62 mmol) in ACN (18 mL) was heated at 80° C. in a sealed tube overnight. 1M NaOH was added, and the reaction mixture was extracted with ethyl acetate. The organic phases were combined, washed with brine, dried over MgSO₄, filtered and concentrated to dryness. The residue was purified by flash chromatography, silica gel, gradient DCM to MeOH/DCM (1:4) to give the title compound (679 mg, 38% yield).

This method was used for the preparation of intermediate 10B using suitable starting materials:

| INT | Structure | Chemical name | s.m. |
|---|---|---|---|
| 10B | 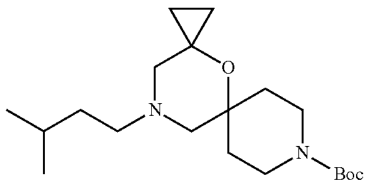 [SMILES: CC(C)CCN1CC2(CCN(C(=O)OC(C)(C)C)CC2)OC2(CC2)C1] | tert-butyl 12-isopentyl-4-oxa-8,12-diazadispiro[2.1.5.3]tridecane-8-carboxylate | 8 |

Intermediate 11A: tert-Butyl 12-neopentyl-4-oxa-8,12-diazadispiro[2.1.5.3]tridecane-8-carboxylate

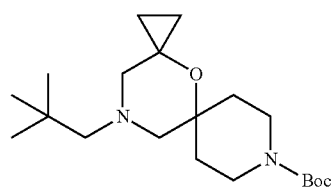 [SMILES: CC(C)(C)CN1CC2(CCN(C(=O)OC(C)(C)C)CC2)OC2(CC2)C1]

To a solution of intermediate 8 (0.300 g, 1.06 mmol) in dry THF (7.2 mL), pivalaldehyde (0.15 mL, 1.38 mmol) and acetic acid (0.12 mL, 2.12 mmol) were added. The reaction mixture was stirred at r.t. for 15 min, and then sodium triacetoxyborohydride (0.675 g, 3.19 mmol) was added in portions. The resulting mixture was stirred at r.t. overnight. Water and $NH_3$ conc were carefully added and it was extracted with ethyl acetate. The organic phases were combined, washed with brine, dried over $Na_2SO_4$, filtered and concentrated to dryness. The residue was purified by flash chromatography, silica gel, gradient DCM to MeOH:DCM (1:4) to give the title compound (184 mg, 49% yield).

This method was used for the preparation of intermediate 11B using suitable starting materials.

| INT | Structure | Chemical name | s.m. |
|---|---|---|---|
| 11B | 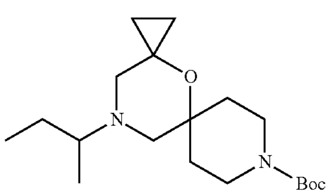 [SMILES: CCC(C)N1CC2(CCN(C(=O)OC(C)(C)C)CC2)OC2(CC2)C1] | tert-butyl 12-(sec-butyl)-4-oxa-8,12-diazadispiro[2.1.5.3]tridecane-8-carboxylate | 8 |

SYNTHESIS OF EXAMPLES

Example 1: 12-Ethyl-8-isopentyl-4-oxa-8,12-diazadispiro[2.1.5.3]tridecan-13-one

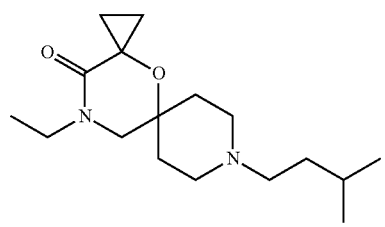 [SMILES: CCN1CC2(CCN(CCC(C)C)CC2)OC2(CC2)C1=O]

Step 1. 12-Ethyl-4-oxa-8,12-diazadispiro[2.1.5.3]tridecan-13-one trifluoroacetate. To a solution of intermediate 3C (1.75 g, 5.39 mmol) in DCM (65 mL), TFA (4.2 mL, 53.9 mmol) was added, and the reaction mixture was heated at 40° C. for 2 h. The solvent was evaporated to dryness to give the title compound as a crude product (3.59 g, 50 wt %, quant yield), that was used in the following step without further purification.

Step 2. Title compound: A mixture of the crude product obtained in step 1 (0.200 g, 50 wt %, 0.297 mmol), 1-bromo-3-methylbutane (0.043 mL, 0.357 mmol), NaI (0.026 g, 0.178 mmol) and $K_2CO_3$ (0.205 g, 1.49 mmol) in ACN (2.5 mL) was heated at 80° C. in a sealed tube overnight. Water was added, and the reaction mixture was extracted with ethyl acetate. The organic phases were combined, washed with brine, dried over $MgSO_4$, filtered and concentrated to dryness. The residue was purified by flash chromatography, silica gel, gradient DCM to MeOH/DCM (1:4) to give the title compound (45 mg, 51% yield).

HPLC retention time (method B): 3.48 min; MS: 295.2 (M+H).

This method was used for the preparation of examples 2-15 using suitable starting materials:

| EX | Structure | Chemical name | Ret time (min) | MS (M + H) |
|---|---|---|---|---|
| 2 | 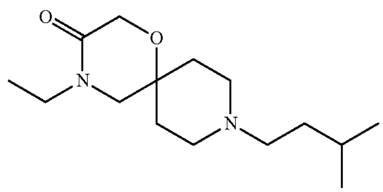 [SMILES: CCN1CC2(CCN(CCC(C)C)CC2)OCC1=O] | 4-ethyl-9-isopentyl-1-oxa-4,9-diazaspiro[5.5]undecan-3-one | 2.26 (method A) | 269.2 |
| 3 | 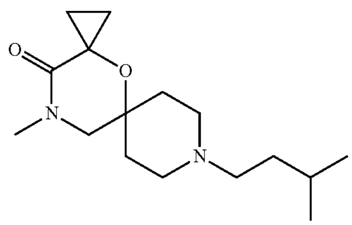 [SMILES: CC(C)CCN1CCC2(CC1)CN(C)C(=O)C1(CC1)O2] | 8-isopentyl-12-methyl-4-oxa-8,12-diazadispiro[2.1.5.3]tridecan-13-one | 2.52 (method A) | 281.2 |
| 4 | 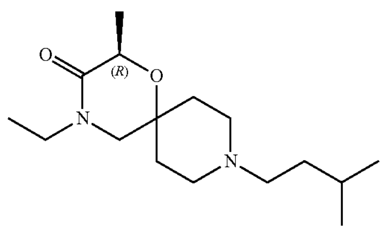 | (R)-4-ethyl-9-isopentyl-2-methyl-1-oxa-4,9-diazaspiro[5.5]undecan-3-one | 2.2 (method A) | 283.2 |
| 5 | 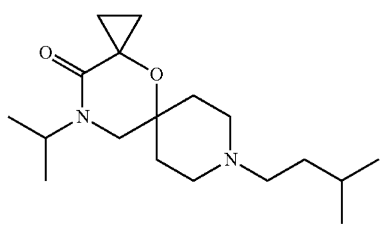 [SMILES: CC(C)CCN1CCC2(CC1)CN(C(C)C)C(=O)C1(CC1)O2] | 8-isopentyl-12-isopropyl-4-oxa-8,12-diazadispiro[2.1.5.3]tridecan-13-one | 3.79 (method A) | 309.2 |
| 6 | 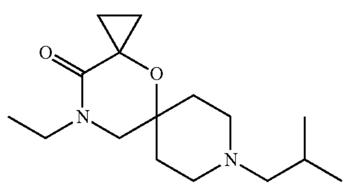 [SMILES: CCN1CC2(CCN(CC(C)C)CC2)OC2(CC2)C1=O] | 12-ethyl-8-isobutyl-4-oxa-8,12-diazadispiro[2.1.5.3]tridecan-13-one | 3.31 (method A) | 281.2 |
| 7 | 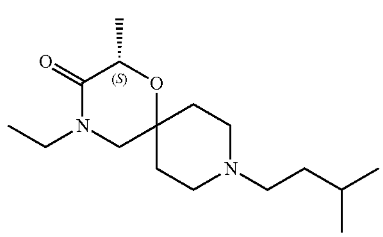 | (S)-4-ethyl-9-isopentyl-2-methyl-1-oxa-4,9-diazaspiro[5.5]undecan-3-one | 2.69 (method A) | 283.2 |
| 8 | 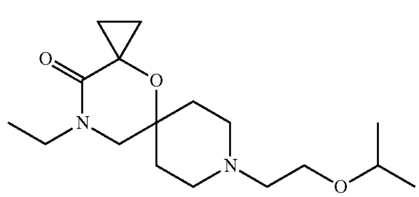 [SMILES: CCN1CC2(CCN(CCOC(C)C)CC2)OC2(CC2)C1=O] | 12-ethyl-8-(2-isopropoxyethyl)-4-oxa-8,12-diazadispiro[2.1.5.3]tridecan-13-one | 2.46 (method A) | 311.2 |

-continued

| EX | Structure | Chemical name | Ret time (min) | MS (M + H) |
|---|---|---|---|---|
| 9 | 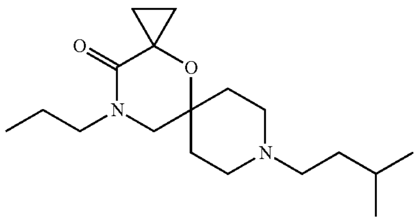 [SMILES: CCCN1CC2(CCN(CCC(C)C)CC2)OC2(CC2)C1=O] | 8-isopentyl-12-propyl-4-oxa-8,12-diazadispiro[2.1.5.3]tridecan-13-one | 3.66 (method A) | 309.2 |
| 10 | 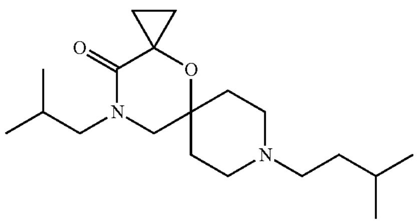 [SMILES: CC(C)CCN1CCC2(CC1)CN(CC(C)C)C(=O)C1(CC1)O2] | 12-isobutyl-8-isopentyl-4-oxa-8,12-diazadispiro[2.1.5.3]tridecan-13-one | 4.03 (method A) | 323.2 |
| 11 | 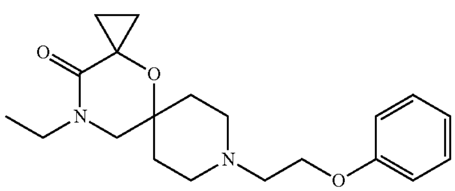 [SMILES: CCN1CC2(CCN(CCOc3ccccc3)CC2)OC2(CC2)C1=O] | 12-ethyl-8-(2-phenoxyethyl)-4-oxa-8,12-diazadispiro[2.1.5.3]tridecan-13-one | 3.86 (method C) | 345.2 |
| 12 | 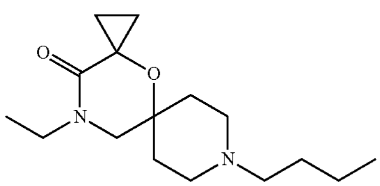 [SMILES: CCCCN1CCC2(CC1)CN(CC)C(=O)C1(CC1)O2] | 8-butyl-12-ethyl-4-oxa-8,12-diazadispiro[2.1.5.3]tridecan-13-one | 3.15 (method C) | 281.2 |
| 13 | 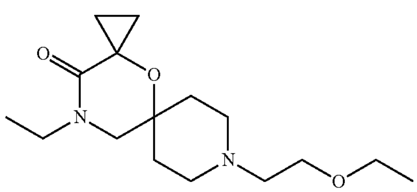 | 8-(2-ethoxyethyl)-12-ethyl-4-oxa-8,12-diazadispiro[2.1.5.3]tridecan-13-one | 2.85 (method C) | 297.2 |
| 14 | 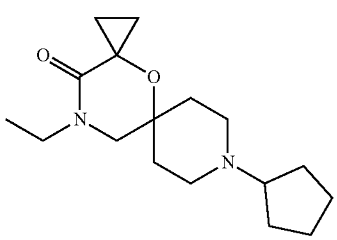 [SMILES: CCN1CC2(CCN(C3CCCC3)CC2)OC2(CC2)C1=O] | 8-cyclopentyl-12-ethyl-4-oxa-8,12-diazadispiro[2.1.5.3]tridecan-13-one | 3.13 (method C) | 293.2 |
| 15 | 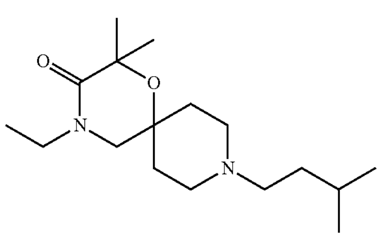 [SMILES: CCN1CC2(CCN(CCC(C)C)CC2)OC(C)(C)C1=O] | 4-ethyl-9-isopentyl-2,2-dimethyl-1-oxa-4,9-diazaspiro[5.5]undecan-3-one | 3.55 (method C) | 297.2 |

Example 16: 12-Ethyl-8-(4-fluorobenzyl)-4-oxa-8,12-diazadispiro[2.1.5.3]tridecan-13-one

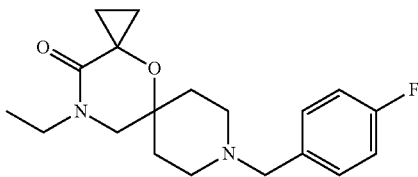 [SMILES: CCN1CC2(CCN(Cc3ccc(F)cc3)CC2)OC2(CC2)C1=O]

To a solution of the crude product obtained in step 1 of example 1 (0.173 g, 59 wt %, 0.30 mmol) in dry THF (2 mL), 4-fluorobenzaldehyde (0.042 mL, 0.39 mmol) was added. The reaction mixture was stirred at r.t. for 15 min, and then sodium triacetoxyborohydride (0.190 g, 0.91 mmol) was added in portions. The resulting mixture was stirred at r.t. overnight. Water and $NH_3$ conc were carefully added and it was extracted with ethyl acetate. The organic phases were combined, washed with brine, dried over $Na_2SO_4$, filtered and concentrated to dryness. The residue was purified by flash chromatography, silica gel, gradient DCM to MeOH:DCM (1:4) to give the title compound (55 mg, 55% yield).

HPLC retention time (method A): 3.08 min; MS: 333.1 (M+H).

This method was used for the preparation of examples 17-35 using suitable starting materials:

| EX | Structure | Chemical name | Ret time | MS (M + H) |
|---|---|---|---|---|
| 17 | 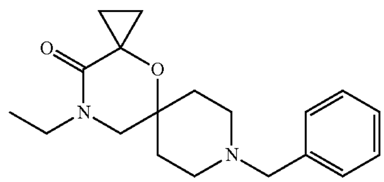 [SMILES: CCN1CC2(CCN(Cc3ccccc3)CC2)OC2(CC2)C1=O] | 8-benzyl-12-ethyl-4-oxa-8,12-diazadispiro[2.1.5.3]tridecan-13-one | 3.74 (method B) | 315.2 |
| 18 | 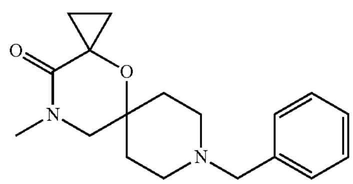 [SMILES: CN1CC2(CCN(Cc3ccccc3)CC2)OC2(CC2)C1=O] | 8-benzyl-12-methyl-4-oxa-8,12-diazadispiro[2.1.5.3]tridecan-13-one | 2.68 (method A) | 301.1 |
| 19 | 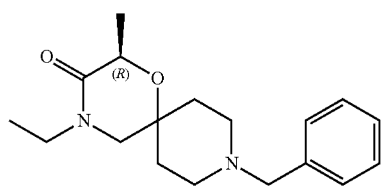 | (R)-9-benzyl-4-ethyl-2-methyl-1-oxa-4,9-diazaspiro[5.5]undecan-3-one | 2.48 (method A) | 303.2 |
| 20 | 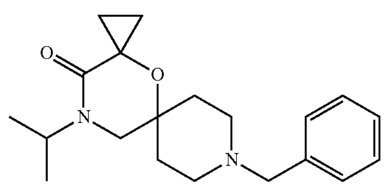 [SMILES: CC(C)N1CC2(CCN(Cc3ccccc3)CC2)OC2(CC2)C1=O] | 8-benzyl-12-isopropyl-4-oxa-8,12-diazadispiro[2.1.5.3]tridecan-13-one | 4.02 (method A) | 329.2 |
| 21 | 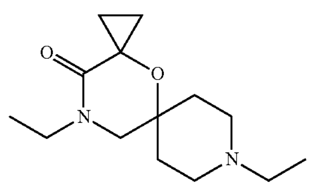 [SMILES: CCN1CCC2(CC1)CN(CC)C(=O)C1(CC1)O2] | 8,12-diethyl-4-oxa-8,12-diazadispiro[2.1.5.3]tridecan-13-one | 2.18 (method A) | 253.1 |
| 22 | 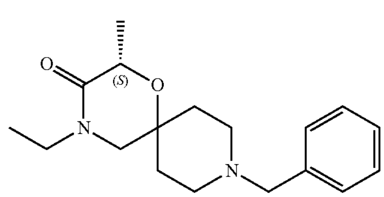 | (S)-9-benzyl-4-ethyl-2-methyl-1-oxa-4,9-diazaspiro[5.5]undecan-3-one | 2.93 (method A) | 303.2 |

| EX | Structure | Chemical name | Ret time | MS (M + H) |
|---|---|---|---|---|
| 23 | 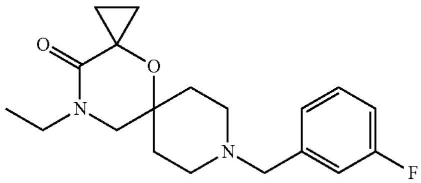 [SMILES: CCN1CC2(CCN(Cc3cccc(F)c3)CC2)OC2(CC2)C1=O] | 12-ethyl-8-(3-fluorobenzyl)-4-oxa-8,12-diazadispiro[2.1.5.3]tridecan-13-one | 3.00 (method A) | 333.1 |
| 24 | 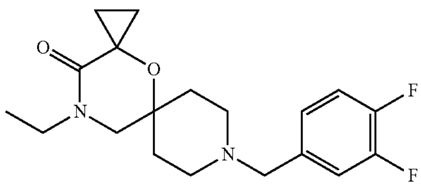 | 8-(3,4-difluorobenzyl)-12-ethyl-4-oxa-8,12-diazadispiro[2.1.5.3]tridecan-13-one | 3.16 (method A) | 351.2 |
| 25 | 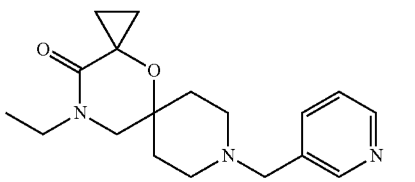 [SMILES: CCN1CC2(CCN(Cc3cccnc3)CC2)OC2(CC2)C1=O] | 12-ethyl-8-(pyridin-3-ylmethyl)-4-oxa-8,12-diazadispiro[2.1.5.3]tridecan-13-one | 2.32 (method A) | 316.2 |
| 26 | 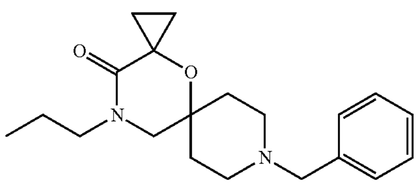 [SMILES: CCCN1CC2(CCN(Cc3ccccc3)CC2)OC2(CC2)C1=O] | 8-benzyl-12-propyl-4-oxa-8,12-diazadispiro[2.1.5.3]tridecan-13-one | 3.91 (method A) | 329.2 |
| 27 | 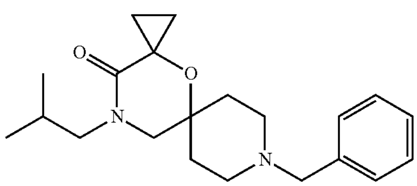 [SMILES: CC(C)CN1CC2(CCN(Cc3ccccc3)CC2)OC2(CC2)C1=O] | 8-benzyl-12-isobutyl-4-oxa-8,12-diazadispiro[2.1.5.3]tridecan-13-one | 3.55 (method A) | 343.2 |
| 28 | 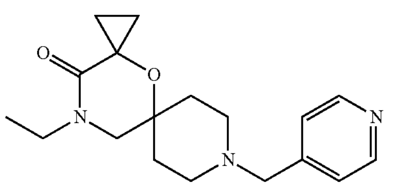 [SMILES: CCN1CC2(CCN(Cc3ccncc3)CC2)OC2(CC2)C1=O] | 12-ethyl-8-(pyridin-4-ylmethyl)-4-oxa-8,12-diazadispiro[2.1.5.3]tridecan-13-one | 2.91 (method C) | 316.1 |
| 29 | 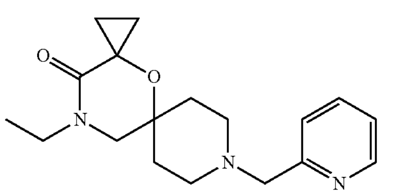 [SMILES: CCN1CC2(CCN(Cc3ccccn3)CC2)OC2(CC2)C1=O] | 12-ethyl-8-(pyridin-4-ylmethyl)-4-oxa-8,12-diazadispiro[2.1.5.3]tridecan-13-one | 2.89 (method C) | 316.2 |
| 30 | 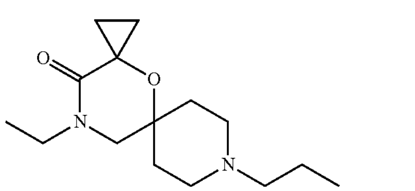 [SMILES: CCCN1CCC2(CC1)CN(CC)C(=O)C1(CC1)O2] | 12-ethyl-8-propyl-4-oxa-8,12-diazadispiro[2.1.5.3]tridecan-13-one | 2.84 (method C) | 267.1 |

| EX | Structure | Chemical name | Ret time | MS (M + H) |
|---|---|---|---|---|
| 31 | 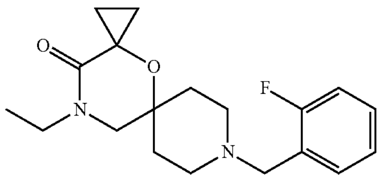 [SMILES: CCN1CC2(CCN(Cc3ccccc3F)CC2)OC2(CC2)C1=O] | 12-ethyl-8-(2-fluorobenzyl)-4-oxa-8,12-diazadispiro[2.1.5.3]tridecan-13-one | 3.98 (method C) | 333.2 |
| 32 | 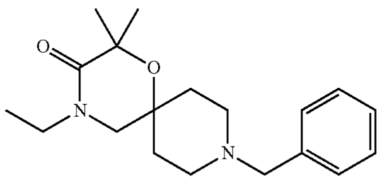 [SMILES: CCN1CC2(CCN(Cc3ccccc3)CC2)OC(C)(C)C1=O] | 9-benzyl-4-ethyl-2,2-dimethyl-1-oxa-4,9-diazaspiro[5.5]undecan-3-one | 3.93 (method C) | 317.2 |
| 33 | 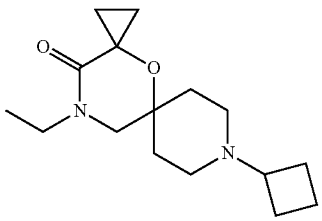 [SMILES: CCN1CC2(CCN(C3CCC3)CC2)OC2(CC2)C1=O] | 8-cyclobutyl-12-ethyl-4-oxa-8,12-diazadispiro[2.1.5.3]tridecan-13-one | 3.03 (method C) | 279.2 |
| 34 | 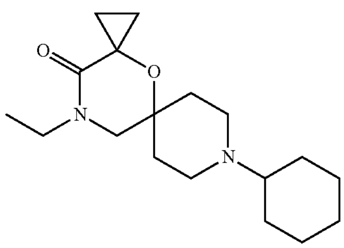 [SMILES: CCN1CC2(CCN(C3CCCCC3)CC2)OC2(CC2)C1=O] | 8-cyclohexyl-12-ethyl-4-oxa-8,12-diazadispiro[2.1.5.3]tridecan-13-one | 3.31 (method C) | 307.2 |
| 35 | 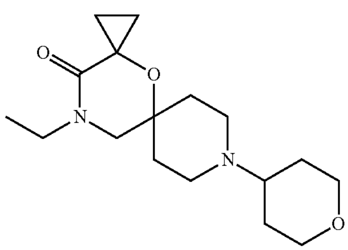 [SMILES: CCN1CC2(CCN(C3CCOCC3)CC2)OC2(CC2)C1=O] | 12-ethyl-8-(tetrahydro-2H-pyran-4-yl)-4-oxa-8,12-diazadispiro[2.1.5.3]tridecan-13-one | 2.55 (method C) | 309.2 |

Example 36: 8-(2-(3-Fluoropyridin-2-yl)ethyl)-12-isopropyl-4-oxa-8,12-diazadispiro[2.1.5.3]tridecane

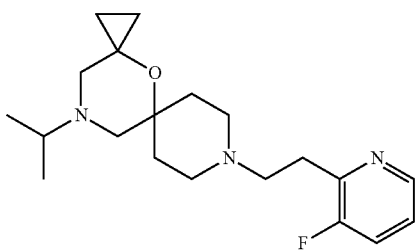 [SMILES: CC(C)N1CC2(CCN(CCc3ncccc3F)CC2)OC2(CC2)C1]

Step 1. 12-Isopropyl-4-oxa-8,12-diazadispiro[2.1.5.3]dihydrochloride. To a solution of intermediate 7A (156 mg, 0.48 mmol) in MeOH (2 mL), HCl (2M solution in diethyl ether, 2.4 mL, 4.8 mmol) was added, and the mixture was stirred at r.t. for 4 h. The solvent was evaporated under vacuum to give the corresponding di-HCl salt (143 mg, quantitative yield).

Step 2. Title compound: A solution of the crude product obtained in step 1 (0.125 g, 0.42 mmol), DIPEA (0.366 mL, 2.1 mmol) and 3-fluoro-2-vinylpyridine hydrochloride (0.115 g, 0.72 mmol) in EtOH (1.2 mL) was heated at 90° C. in a sealed tube for 1 day. Additional 3-fluoro-2-vinylpyridine hydrochloride (0.034 g, 0.210 mmol) was added and the mixture heated at 90° C. for another day. The reaction mixture was allowed to cool to r.t. and the solvent was evaporated. It was diluted with DCM and washed twice with 1N NaOH. The organic phase was dried over MgSO$_4$, filtered and concentrated to dryness. The residue was purified by flash chromatography, silica gel, gradient DCM to MeOH/DCM (1:4) to give the title compound (44 mg, 30% yield).

HPLC retention time (method A): 3.70 min; MS: 348.2 (M+H).

This method was used for the preparation of examples 37-43 using suitable starting materials:

| EX | Structure | Chemical name | Ret time | MS (M + H) |
|---|---|---|---|---|
| 37 | 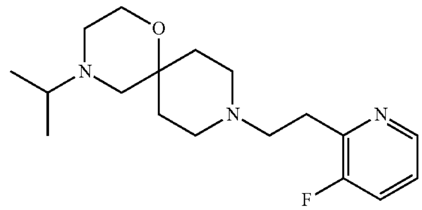 [SMILES: CC(C)N1CCOC2(CCN(CCc3ncccc3F)CC2)C1] | 9-(2-(3-fluoropyridin-2-yl)ethyl)-4-isopropyl-1-oxa-4,9-diazaspiro[5.5]undecane | 3.40 (method C) | 322.2 |
| 38 | 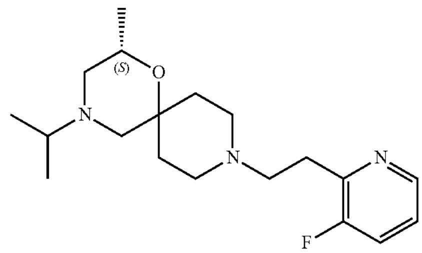 | (S)-9-(2-(3-fluoropyridin-2-yl)ethyl)-4-isopropyl-2-methyl-1-oxa-4,9-diazaspiro[5.5]undecane | 3.77 (method C) | 336.2 |
| 39 | 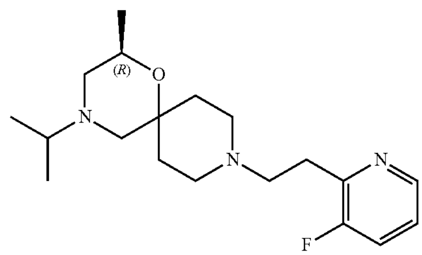 | (R)-9-(2-(3-fluoropyridin-2-yl)ethyl)-4-isopropyl-2-methyl-1-oxa-4,9-diazaspiro[5.5]undecane | 3.82 (method C) | 336.2 |
| 40 | 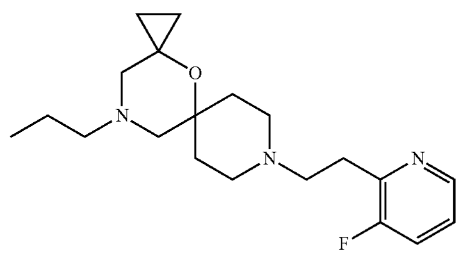 [SMILES: CCCN1CC2(CCN(CCc3ncccc3F)CC2)OC2(CC2)C1] | 8-(2-(3-fluoropyridin-2-yl)ethyl)-12-propyl-4-oxa-8,12-diazadispiro[2.1.5.3]tridecane | 3.94 (method C) | 348.2 |
| 41 | 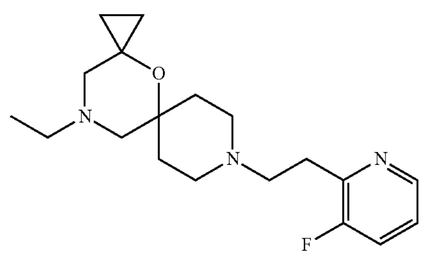 | 12-ethyl-8-(2-(3-fluoropyridin-2-yl)ethyl)-4-oxa-8,12-diazadispiro[2.1.5.3]tridecane | 3.45 (method C) | 334.2 |
| 42 | 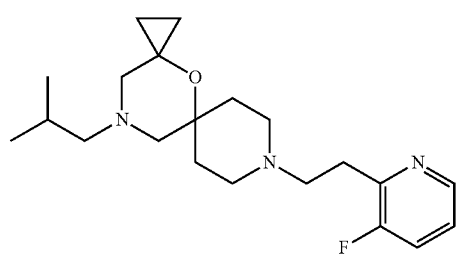 [SMILES: CC(C)CN1CC2(CCN(CCc3ncccc3F)CC2)OC2(CC2)C1] | 8-(2-(3-fluoropyridin-2-yl)ethyl)-12-isobutyl-4-oxa-8,12-diazadispiro[2.1.5.3]tridecane | 5.00 (method C) | 362.2 |

-continued

| EX | Structure | Chemical name | Ret time | MS (M + H) |
|---|---|---|---|---|
| 43 | 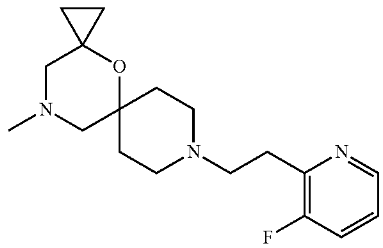 [SMILES: CN1CC2(CCN(CCc3ncccc3F)CC2)OC2(CC2)C1] | 8-(2-(3-fluoropyridin-2-yl)ethyl)-12-methyl-4-oxa-8,12-diazadispiro[2.1.5.3]tridecane | 3.01 (method C) | 320.2 |

The method described in Example 1 was used for the preparation of examples 44-65 using suitable starting materials:

| EX | Structure | Chemical name | Ret time (min) | MS (M + H) |
|---|---|---|---|---|
| 44 | 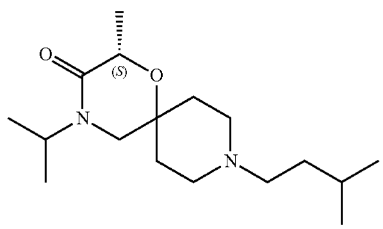 | (S)-9-isopentyl-4-isopropyl-2-methyl-1-oxa-4,9-diazaspiro[5.5]undecan-3-one | 3.61 (method C) | 297.2 |
| 45 | 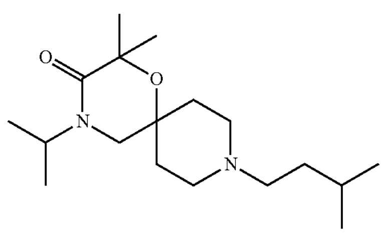 [SMILES: CC(C)CCN1CCC2(CC1)CN(C(C)C)C(=O)C(C)(C)O2] | 9-isopentyl-4-isopropyl-2,2-dimethyl-1-oxa-4,9-diazaspiro[5.5]undecan-3-one | 3.92 (method C) | 311.2 |
| 46 | 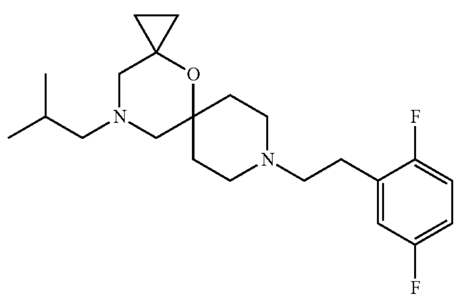 [SMILES: CC(C)CN1CC2(CCN(CCc3cc(F)ccc3F)CC2)OC2(CC2)C1] | 8-(2,5-difluorophenethyl)-12-isobutyl-4-oxa-8,12-diazadispiro[2.1.5.3]tridecane | 6.16 (method C) | 379.2 |
| 47 | 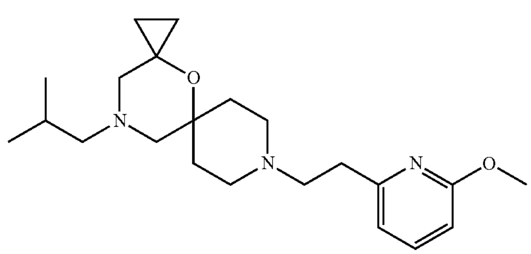 [SMILES: COc1cccc(CCN2CCC3(CC2)CN(CC(C)C)CC2(CC2)O3)n1] | 12-isobutyl-8-(2-(6-methoxypyridin-2-yl)ethyl)-4-oxa-8,12-diazadispiro[2.1.5.3]tridecane | 5.43 (method C) | 374.2 |

| EX | Structure | Chemical name | Ret time (min) | MS (M + H) |
|---|---|---|---|---|
| 48 | 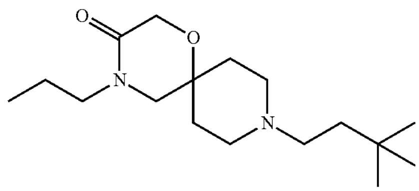 [SMILES: CCCN1CC2(CCN(CCC(C)(C)C)CC2)OCC1=O] | 9-(3,3-dimethylbutyl)-4-propyl-1-oxa-4,9-diazaspiro[5.5]undecan-3-one | 3.57 (method C) | 297.2 |
| 49 | 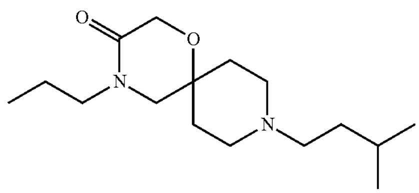 [SMILES: CCCN1CC2(CCN(CCC(C)C)CC2)OCC1=O] | 9-isopentyl-4-propyl-1-oxa-4,9-diazaspiro[5.5]undecan-3-one | 3.32 (method C) | 283.2 |
| 50 | 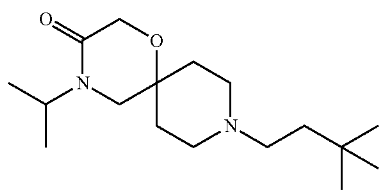 [SMILES: CC(C)N1CC2(CCN(CCC(C)(C)C)CC2)OCC1=O] | 9-(3,3-dimethylbutyl)-4-isopropyl-1-oxa-4,9-diazaspiro[5.5]undecan-3-one | 3.58 (method C) | 297.2 |
| 51 | 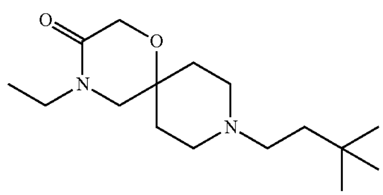 [SMILES: CCN1CC2(CCN(CCC(C)(C)C)CC2)OCC1=O] | 9-(3,3-dimethylbutyl)-4-ethyl-1-oxa-4,9-diazaspiro[5.5]undecan-3-one | 3.32 (method C) | 283.2 |
| 52 | 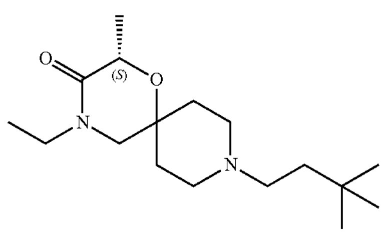 | (S)-9-(3,3-dimethylbutyl)-4-ethyl-2-methyl-1-oxa-4,9-diazaspiro[5.5]undecan-3-one | 3.62 (method C) | 297.2 |
| 53 | 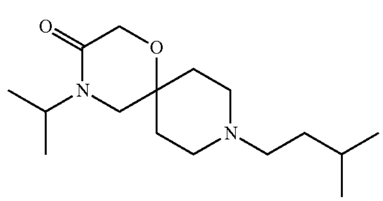 [SMILES: CC(C)CCN1CCC2(CC1)CN(C(C)C)C(=O)CO2] | 9-isopentyl-4-isopropyl-1-oxa-4,9-diazaspiro[5.5]undecan-3-one | 3.33 (method C) | 283.2 |
| 54 | 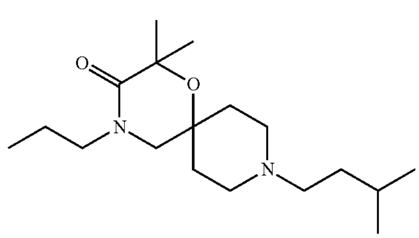 [SMILES: CCCN1CC2(CCN(CCC(C)C)CC2)OC(C)(C)C1=O] | 9-isopentyl-2,2-dimethyl-4-propyl-1-oxa-4,9-diazaspiro[5.5]undecan-3-one | 3.95 (method C) | 311.1 |

| EX | Structure | Chemical name | Ret time (min) | MS (M + H) |
|---|---|---|---|---|
| 55 | 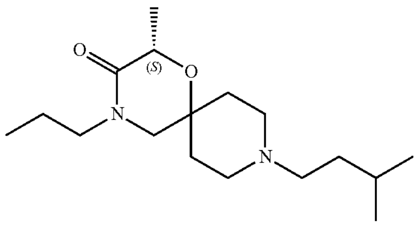 | (S)-9-isopentyl-2-methyl-4-propyl-1-oxa-4,9-diazaspiro[5.5]undecan-3-one | 4.21 (method D) | 297.1 |
| 56 | 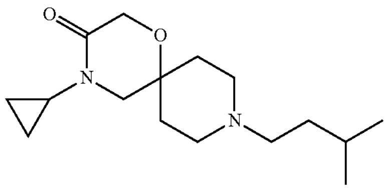 [SMILES: CC(C)CCN1CCC2(CC1)CN(C1CC1)C(=O)CO2] | 4-cyclopropyl-9-isopentyl-1-oxa-4,9-diazaspiro[5.5]undecan-3-one | 3.59 (method D) | 281.1 |
| 57 | 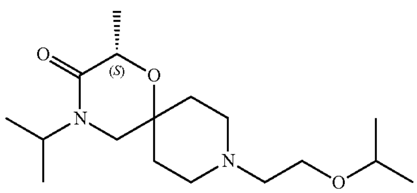 | (S)-9-(2-isopropoxyethyl)-4-isopropyl-2-methyl-1-oxa-4,9-diazaspiro[5.5]undecan-3-one | 3.57 (method D) | 313.2 |
| 58 | 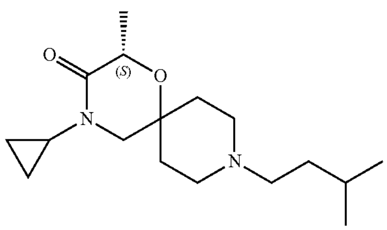 | (S)-4-cyclopropyl-9-isopentyl-2-methyl-1-oxa-4,9-diazaspiro[5.5]undecan-3-one | 3.83 (method D) | 295.2 |
| 59 | 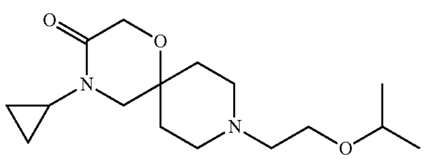 [SMILES: CC(C)OCCN1CCC2(CC1)CN(C1CC1)C(=O)CO2] | 4-cyclopropyl-9-(2-isopropoxyethyl)-1-oxa-4,9-diazaspiro[5.5]undecan-3-one | 3.10 (method D) | 297.2 |
| 60 | 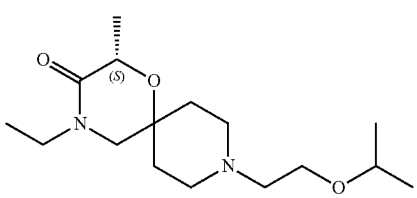 | (S)-4-ethyl-9-(2-isopropoxyethyl)-2-methyl-1-oxa-4,9-diazaspiro[5.5]undecan-3-one | 3.32 (method D) | 299.1 |
| 61 | 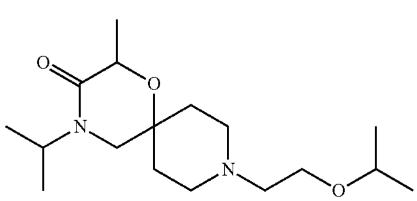 [SMILES: CC(C)OCCN1CCC2(CC1)CN(C(C)C)C(=O)C(C)O2] | 9-(2-isopropoxyethyl)-4-isopropyl-2-methyl-1-oxa-4,9-diazaspiro[5.5]undecan-3-one | 2.94 (method B) | 313.2 |

-continued

| EX | Structure | Chemical name | Ret time (min) | MS (M + H) |
|---|---|---|---|---|
| 62 | 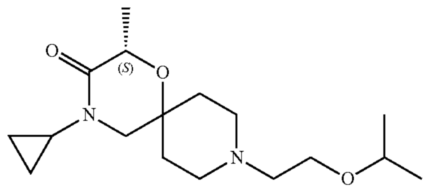 | (S)-4-cyclopropyl-9-(2-isopropoxyethyl)-2-methyl-1-oxa-4,9-diazaspiro[5.5]undecan-3-one | 3.39 (method D) | 311.2 |
| 63 | 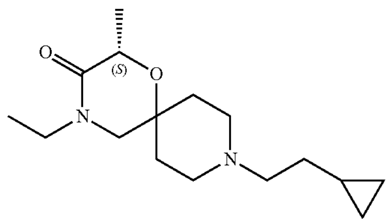 | (S)-9-(2-cyclopropylethyl)-4-ethyl-2-methyl-1-oxa-4,9-diazaspiro[5.5]undecan-3-one | 3.65 (method D) | 281.2 |
| 64 | 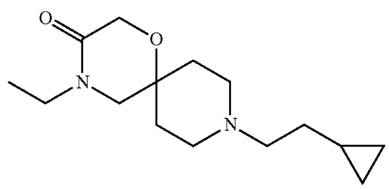 [SMILES: CCN1CC2(CCN(CCC3CC3)CC2)OCC1=O] | 9-(2-cyclopropylethyl)-4-ethyl-1-oxa-4,9-diazaspiro[5.5]undecan-3-one | 3.34 (method D) | 267.2 |
| 65 | 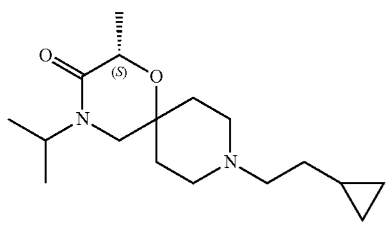 | (S)-9-(2-cyclopropylethyl)-4-isopropyl-2-methyl-1-oxa-4,9-diazaspiro[5.5]undecan-3-one | 3.93 (method D) | 295.2 |
| 66 | 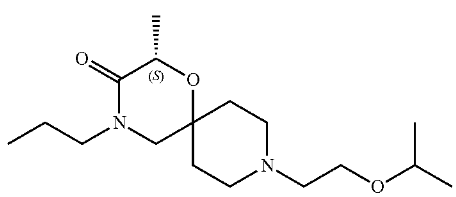 | (S)-9-(2-isopropoxyethyl)-2-methyl-4-propyl-1-oxa-4,9-diazaspiro[5.5]undecan-3-one | 3.66 (method D) | 313.2 |

The method described in Example 16 was used for the preparation of examples 67-100 using suitable starting materials:

| EX | Structure | Chemical name | Ret time (min) | MS (M + H) |
|---|---|---|---|---|
| 67 | 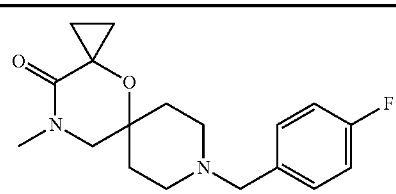 | 8-(4-fluorobenzyl)-12-methyl-4-oxa-8,12-diazadispiro[2.1.5.3]tridecan-13-one | 3.7 (method C) | 319.2 |

-continued

| EX | Structure | Chemical name | Ret time (min) | MS (M + H) |
|---|---|---|---|---|
| 68 | 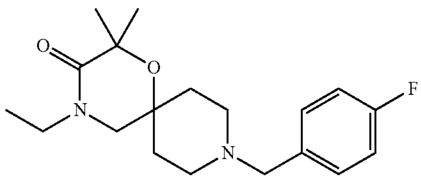 [SMILES: CCN1CC2(CCN(Cc3ccc(F)cc3)CC2)OC(C)(C)C1=O] | 4-ethyl-9-(4-fluorobenzyl)-2,2-dimethyl-1-oxa-4,9-diazaspiro[5.5]undecan-3-one | 4.09 (method C) | 335.2 |
| 69 | 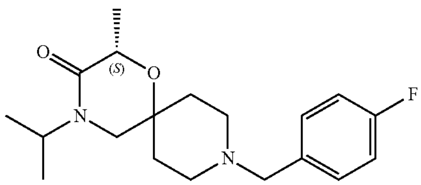 | (S)-9-(4-fluorobenzyl)-4-isopropyl-2-methyl-1-oxa-4,9-diazaspiro[5.5]undecan-3-one | 4.06 (method C) | 335.2 |
| 70 | 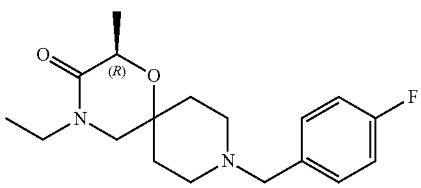 | (R)-4-ethyl-9-(4-fluorobenzyl)-2-methyl-1-oxa-4,9-diazaspiro[5.5]undecan-3-one | 3.78 (method C) | 321.2 |
| 71 | 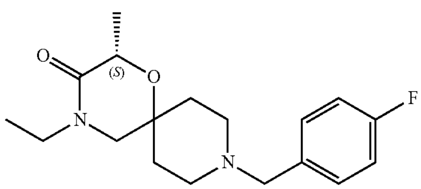 | (S)-4-ethyl-9-(4-fluorobenzyl)-2-methyl-1-oxa-4,9-diazaspiro[5.5]undecan-3-one | 3.78 (method C) | 321.2 |
| 72 | 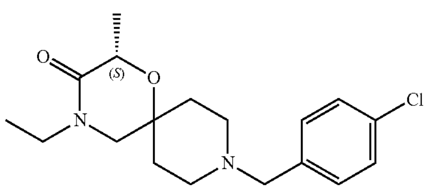 | (S)-9-(4-chlorobenzyl)-4-ethyl-2-methyl-1-oxa-4,9-diazaspiro[5.5]undecan-3-one | 4.13 (method C) | 337.1 |
| 73 | 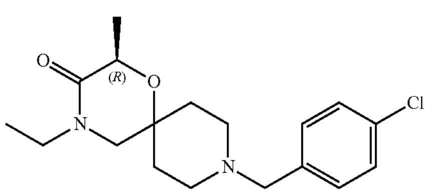 | (R)-9-(4-chlorobenzyl)-4-ethyl-2-methyl-1-oxa-4,9-diazaspiro[5.5]undecan-3-one | 4.13 (method C) | 337.1 |
| 74 | 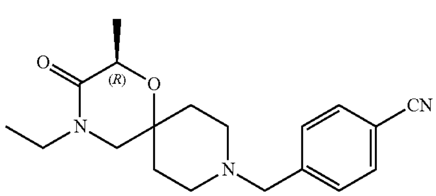 | (R)-4-((4-ethyl-2-methyl-3-oxo-1-oxa-4,9-diazaspiro[5.5]undecan-9-yl)methyl)benzonitrile | 3.54 (method C) | 328.2 |
| 75 | 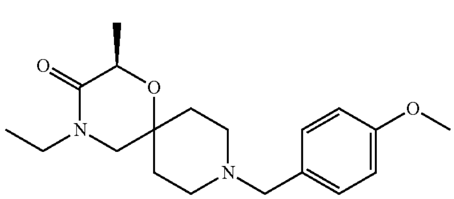 [SMILES: CCN1CC2(CCN(Cc3ccc(OC)cc3)CC2)O[C@H](C)C1=O] | (R)-4-ethyl-9-(4-methoxybenzyl)-2-methyl-1-oxa-4,9-diazaspiro[5.5]undecan-3-one | 3.51 (method C) | 333.2 |

-continued

| EX | Structure | Chemical name | Ret time (min) | MS (M + H) |
|---|---|---|---|---|
| 76 | 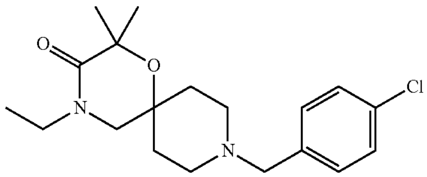 [SMILES: CCN1CC2(CCN(Cc3ccc(Cl)cc3)CC2)OC(C)(C)C1=O] | 9-(4-chlorobenzyl)-4-ethyl-2,2-dimethyl-1-oxa-4,9-diazaspiro[5.5]undecan-3-one | 4.45 (method C) | 351.1 |
| 77 | 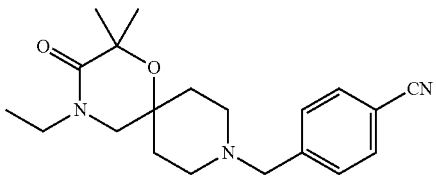 [SMILES: CCN1CC2(CCN(Cc3ccc(C#N)cc3)CC2)OC(C)(C)C1=O] | 4-((4-ethyl-2,2-dimethyl-3-oxo-1-oxa-4,9-diazaspiro[5.5]undecan-9-yl)methyl)benzonitrile | 3.83 (method C) | 342.2 |
| 78 | 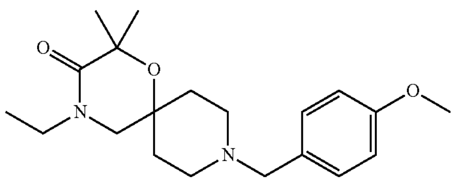 [SMILES: CCN1CC2(CCN(Cc3ccc(OC)cc3)CC2)OC(C)(C)C1=O] | 4-ethyl-9-(4-methoxybenzyl)-2,2-dimethyl-1-oxa-4,9-diazaspiro[5.5]undecan-3-one | 3.81 (method C) | 347.2 |
| 79 | 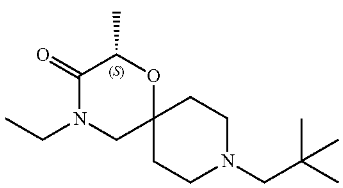 | (S)-4-ethyl-2-methyl-9-neopentyl-1-oxa-4,9-diazaspiro[5.5]undecan-3-one | 4.29 (method C) | 283.2 |
| 80 | 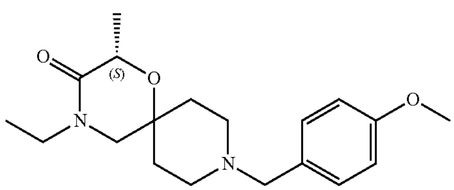 | (S)-4-ethyl-9-(4-methoxybenzyl)-2-methyl-1-oxa-4,9-diazaspiro[5.5]undecan-3-one | 3.55 (method C) | 333.2 |
| 81 | 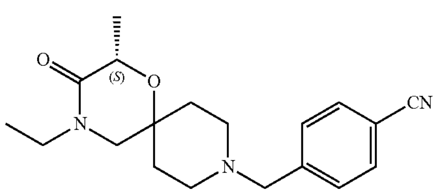 | (S)-4-((4-ethyl-2-methyl-3-oxo-1-oxa-4,9-diazaspiro[5.5]undecan-9-yl)methyl)benzonitrile | 3.53 (method C) | 328.2 |
| 82 | 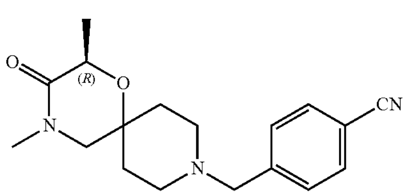 | (R)-4-((2,4-dimethyl-3-oxo-1-oxa-4,9-diazaspiro[5.5]undecan-9-yl)methyl)benzonitrile | 3.67 (method D) | 314.1 |
| 83 | 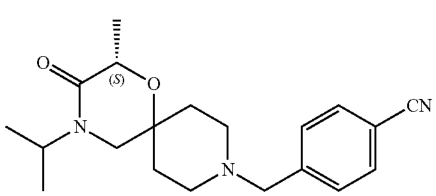 | (S)-4-((4-isopropyl-2-methyl-3-oxo-1-oxa-4,9-diazaspiro[5.5]undecan-9-yl)methyl)benzonitrile | 4.24 (method D) | 342.2 |

-continued

| EX | Structure | Chemical name | Ret time (min) | MS (M + H) |
|---|---|---|---|---|
| 84 | 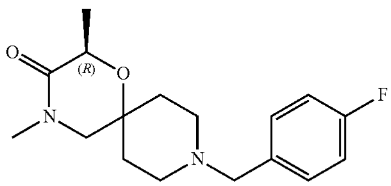 | (R)-9-(4-fluorobenzyl-2,4-dimethyl-1-oxa-4,9-diazaspiro[5.5]undecan-3-one | 3.87 (method D) | 307.1 |
| 85 | 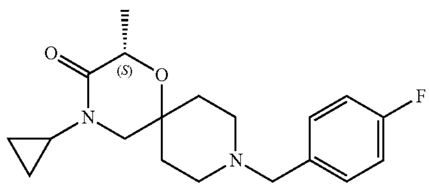 | (S)-4-cyclopropyl-9-(4-fluorobenzyl)-2-methyl-1-oxa-4,9-diazaspiro[5.5]undecan-3-one | 4.25 (method D) | 333.1 |
| 86 | 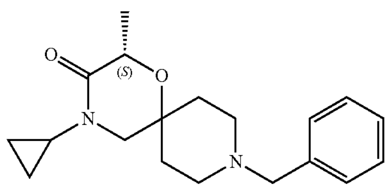 | (S)-9-benzyl-4-cyclopropyl-2-methyl-1-oxa-4,9-diazaspiro[5.5]undecan-3-one | 4.11 (method D) | 315.1 |
| 87 | 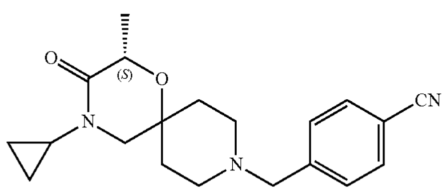 | (S)-4-((4-cyclopropyl-2-methyl-3-oxo-1-oxa-4,9-diazaspiro[5.5]undecan-9-yl)methyl)benzonitrile | 4.02 (method D) | 340.1 |
| 88 | 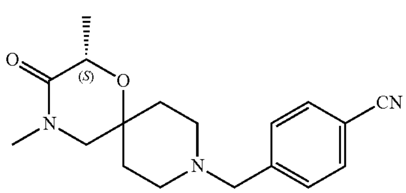 | (S)-4-((2,4-dimethyl-3-oxo-1-oxa-4,9-diazaspiro[5.5]undecan-9-yl)methyl)benzonitrile | 3.64 (method D) | 314.1 |
| 89 | 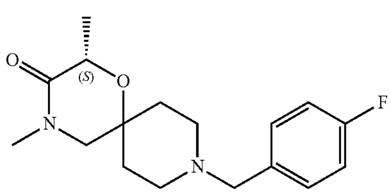 | (S)-9-(4-fluorobenzyl)-2,4-dimethyl-1-oxa-4,9-diazaspiro[5.5]undecan-3-one | 3.85 (method D) | 307.1 |
| 90 | 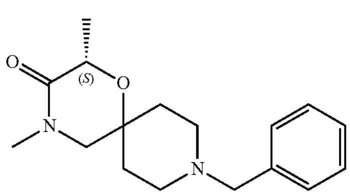 | (S)-9-benzyl-2,4-dimethyl-1-oxa-4,9-diazaspiro[5.5]undecan-3-one | 3.73 (method D) | 289.1 |
| 91 | 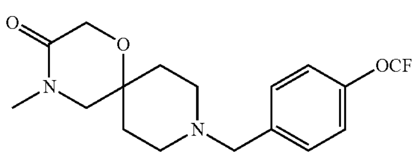 | (S)-2,4-dimethyl-9-(4-(trifluoromethoxy)benzyl)-1-oxa-4,9-diazaspiro[5.5]undecan-3-one | 4.68 (method D) | 373.1 |

-continued

| EX | Structure | Chemical name | Ret time (min) | MS (M + H) |
|---|---|---|---|---|
| 92 | 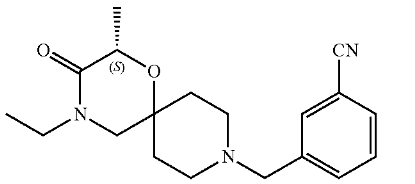 | (S)-3-((4-ethyl-2-methyl-3-oxo-1-oxa-4,9-diazaspiro[5.5]undecan-9-yl)methyl)benzonitrile | 3.97 (method D) | 328.2 |
| 93 | 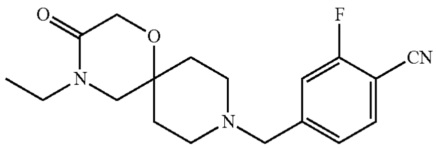 [SMILES: CCN1CC2(CCN(Cc3ccc(C#N)c(F)c3)CC2)OCC1=O] | (S)-4-((4-ethyl-2-methyl-3-oxo-1-oxa-4,9-diazaspiro[5.5]undecan-9-yl)methyl)-2-fluorobenzonitrile | 4.22 (method D) | 346.1 |
| 94 | 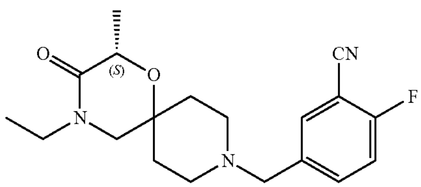 | (S)-5-((4-ethyl-2-methyl-3-oxo-1-oxa-4,9-diazaspiro[5.5]undecan-9-yl)methyl)-2-fluorobenzonitrile | 4.14 (method D) | 346.1 |
| 95 | 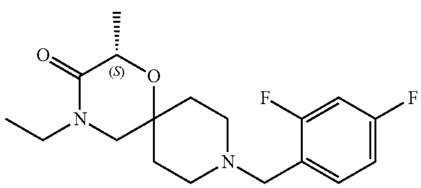 | (S)-9-(2,4-difluorobenzyl)-4-ethyl-2-methyl-1-oxa-4,9-diazaspiro[5.5]undecan-3-one | 4.30 (method D) | 339.1 |
| 96 | 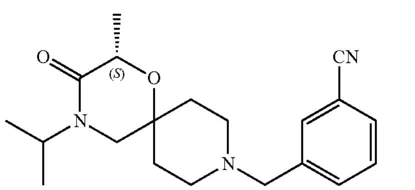 | (S)-3-((4-isopropyl-2-methyl-3-oxo-1-oxa-4,9-diazaspiro[5.5]undecan-9-yl)methyl)benzonitrile | 4.25 (method D) | 342.1 |
| 97 | 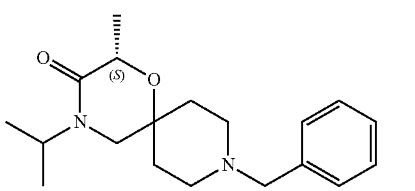 | (S)-9-benzyl-4-isopropyl-2-methyl-1-oxa-4,9-diazaspiro[5.5]undecan-3-one | 4.35 (method D) | 317.2 |
| 98 | 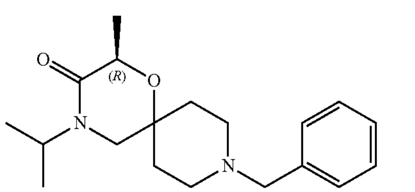 | (R)-9-benzyl-4-isopropyl-2-methyl-1-oxa-4,9-diazaspiro[5.5]undecan-3-one | 4.36 (method D) | 317.1 |
| 99 | 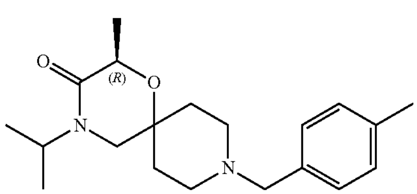 | (R)-9-(4-fluorobenzyl)-4-isopropyl-2-methyl-1-oxa-4,9-diazaspiro[5.5]undecan-3-one | 4.49 (method D) | 335.1 |

-continued

| EX | Structure | Chemical name | Ret time (min) | MS (M + H) |
|---|---|---|---|---|
| 100 | 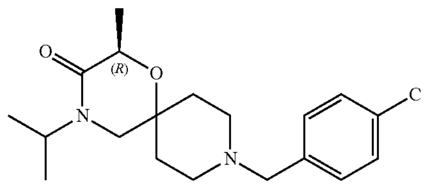 | (R)-4-((4-isopropyl-2-methyl-3-oxo-1-oxa-4,9-diazaspiro[5.5]undecan-9-yl)methyl)benzonitrile | 4.24 (method D) | 342.2 |

The method described in Example 36 was used for the preparation of examples 101-108 using suitable starting materials:

| EX | Structure | Chemical name | Ret time (min) | MS (M + H) |
|---|---|---|---|---|
| 101 | 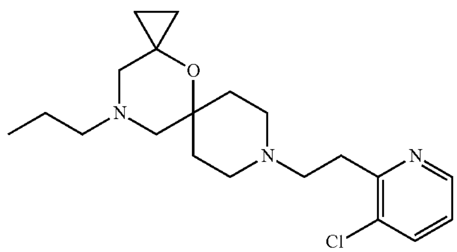 [SMILES: CCCN1CC2(CCN(CCc3ncccc3Cl)CC2)OC2(CC2)C1] | 8-(2-(3-chloropyridin-2-yl)ethyl)-12-isobutyl-4-oxa-8,12-diazadispiro[2.1.5.3]tridecane | 5.62 (method C) | 378.2 |
| 102 | 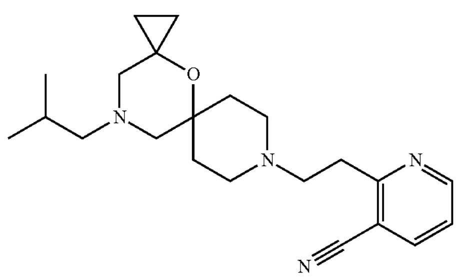 [SMILES: CC(C)CN1CC2(CCN(CCc3ncccc3C#N)CC2)OC2(CC2)C1] | 2-(2-(12-isobutyl-4-oxa-8,12-diazadispiro[2.1.5.3]tridecan-8-yl)ethyl)nicotinonitrile | 4.86 (method C) | 369.2 |
| 103 | 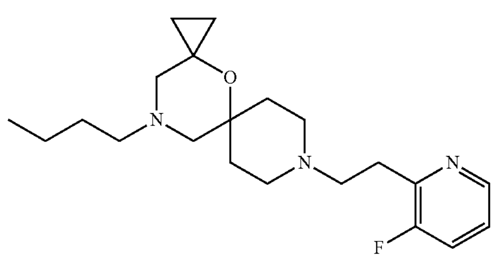 [SMILES: CCCCN1CC2(CCN(CCc3ncccc3F)CC2)OC2(CC2)C1] | 8-(2-(3-fluoropyridin-2-yl)ethyl)-12-isopentyl-4-oxa-8,12-diazadispiro[2.1.5.3]tridecane | 4.71 (method C) | 376.3 |
| 104 | 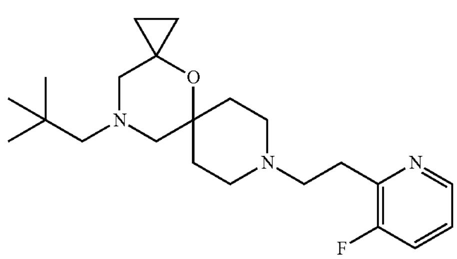 [SMILES: CC(C)(C)CN1CC2(CCN(CCc3ncccc3F)CC2)OC2(CC2)C1] | 8-(2-(3-fluoropyridin-2-yl)ethyl)-12-neopentyl-4-oxa-8,12-diazadispiro[2.1.5.3]tridecane | 5.48 (method C) | 376.3 |

-continued

| EX | Structure | Chemical name | Ret time (min) | MS (M + H) |
|---|---|---|---|---|
| 105 | 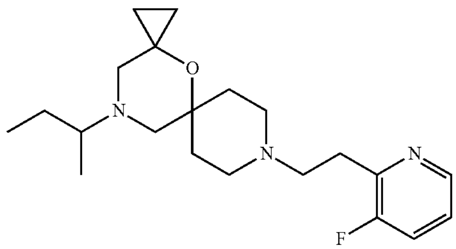 [SMILES: CCC(C)N1CC2(CCN(CCc3ncccc3F)CC2)OC2(CC2)C1] | 12-(sec-butyl)-8-(2-(3-fluoropyridin-2-yl)ethyl)-4-oxa-8,12-diazadispiro[2.1.5.3]tridecane | 4.53 (method C) | 362.2 |
| 106 | 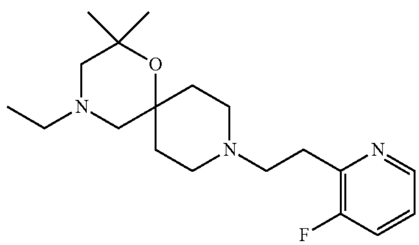 [SMILES: CCN1CC(C)(C)OC2(CCN(CCc3ncccc3F)CC2)C1] | 4-ethyl-9-(2-(3-fluoropyridin-2-yl)ethyl)-2,2-dimethyl-1-oxa-4,9-diazaspiro[5.5]undecane | 4.19 (method C) | 336.2 |
| 107 | 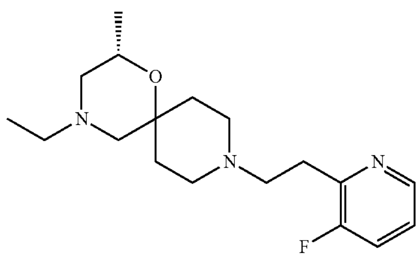 [SMILES: CCN1C[C@H](C)OC2(CCN(CCc3ncccc3F)CC2)C1] | (S)-4-ethyl-9-(2-(3-fluoropyridin-2-yl)ethyl)-2-methyl-1-oxa-4,9-diazaspiro[5.5]undecane | 3.42 (method C) | 322.2 |
| 108 | 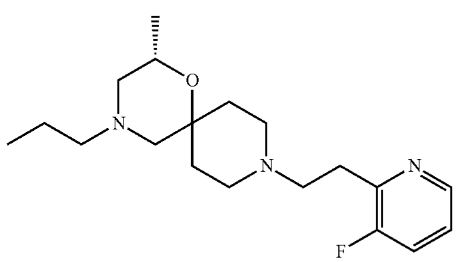 [SMILES: CCCN1C[C@H](C)OC2(CCN(CCc3ncccc3F)CC2)C1] | (S)-9-(2-(3-fluoropyridin-2-yl)ethyl)-2-methyl-4-propyl-1-oxa-4,9-diazaspiro[5.5]undecane | 4.49 (method D) | 336.1 |

Example 109: 4-Isopropyl-2-methyl-9-phenethyl-1-oxa-4,9-diazaspiro[5.5]undecane

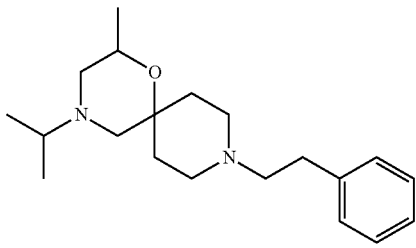

Step 1. 4-Isopropyl-2-methyl-9-phenethyl-1-oxa-4,9-diazaspiro[5.5]undecan-3-one. To a solution of intermediate 6L (0.168 g, 0.58 mmol) in dry DMF (5 mL), NaH (47 mg, 60 wt % in mineral oil, 1.17 mmol) was added. The reaction mixture was stirred at r.t. for 30 min, then 2-bromopropane (0.054 mL, 0.58 mmol) was added and the resulting mixture was stirred at r.t. overnight. Water was added and it was extracted with ethyl acetate. The organic phases were combined, washed with brine, dried over MgSO$_4$, filtered and concentrated to dryness. The residue was purified by flash chromatography, silica gel, gradient DCM to MeOH/DCM (1:4) to give the title compound (84 mg, 43% yield).

Step 2. Title compound: To a solution of the product obtained in step 1 (50 mg, 0.15 mmol) in dry THF (1 mL), cooled at 0° C., lithium aluminium hydride solution (0.6 mL. 1M in THF, 0.6 mmol) was added dropwise. The reaction mixture was stirred at 50° C. for 3 h and then at r.t. overnight. 1M NaOH was added and the heterogeneous mixture was filtered through a pad of celite, washing with THF. The filtrate was concentrated to dryness and the residue was purified by flash chromatography, silica gel, gradient DCM to MeOH:DCM (1:4) to give the title compound (36 mg, 76% yield).

HPLC retention time (method B): 4.45 min; MS: 317.2 (M+H).

This method was used for the preparation of examples 110-111 using suitable starting materials:

| EX | Structure | Chemical name | Ret time (min) | MS (M + H) |
|---|---|---|---|---|
| 110 | 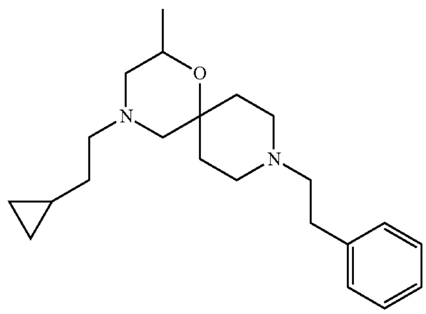 [SMILES: CC1CN(CCC2CC2)CC2(CCN(CCc3ccccc3)CC2)O1] | 4-(2-cyclopropylethyl)-2-methyl-9-phenethyl-1-oxa-4,9-diazaspiro[5.5]undecane | 5.05 (method B) | 343.2 |
| 111 | 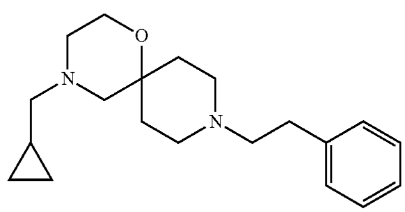 [SMILES: c1ccc(CCN2CCC3(CC2)CN(CC2CC2)CCO3)cc1] | 4-(cyclopropylmethyl)-9-phenethyl-1-oxa-4,9-diazaspiro[5.5]undecane | 4.06 (method B) | 315.2 |

Example 112: 4-Ethyl-2-methyl-9-phenethyl-1-oxa-4,9-diazaspiro[5.5]undecane

Step 1. 4-Ethyl-2-methyl-9-phenethyl-1-oxa-4,9-diazaspiro[5.5]undecan-3-one. Following the method described for the preparation of Example 1 but starting from intermediate 5F (220 mg, 0.70 mmol), the title compound was obtained (162 mg, 73% yield).

Step 2. Title compound: To a solution of the product obtained in step 1 (101 mg, 0.32 mmol) in dry THF (2 mL), cooled at 0° C., lithium aluminium hydride solution (1.28 mL, 1M in THF, 1.28 mmol) was added dropwise. The reaction mixture was stirred at 50° C. overnight. 1M NaOH was added and the heterogeneous mixture was filtered through a pad of celite, washing with THF. The filtrate was concentrated to dryness and the residue was purified by flash chromatography, silica gel, gradient DCM to MeOH:DCM (1:4) to give the title compound (55 mg, 57% yield).

HPLC retention time (method B): 3.91 min; MS: 303.2 (M+H).

This method was used for the preparation of example 113 using suitable starting materials:

| EX | Structure | Chemical name | Ret time (min) | MS (M + H) |
|---|---|---|---|---|
| 113 | 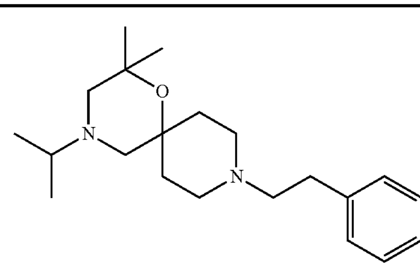 | 4-isopropyl-2,2-dimethyl-9-phenethyl-1-oxa-4,9-diazaspiro[5.5]undecane | 5.45 (method B) | 331.1 |

Table of Examples with Binding to the $\sigma_1$-Receptor:

BIOLOGICAL ACTIVITY

Pharmacological Study

Human $\sigma_1$ Receptor Radioligand Assay

To investigate binding properties of test compounds to human $\sigma_1$ receptor, transfected HEK-293 membranes and [$^3$H](+)-pentazocine (Perkin Elmer, NET-1056), as the radioligand, were used. The assay was carried out with 7 μg of membrane suspension, 5 nM of [$^3$H](+)-pentazocine in either absence or presence of either buffer or 10 μM Haloperidol for total and non-specific binding, respectively. Binding buffer contained Tris-HCl 50 mM at pH 8. Plates were incubated at 37° C. for 120 minutes. After the incubation period, the reaction mix was then transferred to Multiscreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail Results:

As this invention is aimed at providing a compound or a chemically related series of compounds which act as ligands of the $\sigma_1$ receptor it is a very preferred embodiment in which the compounds are selected which act as ligands of the $\sigma_1$ receptor and especially compounds which have a binding expressed as $K_i$ which is preferably <1000 nM, more preferably <500 nM, even more preferably <100 nM.

The following scale as been adopted for representing the binding to the $\sigma_1$ receptor expressed as $K_i$:

+ $K_i$-$\sigma_1$>=500 nM
++ $K_i$-$\sigma_1$<500 nM
+++ $K_i$-$\sigma_1$<100 nM All compounds prepared in the present application exhibit binding to the $\sigma_1$ receptor, in particular the following binding results are shown:

| EXAMPLE | $K_i$-$\sigma_1$ |
|---|---|
| 1 | +++ |
| 2 | +++ |
| 3 | ++ |
| 4 | ++ |
| 5 | +++ |
| 6 | ++ |
| 7 | +++ |
| 8 | ++ |
| 9 | +++ |
| 10 | +++ |
| 11 | + |
| 12 | ++ |
| 13 | + |
| 14 | ++ |
| 15 | +++ |
| 16 | +++ |
| 17 | +++ |
| 18 | +++ |
| 19 | +++ |
| 20 | +++ |
| 21 | + |
| 22 | +++ |
| 23 | +++ |
| 24 | +++ |
| 25 | ++ |
| 26 | +++ |
| 27 | +++ |
| 28 | ++ |
| 29 | + |
| 30 | + |
| 31 | ++ |
| 32 | +++ |
| 33 | + |
| 34 | ++ |
| 35 | + |
| 36 | +++ |
| 37 | ++ |
| 38 | +++ |
| 39 | ++ |
| 40 | +++ |
| 41 | ++ |
| 42 | +++ |
| 43 | + |
| 44 | ++ |
| 45 | +++ |
| 46 | +++ |
| 47 | +++ |
| 48 | +++ |
| 49 | +++ |
| 50 | ++ |
| 51 | ++ |
| 52 | ++ |
| 53 | ++ |
| 54 | +++ |
| 55 | +++ |
| 56 | ++ |
| 57 | ++ |
| 58 | ++ |
| 59 | ++ |
| 60 | ++ |
| 61 | ++ |
| 62 | + |
| 63 | + |
| 64 | + |
| 65 | + |
| 66 | + |
| 67 | +++ |
| 68 | +++ |
| 69 | +++ |
| 70 | +++ |
| 71 | ++ |
| 72 | +++ |
| 73 | +++ |
| 74 | +++ |
| 75 | +++ |
| 76 | +++ |
| 77 | +++ |
| 78 | ++ |
| 79 | + |
| 80 | ++ |
| 81 | +++ |
| 82 | ++ |
| 83 | +++ |
| 84 | +++ |
| 85 | +++ |
| 86 | +++ |
| 87 | +++ |
| 88 | +++ |
| 89 | +++ |
| 90 | + |
| 91 | + |
| 92 | + |
| 93 | + |
| 94 | + |
| 95 | + |
| 96 | + |
| 97 | + |
| 98 | + |
| 99 | + |
| 100 | + |
| 101 | +++ |
| 102 | +++ |
| 103 | +++ |
| 104 | +++ |
| 105 | +++ |
| 106 | ++ |
| 107 | ++ |
| 108 | +++ |

| EXAMPLE | $K_i$-$\sigma_1$ |
|---------|------------------|
| 109 | +++ |
| 110 | +++ |
| 111 | +++ |
| 112 | +++ |
| 113 | +++ |

The invention claimed is:

1. A compound of general Formula (I):

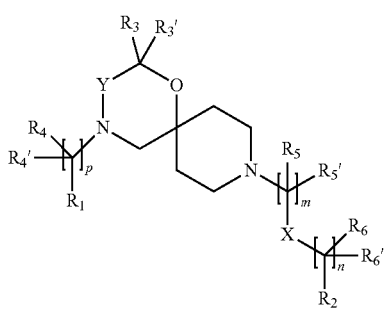

wherein
p is 0 or 1;
m is 1 or 2;
n is 0;
Y is —$CH_2$—;
X is a bond;
$R_1$ is selected from the group consisting of substituted or unsubstituted $C_{1-6}$ alkyl, substituted or unsubstituted $C_{2-6}$ alkenyl, substituted or unsubstituted $C_{2-6}$ alkynyl and substituted or unsubstituted cycloalkyl;
wherein the cycloalkyl in $R_1$, if substituted, is substituted with one or more substituent/s selected from the group consisting of halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, —$S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ and $C(CH_3)_2OR_{11}$;
additionally, cycloalkyl in $R_1$, if substituted, may also be substituted with $\nabla$ or =O;
wherein the alkyl, alkenyl or alkynyl in $R_1$, if substituted, is substituted with one or more substituent/s selected from the group consisting of —$OR_{11}$, halogen, —CN, haloalkyl, haloalkoxy and —$NR_{11}R_{11'''}$;
wherein $R_{11}$, $R_{11'}$ and $R_{11''}$ are independently selected from the group consisting of hydrogen, unsubstituted $C_{1-6}$ alkyl, unsubstituted $C_{2-6}$ alkenyl and unsubstituted $C_{2-6}$ alkynyl;
and wherein $R_{11'''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;
$R_2$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted monocyclic aryl and substituted or unsubstituted monocyclic heterocyclyl,
wherein said cycloalkyl, aryl or heterocyclyl in $R_2$, if substituted, is substituted with one or more substituent/s selected from the group consisting of halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, —$S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;
additionally, cycloalkyl or non-aromatic heterocyclyl in $R_2$, if substituted, may also be substituted with $\nabla$ or =O;
wherein the alkyl, alkenyl or alkynyl in $R_2$, if substituted, is substituted with one or more substituent/s selected from the group consisting of —$OR_{12}$, halogen, —CN, haloalkyl, haloalkoxy and —$NR_{12}R_{12'''}$;
wherein $R_{12}$, $R_{12'}$ and $R_{12''}$ are independently selected from the group consisting of hydrogen, unsubstituted $C_{1-6}$ alkyl, unsubstituted $C_{2-6}$ alkenyl and unsubstituted $C_{2-6}$ alkynyl;
and wherein $R_{12'''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;
$R_3$ and $R_{3'}$ are independently selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
alternatively, $R_3$ and $R_{3'}$ taken together with the connecting C-atom may form a substituted or unsubstituted cycloalkyl;
$R_4$ and $R_{4'}$ are independently selected from the group consisting of hydrogen, substituted or unsubstituted $C_{1-9}$ alkyl, substituted or unsubstituted $C_{2-9}$ alkenyl and substituted or unsubstituted $C_{2-9}$ alkynyl;
$R_5$ and $R_{5'}$ are both hydrogen;
$R_6$ and $R_{6'}$ are both hydrogen;
optionally as a stereoisomers, including enantiomers and diastereomers, a racemate or in form of a mixture of at least two of the stereoisomers, including enantiomers and/or diastereomers, in any mixing ratio, or a corresponding salt thereof, or a corresponding solvate thereof.

2. The compound according to claim 1, wherein
$R_3$ is selected from the group consisting of hydrogen and substituted or unsubstituted $C_{1-6}$ alkyl;
$R_{3'}$ is selected from the group consisting of hydrogen, and substituted or unsubstituted $C_{1-6}$ alkyl;
alternatively, $R_3$ and $R_{3'}$, taken together with the connecting C-atom may form a substituted or unsubstituted cycloalkyl.

3. The compound according to claim 1, wherein $R_3$ is substituted or unsubstituted $C_{1-6}$ alkyl.

4. The compound according to claim 1, wherein $R_{3'}$ is hydrogen.

5. The compound according to claim 1, wherein the compound of Formula (I) is a compound of Formula (I'), ($I^{a'}$), ($I^{b'}$) or ($I^{c'}$)

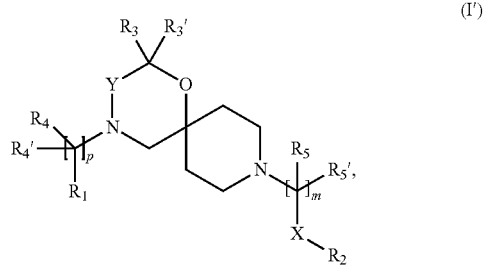

-continued

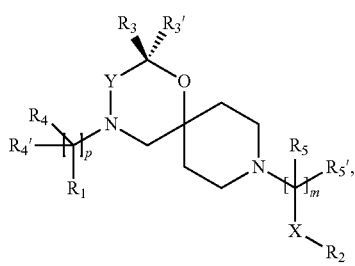
(I<sup>a'</sup>)

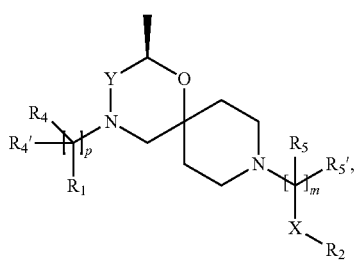
(I<sup>b'</sup>)

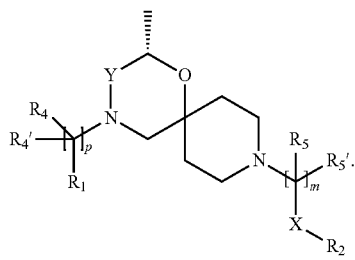
(I<sup>c'</sup>)

6. The compound according to claim 1, wherein the compound of Formula (I) is a compound of Formula (I<sup>2'</sup>)

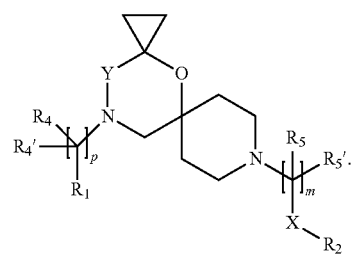
(I<sup>2'</sup>)

7. The compound according to claim 1, wherein
R$_1$ is substituted or unsubstituted C$_{1-6}$ alkyl.

8. The compound according to claim 7, wherein
R$_1$ is a substituted or unsubstituted group selected from the group consisting of methyl, ethyl and propyl.

9. The compound according to claim 7, wherein
R$_1$ is an unsubstituted group selected from the group consisting of methyl, ethyl and propyl.

10. The compound according to claim 1, wherein
R$_2$ is selected from hydrogen, substituted or unsubstituted C$_{1-6}$ alkyl, substituted or unsubstituted monocyclic aryl and substituted or unsubstituted monocyclic heterocyclyl.

11. The compound according to claim 10, wherein
R$_2$ is hydrogen or a substituted or unsubstituted group selected from methyl, ethyl, propyl, isopropyl, isobutyl, phenyl and pyridine.

12. The compound according to claim 10, wherein
R$_2$ is an unsubstituted group selected from the group consisting of methyl, ethyl, propyl, isopropyl isobutyl, substituted or unsubstituted phenyl or substituted or unsubstituted pyridine.

13. The compound according to claim 1, wherein the compound is selected from the group consisting of:
  8-(2-(3-fluoropyridin-2-yl)ethyl)-12-isopropyl-4-oxa-8, 12-diazadispiro[2.1.5.3]tridecane,
  9-(2-(3-fluoropyridin-2-yl)ethyl)-4-isopropyl-1-oxa-4,9-diazaspiro[5.5]undecane,
  (S)-9-(2-(3-fluoropyridin-2-yl)ethyl)-4-isopropyl-2-methyl-1-oxa-4,9-diazaspiro[5.5]undecane,
  (R)-9-(2-(3-fluoropyridin-2-yl)ethyl)-4-isopropyl-2-methyl-1-oxa-4,9-diazaspiro[5.5]undecane,
  8-(2-(3-fluoropyridin-2-yl)ethyl)-12-propyl-4-oxa-8,12-diazadispiro[2.1.5.3]tridecane,
  12-ethyl-8-(2-(3-fluoropyridin-2-yl)ethyl)-4-oxa-8,12-diazadispiro[2.1.5.3]tridecane,
  8-(2-(3-fluoropyridin-2-yl)ethyl)-12-isobutyl-4-oxa-8, 12-diazadispiro[2.1.5.3]tridecane,
  8-(2-(3-fluoropyridin-2-yl)ethyl)-12-methyl-4-oxa-8,12-diazadispiro[2.1.5.3]tridecane, and/or
  8-(2,5-difluorophenethyl)-12-isobutyl-4-oxa-8,12-diazadispiro[2.1.5.3]tridecane,
  12-isobutyl-8-(2-(6-methoxypyridin-2-yl)ethyl)-4-oxa-8, 12-diazadispiro[2.1.5.3]tridecane,
  8-(2-(3-chloropyridin-2-yl)ethyl)-12-isobutyl-4-oxa-8, 12-diazadispiro[2.1.5.3]tridecane,
  2-(2-(12-isobutyl-4-oxa-8,12-diazadispiro[2.1.5.3]tridecan-8-yl)ethyl)nicotinonitrile,
  8-(2-(3-fluoropyridin-2-yl)ethyl)-12-isopentyl-4-oxa-8, 12-diazadispiro[2.1.5.3]tridecane,
  8-(2-(3-fluoropyridin-2-yl)ethyl)-12-neopentyl-4-oxa-8, 12-diazadispiro[2.1.5.3]tridecane,
  12-(sec-butyl)-8-(2-(3-fluoropyridin-2-yl)ethyl)-4-oxa-8, 12-diazadispiro[2.1.5.3]tridecane,
  4-ethyl-9-(2-(3-fluoropyridin-2-yl)ethyl)-2,2-dimethyl-1-oxa-4,9-diazaspiro[5.5]undecane,
  (S)-4-ethyl-9-(2-(3-fluoropyridin-2-yl)ethyl)-2-methyl-1-oxa-4,9-diazaspiro[5.5]undecane,
  (S)-9-(2-(3-fluoropyridin-2-yl)ethyl)-2-methyl-4-propyl-1-oxa-4,9-diazaspiro[5.5]undecane,
  4-Isopropyl-2-methyl-9-phenethyl-1-oxa-4,9-diazaspiro[5.5]undecane,
  4-(cyclopropylmethyl)-9-phenethyl-1-oxa-4,9-diazaspiro[5.5]undecane,
  4-Ethyl-2-methyl-9-phenethyl-1-oxa-4,9-diazaspiro[5.5]undecane, and
  4-isopropyl-2,2-dimethyl-9-phenethyl-1-oxa-4,9-diazaspiro[5.5]undecane.

14. A process for the preparation of the compound of Formula (I) according to claim 1, wherein said process comprises:

a) an intramolecular cyclization of a compound of formula VIIa

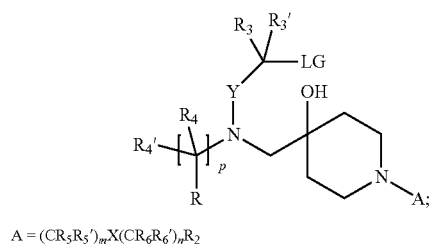

VIIa $A = (CR_5R_5')_mX(CR_6R_6')_nR_2$ or b) the reaction of a compound of formula VIIIH

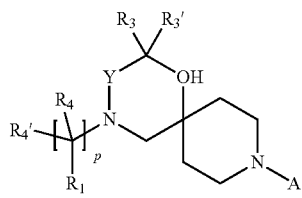

VIIIH

A = H with a compound of formula IX, X or XI,

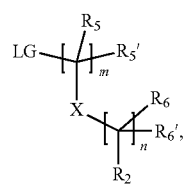

IX

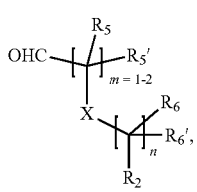

X

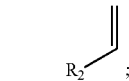

XI

or c1) by the alkylation of a compound of formula XIV

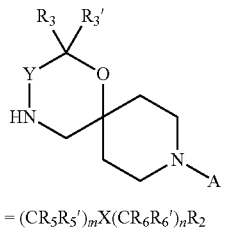

XIV $A = (CR_5R_5')_mX(CR_6R_6')_nR_2$ with a compound of formula XV

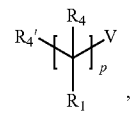

XV wherein the compound of formula XV is an alkylating agent and V a leaving group, or alternatively by the reductive amination reaction of a compound of formula XIV with a compound of formula XV, being the compound of formula XV an aldehyde and V a C(O)H group, wherein $R_1$, $R_{1'}$, $R_2$, $R_3$, $R_{3'}$, $R_4$, $R_{4'}$, $R_5$, $R_{5'}$, $R_6$, $R_{6'}$, m, n, p, X and Y have the meanings as defined in claim 1 for the compound of Formula (I) and LG represents a leaving group, including halogen, mesylate, tosylate and triflate.

15. A process for the preparation of the compound of Formula (I) according to claim 1, employing a compound of Formula II, IIP, III, IIIP, IVa, IVb, Vb, VbP, Va, VaP, VI, VIIa, VIIb, VIIbP, VIIIP, VIIIH, IX, X, XI, XII, XIIP, XIII, XIIIP, XIV, XIVP, XIVH, XV, XVI, XVIP, XVIH, XXVIIa, XXVIIb, XXVIIc, Ih, XXXP, XXXH, XXXIII, XXXIIIP, XXXIIIH, XXXIV, XXXIVP or XXXIVH,

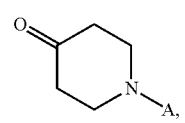

II $A = (CR_5R_5')_mX(CR_6R_6')_nR_2$
IIP A = P

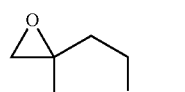

III $A = (CR_5R_5')_mX(CR_6R_6')_nR_2$
IIIP A = P

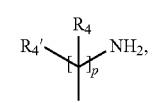

IVa

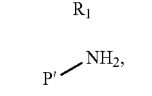

IVb

-continued
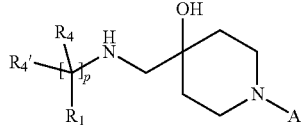
A = (CR₅R₅')ₘX(CR₆R₆')ₙR₂
VaP A = P
Va
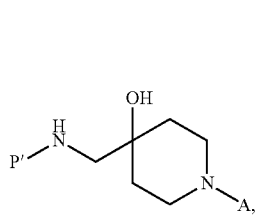
A = (CR₅R₅')ₘX(CR₆R₆')ₙR₂
VbP A = P
Vb
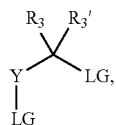
VI
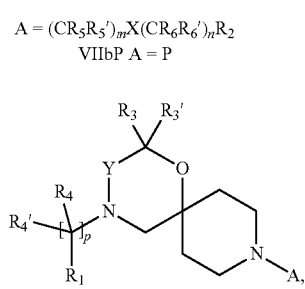
A = (CR₅R₅')ₘX(CR₆R₆')ₙR₂
VIIaP A = P
VIIa
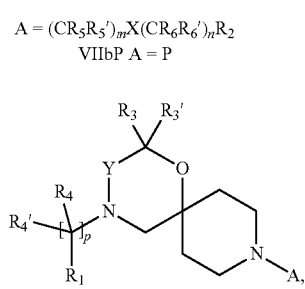
A = (CR₅R₅')ₘX(CR₆R₆')ₙR₂
VIIbP A = P
VIIb
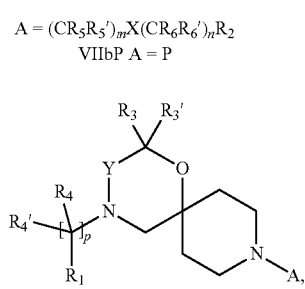
A = (CR₅R₅')ₘX(CR₆R₆')ₙR₂
VIIIP A = P
VIIIH A = H
I
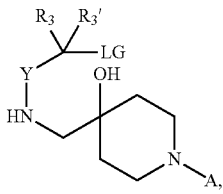
A = (CR₅R₅')ₘX(CR₆R₆')ₙR₂
XIIIP A = P
XII
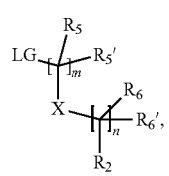
IX
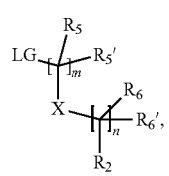
X
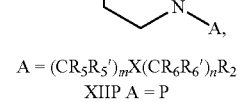
XI
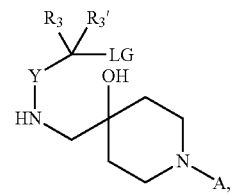
A = (CR₅R₅')ₘX(CR₆R₆')ₙR₂
XIIP A = P
XII
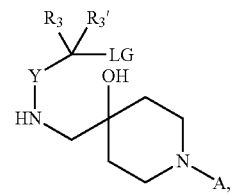
A = (CR₅R₅')ₘX(CR₆R₆')ₙR₂
XIIIP A = P
XIII
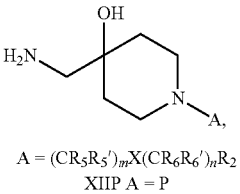
A = (CR₅R₅')ₘX(CR₆R₆')ₙR₂
XIIP A = P
XII XIII 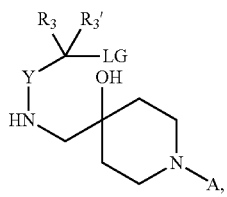

A = (CR₅R₅')ₘX(CR₆R₆')ₙR₂
XIIIP A = P

XIV 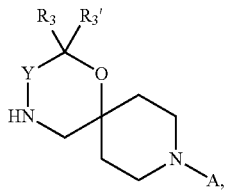

A = (CR₅R₅')ₘX(CR₆R₆')ₙR₂
XIVP A = P
XIVH A = H

XV 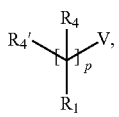

XVI 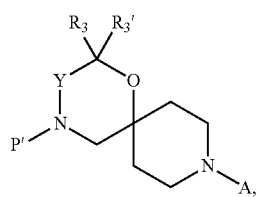

A = (CR₅R₅')ₘX(CR₆R₆')ₙR₂
XVIP A = P
XVIH A = H

XXVIIa R₃X',

XXVIIb R₃'X',

XXVIIc 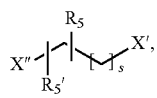

Ih 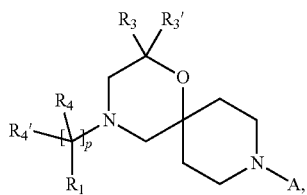

A = (CR₅R₅')ₘX(CR₆R₆')ₙR₂
XXXP A = P
XXXH A = H

XXXIII 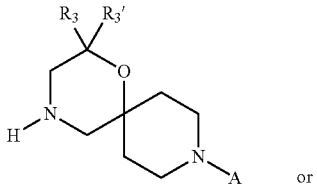

A = (CR₅R₅')ₘX(CR₆R₆')ₙR₂
XXXIIIP A = P
XXXIIIH A = H or

XXXIV 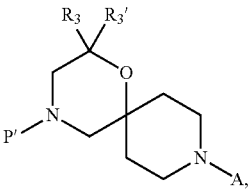

A = (CR₅R₅')ₘX(CR₆R₆')ₙR₂
XXXIVP A = P
XXXIVH A = H wherein $R_1$, $R_{1'}$, $R_2$, $R_3$, $R_{3'}$, $R_4$, $R_{4'}$, $R_5$, $R_{5'}$, $R_6$, $R_{6'}$, m, n, p, X and Y have the meanings as defined in claim 1 for the compound of Formula (I), LG represents a leaving group, including halogen, mesylate, tosylate and triflate, P represents a suitable protecting group, including Boc, P' represents a suitable protecting group, including 4-methoxybenzyl and benzyl, s represents 1, 2, 3 or 4, $R_s$ and $R_{s'}$ represent hydrogen or alkyl, Q represents methyl or benzyl, X' and X" independently represent a leaving group, including halogen, mesylate, tosylate and triflate, and V represents an aldehyde or another leaving group, including halogen, mesylate, tosylate or triflate.

16. A pharmaceutical composition which comprises the compound according to claim 1 or a pharmaceutically acceptable salt thereof, and a pharmaceutically acceptable carrier, adjuvant or vehicle.

17. A method of treating drug abuse or addiction in a subject in need thereof, comprising administration of an effective amount of the compound according to claim 1.

18. A compound selected from the group consisting of
4-(2-cyclopropylethyl)-2-methyl-9-phenethyl-1-oxa-4,9-diazaspiro[5.5]undecane,
12-ethyl-8-(2-phenoxyethyl)-4-oxa-8,12-diazadispiro[2.1.5.3]tridecan-13-one,
and
12-ethyl-8-(tetrahydro-2H-pyran-4-yl)-4-oxa-8,12-diazadispiro[2.1.5.3]tridecan-13-one,
optionally as a stereoisomer, including enantiomers and diastereomers, a racemate or in form of a mixture of at least two stereoisomers, including enantiomers and/or diastereomers, in any mixing ratio, or a corresponding salt thereof, or a corresponding solvate thereof.

\* \* \* \* \*

UNITED STATES PATENT AND TRADEMARK OFFICE
CERTIFICATE OF CORRECTION

PATENT NO. : 11,649,248 B2
APPLICATION NO. : 17/128738
DATED : May 16, 2023
INVENTOR(S) : Marina Virgili-Bernado, Carmen Almansa-Rosales and Carlos Alegret-Molina It is certified that error appears in the above-identified patent and that said Letters Patent is hereby corrected as shown below:

In the Claims

Claim 14, Column 187, Line 45: "$R_5$" should read -- $R_s$ --.
　　　　　　Line 48: "$R_5$" should read -- $R_{s'}$ --.

Signed and Sealed this
Seventeenth Day of October, 2023

Katherine Kelly Vidal
*Director of the United States Patent and Trademark Office*